(12) United States Patent
Bradley et al.

(10) Patent No.: US 11,920,128 B2
(45) Date of Patent: Mar. 5, 2024

(54) METHODS, CELLS AND ORGANISMS

(71) Applicant: Kymab Limited, Cambridge (GB)

(72) Inventors: Allan Bradley, Cambridge (GB); Hanif Ali, Cambridge (GB); E-Chiang Lee, Cambridge (GB)

(73) Assignee: Kymab Limited, Cambridge (GB)

( * ) Notice: Subject to any disclaimer, the term of this patent is extended or adjusted under 35 U.S.C. 154(b) by 740 days.

(21) Appl. No.: 16/516,996

(22) Filed: Jul. 19, 2019

(65) Prior Publication Data

US 2019/0338274 A1 Nov. 7, 2019

Related U.S. Application Data

(63) Continuation of application No. 15/094,624, filed on Apr. 8, 2016, now abandoned, which is a continuation of application No. 14/490,549, filed on Sep. 18, 2014, now abandoned.

(30) Foreign Application Priority Data

Sep. 18, 2013 (GB) ..................................... 1316560
Dec. 2, 2013 (GB) ..................................... 1321210

(51) Int. Cl.
*A61K 48/00* (2006.01)
*C07K 16/00* (2006.01)
*C12N 5/0781* (2010.01)
*C12N 15/10* (2006.01)
*C12N 15/90* (2006.01)

(52) U.S. Cl.
CPC ........ *C12N 15/102* (2013.01); *A01K 67/0278* (2013.01); *C07K 16/00* (2013.01); *C12N 5/0635* (2013.01); *C12N 15/907* (2013.01); *A01K 2207/15* (2013.01); *A01K 2217/052* (2013.01); *A01K 2217/072* (2013.01); *A01K 2227/105* (2013.01); *A01K 2267/01* (2013.01); *C07K 2317/14* (2013.01); *C07K 2317/20* (2013.01); *C07K 2317/24* (2013.01); *C07K 2317/52* (2013.01); *C07K 2317/56* (2013.01); *C12N 2510/04* (2013.01); *C12N 2800/80* (2013.01)

(58) Field of Classification Search
CPC ............................ C12N 2310/20; A61K 48/00
See application file for complete search history.

(56) References Cited

U.S. PATENT DOCUMENTS

| | | | |
|---|---|---|---|
| 5,981,175 | A | 11/1999 | Loring et al. |
| 8,546,553 | B2 | 10/2013 | Terns et al. |
| 8,697,359 | B1 | 4/2014 | Zhang |
| 8,703,489 | B2 | 4/2014 | Wang et al. |
| 8,771,945 | B1 | 7/2014 | Zhang |
| 9,228,208 | B2 | 1/2016 | Frendewey et al. |
| 2004/0018626 | A1 | 1/2004 | Murphy et al. |
| 2010/0047805 | A1 | 2/2010 | Wang |
| 2010/0076057 | A1 | 3/2010 | Sontheimer et al. |
| 2011/0119779 | A1 | 5/2011 | Shizuya et al. |
| 2011/0189776 | A1 | 8/2011 | Terns et al. |
| 2011/0223638 | A1 | 9/2011 | Wiedenheft et al. |
| 2012/0167237 | A1 | 6/2012 | Bradley et al. |
| 2012/0185956 | A1 | 7/2012 | Gingras |
| 2012/0204278 | A1 | 8/2012 | Bradley et al. |
| 2013/0095565 | A1 | 4/2013 | Frendewey et al. |
| 2013/0130248 | A1 | 5/2013 | Haurwitz et al. |
| 2013/0243759 | A1 | 9/2013 | Friedrich et al. |
| 2013/0309670 | A1 † | 11/2013 | Frendewey |
| 2014/0065142 | A1 | 3/2014 | Roschke et al. |
| 2014/0068797 | A1 | 3/2014 | Doudna et al. |
| 2014/0154701 | A1 | 6/2014 | MacDonald et al. |
| 2014/0221734 | A1 | 8/2014 | Gong et al. |
| 2014/0349400 | A1 | 11/2014 | Jakimo et al. |
| 2014/0349405 | A1 | 11/2014 | Sontheimer et al. |

(Continued)

FOREIGN PATENT DOCUMENTS

WO WO-2008/108989 A2 9/2008
WO WO-2010/011961 A2 1/2010

(Continued)

OTHER PUBLICATIONS

NCBI News. 2003; First version of human genome reference sequence debuts on DNA's 50th. On the web at www.ncbi.nlm.nih.gov/Web/Newsltr/Spring03/human.html#:~:text=The%20typical%20confirmed%20human%20gene,length%20of%205%2C478%20base%20pairs. pp. 1-2.*

(Continued)

*Primary Examiner* — Paul J Holland
(74) *Attorney, Agent, or Firm* — LATHROP GPM LLP; James H. Velema, Esq.; Michael Spellberg, Esq.

(57) ABSTRACT

The invention relates to an approach for introducing one or more desired insertions and/or deletions of known sizes into one or more predefined locations in a nucleic acid (eg, in a cell or organism genome). They developed techniques to do this either in a sequential fashion or by inserting a discrete DNA fragment of defined size into the genome precisely in a predefined location or carrying out a discrete deletion of a defined size at a precise location. The technique is based on the observation that DNA single-stranded breaks are preferentially repaired through the HDR pathway, and this reduces the chances of indels (eg, produced by NHEJ) in the present invention and thus is more efficient than prior art techniques. The invention also provides sequential insertion and/or deletions using single- or double-stranded DNA cutting.

19 Claims, 6 Drawing Sheets

Specification includes a Sequence Listing.

(56) References Cited

U.S. PATENT DOCUMENTS

| | | |
|---|---|---|
| 2014/0357523 A1 | 12/2014 | Zeiner et al. |
| 2015/0031089 A1 | 1/2015 | Lindstrom |
| 2015/0059009 A1 | 2/2015 | McWhirter et al. |
| 2015/0079680 A1 | 3/2015 | Bradley et al. |
| 2016/0177340 A1 | 6/2016 | Bradley et al. |
| 2016/0257948 A1 | 9/2016 | Bradley et al. |
| 2016/0257974 A1 | 9/2016 | Bradley et al. |
| 2017/0275611 A1 | 9/2017 | Bradley et al. |

FOREIGN PATENT DOCUMENTS

| | | |
|---|---|---|
| WO | WO-2010/054108 A2 | 5/2010 |
| WO | WO-2010/054154 A2 | 5/2010 |
| WO | WO-2010/093966 A2 | 8/2010 |
| WO | WO-2011/146121 A1 | 11/2011 |
| WO | WO-2012/054726 A1 | 4/2012 |
| WO | WO-2012/164565 A1 | 12/2012 |
| WO | WO-2013/098244 A1 | 4/2013 |
| WO | WO-2013/061078 A1 | 5/2013 |
| WO | WO-2013/181440 A1 | 5/2013 |
| WO | WO-2013/141680 A1 | 9/2013 |
| WO | WO-2013/142578 A1 | 9/2013 |
| WO | WO 2013/163394 A1 | 10/2013 |
| WO | 2013176772 A1 † | 11/2013 |
| WO | WO-2013/169398 A2 | 11/2013 |
| WO | WO-2013/169802 A1 | 11/2013 |
| WO | WO-2013/176772 A1 | 11/2013 |
| WO | WO-2013/188037 A2 | 12/2013 |
| WO | WO-2013/188522 A2 | 12/2013 |
| WO | WO-2014/022702 A1 | 2/2014 |
| WO | WO-2014/065596 A1 | 5/2014 |
| WO | WO-2014/089290 A1 | 6/2014 |
| WO | WO-2014/093479 A1 | 6/2014 |
| WO | WO-2014/093595 A1 | 6/2014 |
| WO | WO-2014/093622 A2 | 6/2014 |
| WO | WO-2014/093635 A1 | 6/2014 |
| WO | WO-2014/093655 A1 | 6/2014 |
| WO | WO-2014/093661 A2 | 6/2014 |
| WO | WO-2014/093694 A1 | 6/2014 |
| WO | WO-2014/093701 A1 | 6/2014 |
| WO | WO-2014/093709 A1 | 6/2014 |
| WO | WO-2014/093712 A1 | 6/2014 |
| WO | WO-2014/093718 A1 | 6/2014 |
| WO | WO-2014/099744 A1 | 6/2014 |
| WO | WO-2014/099750 A2 | 6/2014 |
| WO | WO-2014/113493 A1 | 7/2014 |
| WO | WO-2014/130955 A1 | 8/2014 |
| WO | 2014131833 A1 † | 9/2014 |
| WO | WO-2014/131833 A1 | 9/2014 |
| WO | WO-2014/143381 A2 | 9/2014 |
| WO | WO-2014/144155 A1 | 9/2014 |
| WO | WO-2014/144288 A1 | 9/2014 |
| WO | WO-2014/144592 A2 | 9/2014 |
| WO | WO-2014/144761 A2 | 9/2014 |
| WO | WO-2014/150624 A1 | 9/2014 |
| WO | WO-2014/152432 A2 | 9/2014 |
| WO | WO-2014/165825 A2 | 10/2014 |
| WO | WO-2014/172458 A1 | 10/2014 |
| WO | WO 2014/172470 A2 | 10/2014 |
| WO | WO-2014/172470 A2 | 10/2014 |
| WO | WO-2014/182700 A1 | 11/2014 |
| WO | WO-2014/190181 A1 | 11/2014 |
| WO | WO-2014/191128 A1 | 12/2014 |
| WO | WO-2014/191518 A1 | 12/2014 |
| WO | WO-2014/191521 A2 | 12/2014 |
| WO | WO-2014/197568 A2 | 12/2014 |
| WO | WO 2014/197568 A2 | 12/2014 |
| WO | WO-2014/197748 A2 | 12/2014 |
| WO | WO-2014/201015 A2 | 12/2014 |
| WO | WO-2014/204723 A1 | 12/2014 |
| WO | WO-2014/204724 A1 | 12/2014 |
| WO | WO-2014/204725 A1 | 12/2014 |
| WO | WO-2014/204726 A1 | 12/2014 |
| WO | WO-2014/204727 A1 | 12/2014 |
| WO | WO-2014/204728 A1 | 12/2014 |
| WO | WO-2014/204729 A1 | 12/2014 |
| WO | WO-2014/010114 A1 | 1/2015 |
| WO | WO-2015/006290 A1 | 1/2015 |
| WO | WO-2015/006294 A1 | 1/2015 |
| WO | WO-2015/006498 A2 | 1/2015 |
| WO | WO-2015-006747 A2 | 1/2015 |
| WO | WO-2015/013583 A2 | 1/2015 |

OTHER PUBLICATIONS

Addgene. 2022; Promoters. On the web at www.addgene.org/mol-bio-reference/promoters/ pp. 1-3.*

Wikipedia. 2022; Enhancer (genetics). On the web at en.wikipedia.org/wiki/Enhancer_(genetics). pp. 1-14.*

Al-Attar et al., "Clustered regularly interspaced short palindromic repeats (CRISPRs): the hallmark of an ingenious antiviral defense mechanism in prokaryotes," Bioi. Chem., vol. 392, pp. 277-289 (Apr. 2011 ).

Anders et al., Structural basis of PAM-dependent target DNA recognition by the Cas9 endonuclease; Nature, vol. 513, pp. 569-573,2014.

Carroll, "A CRISPR Approach to Gene Targeting," Moleculartherapy, vol. 20, No. 9, pp. 1658-1660 (Sep. 2012).

Carroll, "Staying on target with CRISPR-Cas," Nature Biotechnology, vol. 31, No. 9, pp. 807-809 (Sep. 2013).

Chang et al., "Genome editing with RNA-guided Cas9 nuclease in Zebrafish embryos," Cell Research, (2013), pp. 165-472, vol. 23.

Chen et al., "PiggyBac transposon-mediated, reversible gene transfer in human embryonic stem cells", Stem Cell and Development, 19(6): 763-771 (2010).

Cho et al., "Targeted genome engineering in human cells with the Cas9 RNA-guided endonuclease," Nature Biotechnology, (Mar. 2013), pp. 230-232, vol. 31, No. 3.

Cong et al., "Multiplex Genome Engineering Using CRISPR/Cas Systems", Science, 339(6121): 819-823 (2013).

Dickinson et al., "Engineering the Caenorhabditis elegans genome using Cas9-triggered homologous recombination", Nat Methods, 10(10):1028-34 (2013).

Esvelt et al., "Orthogonal Cas9 proteins for RNA-guided gene regulation and editing," Nature Methods, advanced online publication, accepted Aug. 27; published online Sep. 29, 2013; DOI:10.1038.2681, pp. 1-6.

Fujii et al., "Efficient generation of large-scale genome-modified mice using gRNA and CAS9 endonuclease", Nucleic Acids Research, 1-9 (2013).

Gaj et al., "ZFN, TALEN, and CRSPIR/Cas-based methods for genome engineering", Trends in Biotechnology, 31 (7): 397-405 (2013).

Gasiunas et al., "Cas9-crRNA ribonculeoprotein complex mediates specific DNA cleavage for adaptive immunity in bacteria," Proceedings of the National Academy of Sciences USA, vol. 109(39), pp. E2579-E2586 (Sep. 4, 2012).

Gratz et al., "Genome Engineering of Drosophila with the CRIS PR RNA-Guided Cas9 Nuclease," Genetics, vol. 194, pp. 1029-1035 (Aug. 2013).

Hale et al., "Essential Features and Rational Design ofCRISPR RNAs that Function with the Cas RAMP Module Complex to Cleave RNAs," Molecular Cell, vol. 45, pp. 292-302 (Feb. 10, 2012).

Haurwitz et al., "Csy4 relies on an unusual catalytic dyad to position and cleave CRISPR RNA," EMBO J, vol. 31, No. 12, pp. 2824-2832 (Mar. 2012).

Hohenstein et al., "High-efficient Rosa26 knock-in vector construction for ere-regulated overexpression and RNAi," PathoGenetics, vol. 1-3, pp. 1-10 (Nov. 2, 2008).

Hsu et al., "DNA targeting specificity of RNA-guided Cas9 nucleases", Nature Biotechnology, 31(9): 827-832 (2013).

Hwang et al., "Efficient genome editing in zebrafish using a CRISPR-Cas system", Nature Biotechnology, 31(3): 227-229 (2013).

International Preliminary Report on Patentability and Written Opinion for International Application No. PCT/GB2014/052837, The International Bureau of WIPO, Geneva, Switzerland, dated Mar. 22, 2016, 13 pages.

(56) References Cited

OTHER PUBLICATIONS

International Search Report for International Application No. PCT/GB2014/052837, European Patent Office, Rijswijk, Netherlands, dated Feb. 27, 2015, 8 pages.
Jiang et al., "CRISPR-assisted editing of bacterial genomes," Nature Biotechnology, (Mar. 2013), pp. 233-239, vol. 31, No. 3.
Jinek et al., "Structures of Cas9 Endonucleases Reveal RNA-Mediated Conformational Activation," Science, vol. 343, pp. 1215-1226 (Mar. 14, 2012).
Jinek et al., "A Programmable Dual-RNA-Guided DNA Endonuclease in Adaptive Bacterial Immunity," Science, vol. 12 336, pp. 816-821 (Aug. 17, 2012).
Jinek, M., et al., "RNA-programmed genome editing in human cells," eLife 2:e00471, pp. 1-9, eLife Sciences Publications, United States (2013).
Kim et al., "Precision genome engineering with programmable DNA-nicking enzymes," Genome Res., vol. 22, pp. 1327-1333 (2012).
Kondo et al., "Highly improved targeting by germline-specific Cas9 expression in *Drosophila*", Genetics, 95(3): 715-721 (2013).
Li et al., Multiplex and homologous recombination-mediated genome editing in *Arabidopsis* and Nicotiana benthamian, using guide RNA and Cas9, Nature Biotechnology, (Aug. 2013), pp. 688-691, val. 31, No. 8.
Makarova et al., "Evolution and Classification of the CRISPR-CAS Systems," Nature Reviews Microbiology, vol. 9, No. 6, pp. 467-477 (Jun. 2011).
Mali et al., "RNA-guided human genome engineering via Cas9," Science, vol. 339, No. 6121, pp. 823-826 (Feb. 15, 2013).
Mali et al., "CAS9 transcriptional activators for target specificity screening and paired nickases for cooperative genome engineering," Nature Biotechnology, vol. 31, No. 9, pp. 833-838 (Sep. 2013).
Mali et al., "Cas9 as a versatile tool for engineering biology," Nature Methods, vol. 10, No. 1, pp. 957-963 (Oct. 2013).
Manjunath et al., "Newer Gene Editing Technologies Toward HIV Gene Therapy," Viruses, vol. 5, pp. 2748-2766, 2013.
Mashiko, D., et al., "Generation of mutant mice by pronuclear injection of circular plasmid expressing Cas9 and single guided RNA," Scientific Reports 3:3355, Nature Publishing Group, United Kingdom (2013).
Metzger et al., "Single-strand nicks induce homologous recombination with less toxicity than double-strand breaks using an AAV vector template," Nucleic Acids Research, vol. 39, No. 3, pp. 926-935 (Sep. 2, 2010).
Mojica, F.J., et al., "Short Motif Sequences Determine the Targets of the Prokaryotic CRISPR Defence System," Microbiology 155(Pt 3):733-740, Kluwer Academic/Plenum Publishers, United States (Mar. 2009).
Office Action (Final) dated Jul. 26, 2017, in U.S. Appl. No. 15/072,978, Bradley, A., filed Mar. 17, 2016, 11 pages.
Office Action (Non-Final) dated Apr. 13, 2017, in U.S. Appl. No. 15/072,978, Bradley, A., filed Mar. 17, 2016, 15 pages.
Office Action (Non-Final) dated Oct. 17, 2017, in U.S. Appl. No. 15/610,384, Bradley, A., filed May 31, 2017, 15 pages.
Oumard et al., "Recommended method for chromosome exploitation: RMCE-based cassette-exchange systems in animal cell biotechnology," Cytotechnology, vol. 50, pp. 93-108 (Jan. 6, 2006).
Perez-Pinera et al., "Advances in targeted genome editing," Curr. Opin. Chem. Bioi., vol. 16, No. 3-4, pp. 268-277 (2012).
Perez-Pinera et al., "Gene targeting to the ROSA26 locus directed by engineered zinc fingger nucleases," Nucleic Acid Research, vol. 40, No. 8, pp. 3741-3752 (2012).
Qiao et al., "Novel Tag-and-Exchange {RMCE) Strategies Generate Master Cell Clones with Predicable and Stable Transgene Expression Properties," J_ Mol. Bioi., vol. 390, pp. 579-594 (2009).
Ran et al., "Double nicking by RNA-guided CRISPR Cas9 for enhanced genome editing specificity", Cell, 154(6): 1380-1389 (2013).
Ran et al., "Genome engineering using the CRISPR-Cas9 system," Nature Protocols, vol. 8, No. 11, pp. 2281-2308 (2013).
Richter et al., "Exploiting CRISPR/Cas: Interference Mechanisms and Applications", International Journal of Molecular Sciences:m 14(7): 14518-14531 (2013).
Schneider et al., pMPY-ZAP: A Reusable Polymerase Chain Reaction-directed Gene Disruption Cassette for *Saccharomyces cerevisiae*; Yeast, vol. 12, pp. 129-134, 1996.
Shah et al., "Protospacer recognition motifs: Mixed identities and functional diversity," RNA Biology, vol. 10, No. 5, pp. 891-899 (May 2013).
Shen et al., "Generation of gene-modified mice via Cas9/RNA-mediated gene targeting," Cell Research, (2013), pp. 720-723, vol. 23.
Simpson et al., "Genetic variation among 129 substrains and its importance for targeted mutagenesis in mice", Nature Genetics, 16:19-27 (1997).
Thomas et al., "High-fidelity gene targeting in embryonic stem cells by using sequence replacement vectors", Mol Cell Biol, 12(7):2919-23 (1992).
Wang et al., One-Step Generation of Mice Caring Mutations in Multiple Genes by CRISPR-Cas-Mediated Genome Engineering, Cell, vol. 153, pp. 910-918 (May 9, 2013).
Wei et al., "TALEN or Cas9-Rapid, Efficient and Specific Choices for Genome Modifications," Journal of Genetics and Genomics, (2013), pp. 281-289, vol. 40.
Wiedenheft et al., "RNA-guided genetic silencing systems in bacteria and archaea," Nature, vol. 482, pp. 331-338, (Feb. 16, 2012).
Xu et al., "Cas9-Based Tools for Targeted Genome Editing and Transcriptional Control," Appl. Environ. Microbial., vol. 80(5), pp. 1544-1552, 2014.
Yang et al., "One-step generation of mice carrying mutations in multiple genes by CRISPR/Cas-mediated genome engineering," Cell, vol. 154, pp. 1370-1379 (Sep. 2013).
Yu et al., "Highly Efficient Genome Modification mediated by CRISPR/Cas9 in *Drosphila*," Genetics: Early Online, published 10.1534/genetics.113.153825, (Jul. 5, 2013), 14 pages.
Yusa et al. "A hyperactive piggyback transposase for mammalian applications," PNAS, vol. 108, No. 4, pp. 1531-1536 (Jan. 25, 2011).
Birling et al., "Site-Specific Recombinases for Manipulation of the Mouse Genome," Transgenesis Techniques, Methods in Molecular Biology, 561: 245-263 (2009).
Chen et al., "A Comparison of Exogenous Promoter Activity at the ROSA26 Locus Using a PhiC31 Integrase Mediated Cassette Exchange Approach in Mouse ES Cells," PLOS One 6(8):e23376 (2011).
Chen et al., "Efficient genome editing in Caenorhabditis elegans by CRISPR-targeted homologous recombination," Nucleic Acids Research 41(20):e193 (2013).
Cho et al., "Analysis of off-target effects of CRISPR/Cas-derived RNA-guided endonucleases and nickases," Genome Research:1-10, Cold Spring Harbor Research Lab (2014).
Di Matteo et al., "PiggyBac Toolbox," Mobile Genetic Elements, Methods in Molecular Biology (Methods and Protocols), vol. 859, Ch. 14, Humana Press, 14 pages (2012).
Farruggio et al., "Efficient reversal of phiC31 integrase recombination in mammalian cells," Biotechnol. J., 7(11): 1332-1336 (2012).
Glaser et al., "Current Issues in Mouse Genome Engineering," Nature Genetics 37(11):1187-1193, Nature Publishing Group (2005).
Leichsenring et al., "POU5f1 Transcription Factor Controls Zygotic Gene Activation In Vertebrates," Science 341(6149):1005-1009, American Association for the Advancement of Science (2013).
Maleki et al., "Application of phiC31 integrase system in stem cells biology and technology: a review," Frontiers in Life Science, 11(1): 1-10 (2018).
Menke, "Engineering Subtle Targeted Mutations in the Mouse Genome," Genesis 51:605-618, John Wiley & Sons (2013).
Oberstein et al., "Site-specific transgenesis by Cre-mediated recombination in *Drosophila*," Nature Methods, 2(8): 583-585 (2005).
Pray et al., "Transposons: The Jumping Genes," Nature Education 1(1):204, 4 pages (2008).
Roebroek et al., "Knockin Approaches," vol. 209, Chapter 10, 187-200, Transgenic Mouse, Methods and Protocols, Humana Press Inc. (2003).

(56) References Cited

OTHER PUBLICATIONS

Ryder et al., "Transposable elements as tools for genomics and genetics in *Drosophila*," Briefings in Functional Genomics and Proteomics, 2(1): 57-71 (2013).
Shan et al., "Targeted genome modification of crop plants using a CRISPR-Cas System," Nature Biotechnology 31(8):686-688, Nature Publishing Group (2016).
Sorrell et al., "Targeted Modification of Mammalian Genomes," Focus on Genome Research, Chapter 11:365-396, Nova Science Publishers (2004).
Sorrell et al., "Targeted modification of mammalian genomes," Biotechnology Advances 23:431-469, Elsevier (2005).
Touchman, "Comparative Genomics," Nature Education Knowledge, 3(10): 13, 5 pages (2010).
Turan et al., "Recombinase-Mediated Cassette Exchange (RMCE): Traditional Concepts and Current Challenges," Journal of Molecular Biology, 407: 193-221 (2011).
Turan et al., "Recombinase-Mediated Cassette Exchange (RMCE)—A rapidly-expanding toolbox for targeted genomic modifications," Gene, 515: 1-27 (2013).
Von Melchner et al., "Engineering of ES Cell Genomes with Recombinase Systems," Handbook of Stem Cells, vol. 1, Ch. 61: 609-622 (2004).
Wirth et al., "Road to precision: recombinase-based targeting technologies for genome engineering," Current Opinion in Biotechnology, 18: 411-419 (2007).
U.S. Appl. No. 16/516,996 2019/0338274, filed Jul. 19, 2019 Nov. 7, 2019, Allan Bradley.
U.S. Appl. No. 15/072,794 2016/0257948, filed Mar. 17, 2016 Sep. 8, 2016, Allan Bradley.
U.S. Appl. No. 15/610,384 2017/0275611, filed May 31, 2017 Sep. 28, 2017, Allan Bradley.
Notice of Opposition for European Patent No. 3418379 B1 (Application No. 18174860.9), dated Sep. 23, 2021, 1 page.
Opposition Against European Patent No. 3418379 B1 (Application No. 18174860.9), dated Sep. 14, 2021, 22 pages.
Electronic Acknowledgement Receipt from the European Patent Office regarding Grounds for Opposition and corresponding documents for European Patent No. 3418379 B1 (Application No. 18174860.9), dated Sep. 8, 2021, 2 pages.
Brevini et al., "No shortcuts to pig embryonic stem cells", Theriogenology, 2010, 74(4): 544-550.
Buta et al., "Reconsidering pluripotency tests: Do we still need teratoma assays?", Stem Cell Research, 2013, 11(1): 552-562.
Gómez et al., "Derivation of cat embryonic stem-like cells from in vitro-produced blastocysts on homologous and heterologous feeder cells", Theriogenology, 2010, 74(4): 498-515.
Hong et al., "Derivation and Characterization of Embryonic Stem Cells Lines from Transgenic Fischer 344 and Dark Agouti Rats", Stem Cells Development, Nov. 9, 2012, 21(9): 1571-1586.
Mali et al., "RNA-Guided Human Genome Engineering via Cas9", Science, Feb. 15, 2013, 339(6121): 823-826.
Paris et al., "Equine embyos and embryonic stem cells: Defining reliable markers of pluripotency", Theriogenology, 2010, 74(4): 516-524.
Wang et al., "One-Step Generation of Mice Carrying Mutations in Multiple Genes by CRISPR/Cas-Mediated Genome Engineering", Cell, May 9, 2013, 153(4): 910-918.

\* cited by examiner
† cited by third party

Figure 1: Precise DNA Insertion in a Predefined Location (KI)
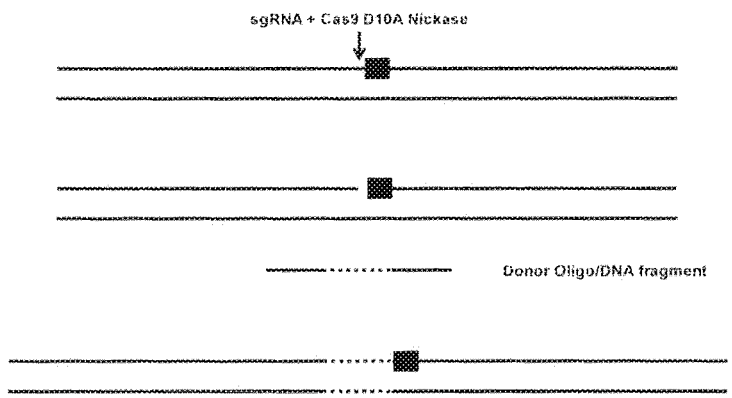
Figure 2: Precise DNA Deletion (KO)
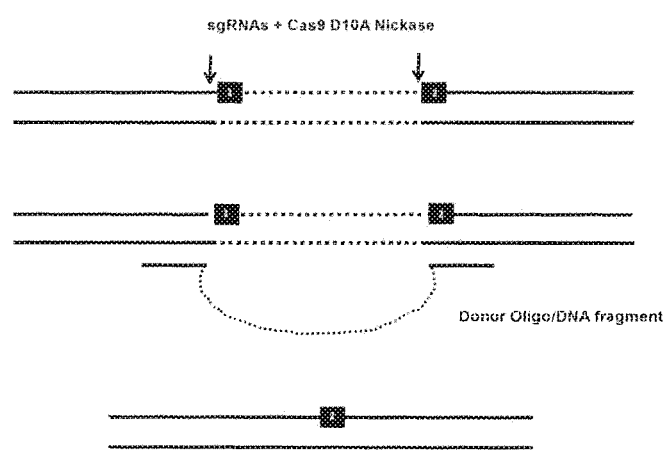

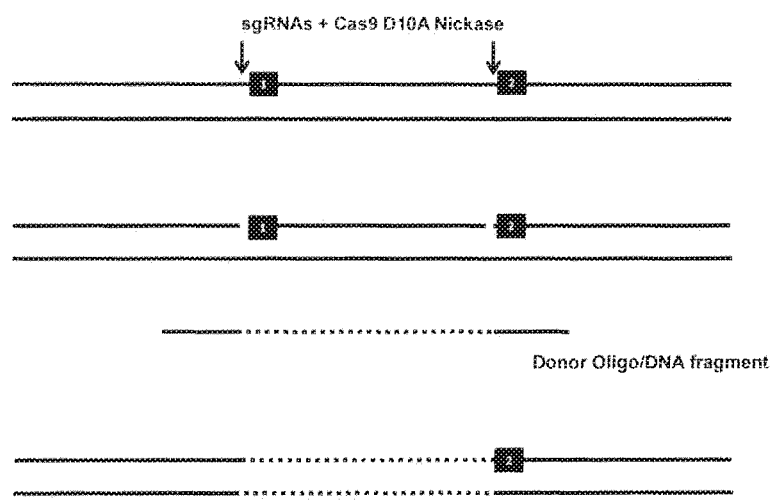
Figure 3: Precise DNA Deletion and Insertion (KO → KI)

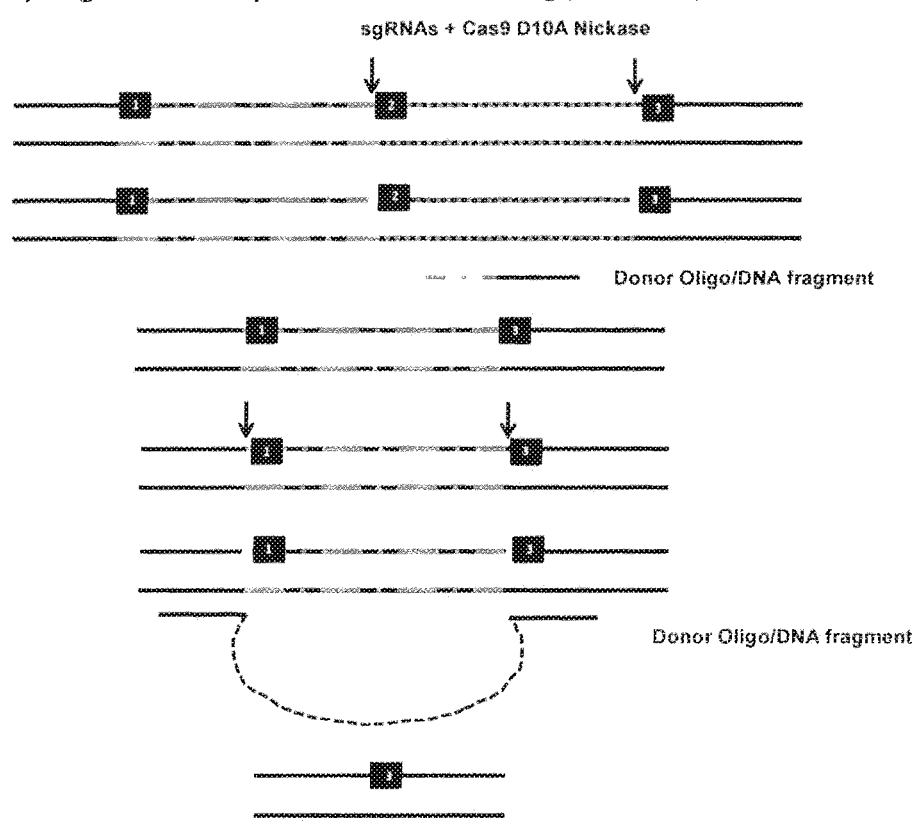

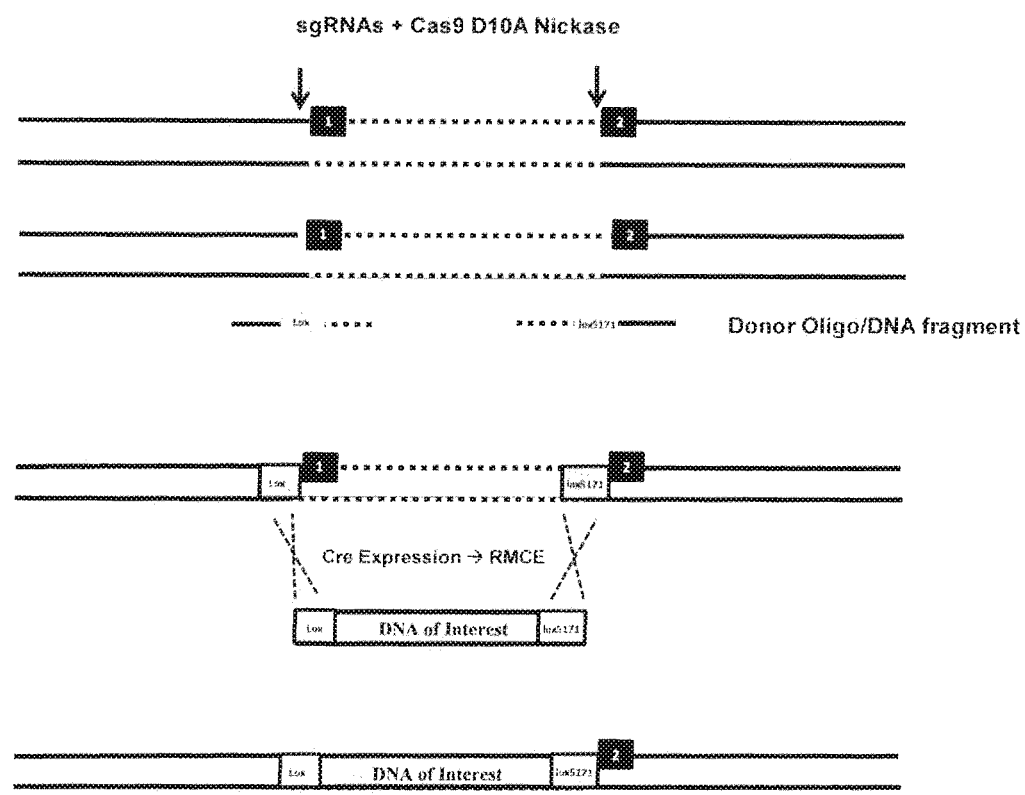
Figure 5: CRISPR/Cas mediated Lox Insertion to facilitate RMCE

SEQUENCE LISTING

<160> NUMBER OF SEQ ID NOS: 61

<210> SEQ ID NO 1
<211> LENGTH: 11
<212> TYPE: RNA
<213> ORGANISM: Artificial Sequence
<220> FEATURE:
<223> OTHER INFORMATION: an example of part of gRNA before linker
      sequence

<400> SEQUENCE: 1
uuuuagagcu a                                                          11

<210> SEQ ID NO 2
<211> LENGTH: 13
<212> TYPE: RNA
<213> ORGANISM: Artificial Sequence

```
<220> FEATURE:
<223> OTHER INFORMATION: an example of part of gRNA following linker
      sequence

<400> SEQUENCE: 2
uagcaaguua aaa                                                            13

<210> SEQ ID NO 3
<211> LENGTH: 12
<212> TYPE: RNA
<213> ORGANISM: Artificial Sequence
<220> FEATURE:
<223> OTHER INFORMATION: exemplary portion of gRNA (crRNA)
<220> FEATURE:
<221> NAME/KEY: misc_feature
<222> LOCATION: 1, 7, 8
<223> OTHER INFORMATION: n = A,U,C or G

<400> SEQUENCE: 3
nuuuuanngc ua                                                             12

<210> SEQ ID NO 4
<211> LENGTH: 16
<212> TYPE: RNA
<213> ORGANISM: Artificial Sequence
<220> FEATURE:
<223> OTHER INFORMATION: exemplary tracrRNA which comprises a portion of
      a gRNA
<220> FEATURE:
<221> NAME/KEY: misc_feature
<222> LOCATION: 5, 16
<223> OTHER INFORMATION: n = A, U, G or C
<220> FEATURE:
<221> NAME/KEY: misc_feature
<222> LOCATION: 6, 7, 8, 9
<223> OTHER INFORMATION: n = A, U, G, C or absent

<400> SEQUENCE: 4
uagcnnnnnu aaaan                                                          16

<210> SEQ ID NO 5
<211> LENGTH: 26
<212> TYPE: RNA
<213> ORGANISM: Artificial Sequence
<220> FEATURE:
<223> OTHER INFORMATION: an example of a tracrRNA

<400> SEQUENCE: 5
uagcaaguua aaauaaggcu aguccg                                              26

<210> SEQ ID NO 6
<211> LENGTH: 76
<212> TYPE: RNA
<213> ORGANISM: Artificial Sequence
<220> FEATURE:
<223> OTHER INFORMATION: an example of a gRNA

<400> SEQUENCE: 6
guuuuagagc uagaaauagc aaguuaaaau aaggcuaguc cguuaucaac uugaaaagu          60 ggcaccgagu cggugc                                                         76

<210> SEQ ID NO 7
<211> LENGTH: 1340
<212> TYPE: DNA
<213> ORGANISM: Artificial Sequence
<220> FEATURE:
<223> OTHER INFORMATION: Fragment 1A (1340 bp)
```

<400> SEQUENCE: 7

```
ggtaccgggc cccccctcga ggtcgacggt atcgataagc ttgatgaggg cctatttccc      60
atgattcctt catatttgca tatacgatac aaggctgtta gagagataat tggaattaat     120
ttgactgtaa acacaaagat attagtacaa aatacgtgac gtagaaagta ataatttctt     180
gggtagtttg cagttttaaa attatgtttt aaaatggact atcatatgct taccgtaact     240
tgaaagtatt tcgatttctt ggctttatat atcttgtgga aaggacgaaa cacccgggtct    300
tcgagaagac ctgttttaga gctagaaata gcaagttaaa ataaggctag tccgttatca     360
acttgaaaaa gtggcaccga tcggtgcttt tttgtttta gagctagaaa tagcaagtta      420
aaataaggct agtccgtttt tagcgcgtgc gccaattctg cagacaaatg gctctagagg     480
tacccgttac ataacttacg gtaaatggcc cgcctggctg accgcccaac gacccccgcc     540
cattgacgtc aatagtaacg ccaatagggg cttttccattg acgtcaatgg gtggagtatt    600
tacggtaaac tgcccacttg gcagtacatc aagtgtatca tatgccaagt acgcccccta    660
ttgacgtcaa tgacggtaaa tggcccgcct ggcattgtgc ccagtacatg accttatggg    720
actttcctac ttggcagtac atctacgtat tagtcatcgc tattaccatg gtcgaggtga    780
gccccacgtt ctgcttcact ctccccatct ccccccctc cccaccccca attttgtatt     840
tatttatttt ttaattattt tgtgcagcga tggggcggg gggggggggg gggcgcgcgc     900
caggcggggc ggggcgggc gagggcgggg gcggggcgag gcgagaggt gcggcggcag     960
ccaatcagag cggcgcgctc cgaaagttc cttttatggc gaggcggcgg cggcggcggc    1020
cctataaaaa gcgaagcgcg cggcgggcgg gagtcgctgc gacgctgcct tcgccccgtg    1080
ccccgctccg ccgccgcctc gcgccgcccg ccccggctct gactgaccgc gttactccca    1140
caggtgagcg gcgggacgg cccttctcct ccgggctgta attagctgag caagaggtaa    1200
gggtttaagg gatggttggt tggtggggta ttaatgttta attacctgga gcacctgcct    1260
gaaatcactt ttttttcaggt tggaccggtg ccaccatgga ctataaggac cacgacggag    1320
actacaagga tcatgatatt                                                1340
```

<210> SEQ ID NO 8
<211> LENGTH: 852
<212> TYPE: DNA
<213> ORGANISM: Artificial Sequence
<220> FEATURE:
<223> OTHER INFORMATION: Fragment 2 (852 bp)

<400> SEQUENCE: 8

```
atggactata aggaccacga cggagactac aaggatcatg atattgatta caaagacgat      60
gacgataaga tggcccccaaa gaagaagcgg aaggtcggta ccacggagt cccagcagcc    120
gacaagaagt acagcatcgg cctggacatc ggcaccaact ctgtgggctg gccgtgatc     180
accgacgagt acaaggtgcc cagcaagaaa ttcaaggtgc tgggcaacac cgaccggcac    240
agcatcaaga agaacctgat cggagccctg ctgttcgaca cggcgaaac agccgaggcc    300
acccggctga agagaaccgc cagaagaaga tacaccagac ggaagaaccg gatctgctat    360
ctgcaagaga tcttcagcaa cgagatggcc aaggtggacg acagcttctt ccacagactg    420
gaagagtcct tcctggtgga agaggataag aagcacgagc ggcaccccat cttcggcaac    480
atcgtggacg aggtggccta ccacgagaag taccccacca tctaccacct gagaagaaaa    540
ctggtggaca gcaccgacaa ggccgacctg cggctgatct atctggccct ggcccacatg    600
atcaagttcc ggggccactt cctgatcgag ggcgacctga accccgacaa cagcgacgtg    660
```

```
gacaagctgt tcatccagct ggtgcagacc tacaaccagc tgttcgagga aaacccatc    720 aacgccagcg gcgtggacgc caaggccatc ctgtctgcca gactgagcaa gagcagacgg   780
ctggaaaatc tgatcgccca gctgcccggc gagaagaaga atggcctgtt cggaaacctg   840
attgccctga gc                                                       852
```

<210> SEQ ID NO 9
<211> LENGTH: 920
<212> TYPE: DNA
<213> ORGANISM: Artificial Sequence
<220> FEATURE:
<223> OTHER INFORMATION: Fragment 3 (920 bp)

<400> SEQUENCE: 9

```
ggcgagaaga agaatggcct gttcggaaac ctgattgccc tgagcctggg cctgaccccc    60
aacttcaaga gcaacttcga cctggccgag gatgccaaac tgcagctgag caaggacacc   120
tacgacgacg acctggacaa cctgctggcc cagatcggcg accagtacgc cgacctgttt   180
ctggccgcca agaacctgtc cgacgccatc ctgctgagcg acatcctgag agtgaacacc   240
gagatcacca aggcccccct gagcgcctct atgatcaaga gatacgacga gcaccaccag   300
gacctgaccc tgctgaaagc tctcgtgcgg cagcagctgc ctgagaagta caaagagatt   360
ttcttcgacc agagcaagaa cggctacgcc ggctacattg acggcggagc cagccaggaa   420
gagttctaca gttcatcaa gcccatcctg aaaagatgg acggcaccga ggaactgctc    480
gtgaagctga cagagagga cctgctgcgg aagcagcgga ccttcgacaa cggcagcatc   540
ccccaccaga tccacctggg agagctgcac gccattctgc ggcggcagga agattttttac  600 ccattcctga aggacaaccg ggaaaagatc gagaagatcc tgaccttccg catcccctac   660
tacgtgggcc ctctggccag gggaaacagc agattcgcct ggatgaccag aaagagcgag   720
gaaaccatca ccccctggaa cttcgaggaa gtggtggaca agggcgcttc cgcccagagc   780
ttcatcgagc ggatgaccaa cttcgataag aacctgccca cgagaaggt gctgcccaag    840 cacagcctgc tgtacgagta cttcaccgtg tataacgagc tgaccaaagt gaaatacgtg   900
accgagggaa tgagaaagcc                                               920
```

<210> SEQ ID NO 10
<211> LENGTH: 920
<212> TYPE: DNA
<213> ORGANISM: Artificial Sequence
<220> FEATURE:
<223> OTHER INFORMATION: Fragment 4 (920 bp)

<400> SEQUENCE: 10

```
cgagctgacc aaagtgaaat acgtgaccga gggaatgaga aagcccgcct tcctgagcgg    60
cgagcagaaa aaggccatcg tggacctgct gttcaagacc aaccggaaag tgaccgtgaa   120
gcagctgaaa gaggactact tcaagaaaat cgagtgcttc gactccgtgg aaatctccgg   180
cgtggaagat cggttcaacg cctccctggg cacataccac gatctgctga aaattatcaa   240
ggacaaggac ttcctggaca atgaggaaaa cgaggacatt ctggaagata tcgtgctgac   300
cctgacactg tttgaggaca gagagatgat cgaggaacgg ctgaaaacct atgcccacct   360
gttcgacgac aaagtgatga agcagctgaa gcggcggaga tacaccggct ggggcaggct   420
gagccggaag ctgatcaacg gcatccggga caagcagtcc ggcaagacaa tcctggattt   480
cctgaagtcc gacggcttcg ccaacagaaa cttcatgcag ctgatccacg acgacagcct   540
```

| | |
|---|---|
| gacctttaaa gaggacatcc agaaagccca ggtgtccggc cagggcgata gcctgcacga | 600 |
| gcacattgcc aatctggccg gcagccccgc cattaagaag ggcatcctgc agacagtgaa | 660 |
| ggtggtggac gagctcgtga agtgatgggc ccggcacaag cccgagaaca tcgtgatcga | 720 |
| aatggccaga gagaaccaga ccacccagaa gggacagaag aacagccgcg agagaatgaa | 780 |
| gcggatcgaa gagggcatca agagctgggc agccagatcc tgaaagaac ccccgtgga | 840 |
| aaacacccag ctgcagaacg agaagctgta cctgtactac ctgcagaatg ggcgggatat | 900 |
| gtacgtggac caggaactgg | 920 |

<210> SEQ ID NO 11
<211> LENGTH: 920
<212> TYPE: DNA
<213> ORGANISM: Artificial Sequence
<220> FEATURE:
<223> OTHER INFORMATION: Fragment 5 (920 bp)

<400> SEQUENCE: 11

| | |
|---|---|
| actacctgca gaatgggcgg gatatgtacg tggaccagga actggacatc aaccggctgt | 60 |
| ccgactacga tgtggaccat atcgtgcctc agagctttct gaaggacgac tccatcgaca | 120 |
| acaaggtgct gaccagaagc gacaagaacc ggggcaagag cgacaacgtg ccctccgaag | 180 |
| aggtcgtgaa gaagatgaag aactactggc ggcagctgct gaacgccaag ctgattaccc | 240 |
| agagaaagtt cgacaatctg accaaggccg agagaggcgg cctgagcgaa ctggataagg | 300 |
| ccggcttcat caagagacag ctggtggaaa cccggcagat cacaaagcac gtggcacaga | 360 |
| tcctggactc ccgatgaac actaagtacg acgagaatga caagctgatc cgggaagtga | 420 |
| aagtgatcac cctgaagtcc aagctggtgt ccgatttccg gaaggatttc cagttttaca | 480 |
| aagtgcgcga gatcaacaac taccaccacg cccacgacgc ctacctgaac gccgtcgtgg | 540 |
| gaaccgccct gatcaaaaag taccctaagc tggaaagcga gttcgtgtac ggcgactaca | 600 |
| aggtgtacga cgtgcggaag atgatcgcca agagcgagcg ggaaatcggc aaggctaccg | 660 |
| ccaagtactt cttctacagc aacatcatga acttttttcaa gaccgagatt accctggcca | 720 |
| acggcgagat ccggaagcgg cctctgatcg agacaaacgg cgaaaccggg gagatcgtgt | 780 |
| gggataaggg ccgggatttt gccaccgtgc ggaaagtgct gagcatgccc caagtgaata | 840 |
| tcgtgaaaaa gaccgaggtg cagacaggcg gcttcagcaa agagtctatc ctgcccaaga | 900 |
| ggaacagcga taagctgatc | 920 |

<210> SEQ ID NO 12
<211> LENGTH: 789
<212> TYPE: DNA
<213> ORGANISM: Artificial Sequence
<220> FEATURE:
<223> OTHER INFORMATION: Fragment 6 (789 bp)

<400> SEQUENCE: 12

| | |
|---|---|
| agcaaagagt ctatcctgcc caagaggaac agcgataagc tgatcgccag aaagaaggac | 60 |
| tgggacccta agaagtacgg cggcttcgac agccccaccg tggcctattc tgtgctggtg | 120 |
| gtggccaaag tggaaaaggg caagtccaag aaactgaaga gtgtgaaaga gctgctgggg | 180 |
| atcaccatca tggaaagaag cagcttcgag aagaatccca tcgactttct ggaagccaag | 240 |
| ggctacaaag aagtgaaaaa ggacctgatc atcaagctgc ctaagtactc cctgttcgag | 300 |
| ctggaaaacg gccggaagag aatgctggcc tctgccggcg aactgcagaa gggaaacgaa | 360 |
| ctggccctgc cctccaaata tgtgaacttc ctgtacctgg ccagccacta tgagaagctg | 420 |

| | | | |
|---|---|---|---|
| aagggctccc | ccgaggataa | tgagcagaaa cagctgtttg tggaacagca caagcactac | 480 |
| ctggacgaga | tcatcgagca | gatcagcgag ttctccaaga gagtgatcct ggccgacgct | 540 |
| aatctggaca | aagtgctgtc | cgcctacaac aagcaccggg ataagcccat cagagagcag | 600 |
| gccgagaata | tcatccacct | gtttaccctg accaatctgg agcccctgc cgccttcaag | 660 |
| tactttgaca | ccaccatcga | ccggaagagg tacaccagca ccaaagaggt gctggacgcc | 720 |
| accctgatcc | accagagcat | caccggcctg tacgagacac ggatcgacct gtctcagctg | 780 |
| ggaggcgac | | | 789 |

<210> SEQ ID NO 13
<211> LENGTH: 535
<212> TYPE: DNA
<213> ORGANISM: Artificial Sequence
<220> FEATURE:
<223> OTHER INFORMATION: Fragment 7 (535 bp)

<400> SEQUENCE: 13

| | | | |
|---|---|---|---|
| ggcctgtacg | agacacggat | cgacctgtct cagctgggag gcgacaaaag gccggcggcc | 60 |
| acgaaaaagg | ccggccaggc | aaaaaagaaa aagtaagaat tcctagagct cgctgatcag | 120 |
| cctcgactgt | gccttctagt | tgccagccat ctgttgtttg cccctccccc gtgccttcct | 180 |
| tgaccctgga | aggtgccact | cccactgtcc tttcctaata aaatgaggaa attgcatcgc | 240 |
| attgtctgag | taggtgtcat | tctattctgg ggggtggggt ggggcaggac agcaaggggg | 300 |
| aggattggga | agagaatagc | aggcatgctg gggagcggcc gcaggaaccc ctagtgatgg | 360 |
| agttggccac | tccctctctg | cgcgctcgct cgctcactga ggccgggcga ccaaaggtcg | 420 |
| cccgacgccc | gggctttgcc | cgggcggcct cagtgagcga gcgagcgcgc agctgcctgc | 480 |
| aggggcgcct | atcgaattcc | tgcagcccgg gggatccact agttctagag cggcc | 535 |

<210> SEQ ID NO 14
<211> LENGTH: 852
<212> TYPE: DNA
<213> ORGANISM: Artificial Sequence
<220> FEATURE:
<223> OTHER INFORMATION: Fragment 2A (852 bp)

<400> SEQUENCE: 14

| | | | |
|---|---|---|---|
| atggactata | aggaccacga | cggagactac aaggatcatg atattgatta caaagacgat | 60 |
| gacgataaga | tggcccccaa | agaagaagcgg aaggtcggta ccacggagt cccagcagcc | 120 |
| gacaagaagt | acagcatcgg | cctggccatc ggcaccaact ctgtgggctg ggccgtgatc | 180 |
| accgacgagt | acaaggtgcc | cagcaagaaa ttcaaggtgc tgggcaacac cgaccggcac | 240 |
| agcatcaaga | gaacctgat | cggagccctg ctgttcgaca gcggcgaaac agccgaggcc | 300 |
| acccggctga | agagaaccgc | cagaagaaga tacaccagac ggaagaaccg gatctgctat | 360 |
| ctgcaagaga | tcttcagcaa | cgagatggcc aaggtggacg acagcttctt ccacagactg | 420 |
| gaagagtcct | tcctggtgga | agaggataag aagcacgagc ggcaccccat cttcggcaac | 480 |
| atcgtggacg | aggtggccta | ccacgagaag tacccccacca tctaccacct gagaaagaaa | 540 |
| ctggtggaca | gcaccgacaa | ggccgacctg cggctgatct atctggccct ggcccacatg | 600 |
| atcaagttcc | ggggccactt | cctgatcgag ggcgacctga accccgacaa cagcgacgtg | 660 |
| gacaagctgt | tcatccagct | ggtgcagacc tacaaccagc tgttcgagga aaacccccatc | 720 |
| aacgccagcg | gcgtggacgc | caaggccatc ctgtctgcca gactgagcaa gagcagacgg | 780 |

```
ctggaaaatc tgatcgccca gctgcccggc gagaagaaga atggcctgtt cggaaacctg    840
attgccctga gc                                                        852
```

<210> SEQ ID NO 15
<211> LENGTH: 24
<212> TYPE: DNA
<213> ORGANISM: Artificial Sequence
<220> FEATURE:
<223> OTHER INFORMATION: an example oligo
<220> FEATURE:
<221> NAME/KEY: misc_feature
<222> LOCATION: 6, 7, 8, 9, 10, 11, 12, 13, 14, 15, 16, 17, 18, 19, 20,
      21, 22, 23, 24
<223> OTHER INFORMATION: n = A,T,C or G

<400> SEQUENCE: 15

```
caccgnnnnn nnnnnnnnnn nnnn                                           24
```

<210> SEQ ID NO 16
<211> LENGTH: 24
<212> TYPE: DNA
<213> ORGANISM: Artificial Sequence
<220> FEATURE:
<223> OTHER INFORMATION: an example oligo
<220> FEATURE:
<221> NAME/KEY: misc_feature
<222> LOCATION: 5, 6, 7, 8, 9, 10, 11, 12, 13, 14, 15, 16, 17, 18, 19,
      20, 21, 22, 23
<223> OTHER INFORMATION: n = A,T,C or G

<400> SEQUENCE: 16

```
aaacnnnnnn nnnnnnnnnn nnnc                                           24
```

<210> SEQ ID NO 17
<211> LENGTH: 122
<212> TYPE: DNA
<213> ORGANISM: Artificial Sequence
<220> FEATURE:
<223> OTHER INFORMATION: Example T7-gRNA Sequence
<220> FEATURE:
<221> NAME/KEY: misc_feature
<222> LOCATION: 21, 22, 23, 24, 25, 26, 27, 28, 29, 30, 31, 32, 33, 34,
      35, 36, 37, 38, 39, 40
<223> OTHER INFORMATION: n = A,T,C or G

<400> SEQUENCE: 17

```
ttaatacgac tcactatagg nnnnnnnnnn nnnnnnnnnn gttttagagc tagaaatagc    60
aagttaaaat aaggctagtc cgttatcaac ttgaaaaagt ggcaccgagt cggtgctttt   120
tt                                                                  122
```

<210> SEQ ID NO 18
<211> LENGTH: 112
<212> TYPE: DNA
<213> ORGANISM: Artificial Sequence
<220> FEATURE:
<223> OTHER INFORMATION: Fragment 1 (111 bp)

<400> SEQUENCE: 18

```
ggtaccgggc cccccctcga ggtcgacggt atcgataagc ttgataatac gactcactat    60
agggagaatg gactataagg accacgacgg agactacaag gatcatgata tt           112
```

<210> SEQ ID NO 19
<211> LENGTH: 20
<212> TYPE: DNA
<213> ORGANISM: Artificial Sequence
<220> FEATURE:

<223> OTHER INFORMATION: primer Cas9-F

<400> SEQUENCE: 19
ttaatacgac tcactatagg                                                    20

<210> SEQ ID NO 20
<211> LENGTH: 21
<212> TYPE: DNA
<213> ORGANISM: Artificial Sequence
<220> FEATURE:
<223> OTHER INFORMATION: primer Cas9-R used for PCR amplification

<400> SEQUENCE: 20
gcgagctcta ggaattctta c                                                  21

<210> SEQ ID NO 21
<211> LENGTH: 20
<212> TYPE: DNA
<213> ORGANISM: Artificial Sequence
<220> FEATURE:
<223> OTHER INFORMATION: primer CgRNA-F

<400> SEQUENCE: 21
ttaatacgac tcactatagg                                                    20

<210> SEQ ID NO 22
<211> LENGTH: 24
<212> TYPE: DNA
<213> ORGANISM: Artificial Sequence
<220> FEATURE:
<223> OTHER INFORMATION: primer CgRNA-R

<400> SEQUENCE: 22
aaaaaagcac cgactcggtg ccac                                               24

<210> SEQ ID NO 23
<211> LENGTH: 3108
<212> TYPE: DNA
<213> ORGANISM: Artificial Sequence
<220> FEATURE:
<223> OTHER INFORMATION: Sequence of Rosa26 5-prime homology arm

<400> SEQUENCE: 23
cacatttggt cctgcttgaa cattgccatg gctcttaaag tcttaattaa gaatattaat        60
tgtgtaatta ttgttttttcc tcctttagat cattccttga ggacaggaca gtgcttgttt      120
aaggctatat ttctgctgtc tgagcagcaa caggtcttcg agatcaacat gatgttcata      180
atcccaagat gttgccattt atgttctcag aagcaagcag aggcatgatg gtcagtgaca      240
gtaatgtcac tgtgttaaat gttgctatgc agtttggatt tttctaatgt agtgtaggta      300
gaacatatgt gttctgtatg aattaaactc ttaagttaca ccttgtataa tccatgcaat      360
gtgttatgca attaccattt taagtattgt agctttcttt gtatgtgagg ataaaggtgt      420
ttgtcataaa atgtttgaa catttccca aagttccaaa ttataaaacc acaacgttag        480
aacttattta tgaacaatgg ttgtagtttc atgcttttaa aatgcttaat tattcaatta      540
acaccgtttg tgttataata tatataaaac tgacatgtag aagtgtttgt ccagaacatt      600
tcttaaatgt atactgtctt tagagagttt aatatagcat gtcttttgca acatactaac      660
ttttgtgttg gtgcgagcaa tattgtgtag tcattttgaa aggagtcatt tcaatgagtg      720
tcagattgtt ttgaatgtta ttgaacattt taaatgcaga cttgttcgtg ttttagaaag      780
caaaactgtc agaagctttg aactagaaat taaaagctg aagtatttca gagggaaat       840

```
aagctacttg ctgtattagt tgaaggaaag tgtaatagct tagaaaattt aaaaccatat    900
agttgtcatt gctgaatatc tggcagatga aaagaaatac tcagtggttc ttttgagcaa    960
tataacagct tgttatatta aaaattttcc ccacagatat aaactctaat ctataactca   1020
taaatgttac aaatggatga agcttacaaa tgtggcttga cttgtcactg tgcttgtttt   1080
agttatgtga agtttggca ataaacctat gtcctaaata gtcaaactgt ggaatgactt   1140
tttaatctat tggtttgtct agaacagtta tgttgccatt tgccctaatg gtgaaagaaa   1200
aagtggggag tgccttggca ctgttcattt gtggtgtgaa ccaaagaggg gggcatgcac   1260
ttacacttca aacatccttt tgaaagactg acaagtttgg gtcttcacag ttggaattgg   1320
gcatcccttt tgtcagggag ggagggaggg agggaggctg gcttgttatg ctgacaagtg   1380
tgattaaatt caaactttga ggtaagttgg aggaacttgt acattgttag gagtgtgaca   1440
atttggactc ttaatgattt ggtcatacaa aatgaaccta gaccaacttc tggaagatgt   1500
atataataac tccatgttac attgatttca cctgactaat acttatccct tatcaattaa   1560
atacagaaga tgccagccat ctgggccttt taacccagaa atttagtttc aaactcctag   1620
gttagtgttc tcactgagct acatcctgat ctagtcctga aaataggacc accatcaccc   1680
ccaaaaaaat ctcaaataag atttatgcta gtgtttcaaa attttaggaa taggtaagat   1740
tagaaagttt taaattttga gaaatggctt ctctagaaag atgtacatag tgaacactga   1800
atggctccta aagagcctag aaaactggta ctgagcacac aggactgaga ggtctttctt   1860
gaaaagcatg tattgcttta cgtgggtcac agaaggcagg caggaagaac ttgggctgaa   1920
actggtgtct taagtggcta acatcttcac aactgatgag caagaacttt atcctgatgc   1980
aaaaaccatc caaacaaact aagtgaaagg tggcaatgga tcccaggctg ctctagagga   2040
ggacttgact tctcatccca tcacccacac cagatagctc atagactgcc aattaacacc   2100
agcttctagc ctccacaggc acctgcactg gtacacataa tttcacacaa acacagtaag   2160
aagccttcca cctggcatgg tattgcttat ctttagttcc caacacttgg gaggcagagg   2220
ccagccaggg ctatgtgaca aaaaccttgt ctagaggaga aacttcatag cttatttcct   2280
attcacgtaa ccaggttagc aaaatttacc agccagagat gaagctaaca gtgtccacta   2340
tatttgtagt gttttaagtc aattttttaa atatacttaa tagaattaaa gctatggtga   2400
accaagtaca aacctggtgt attaacttga gaacttagca taaaaagtag ttcatttgtt   2460
cagtaaatat taaatgctta ctggcaaaga ttatgtcagg aacttggtaa atggtgatga   2520
aacaatcata gttgtacatc ttggttctgt gatcaccttg gtttgaggta aaagtggttc   2580
ctttgatcaa ggatggaatt ttaagtttat attcaatcaa taatgtatta ttttgtgatt   2640
gcaaaattgc ctatctaggg tataaaacct ttaaaaattt cataataccda gttcattctc   2700
cagttactaa ttccaaaaag ccactgacta tggtgccaat gtggattctg ttctcaaagg   2760
aaggattgtc tgtgcccttt attctaatag aaacatcaca ctgaaaatct aagctgaaag   2820
aagccagact ttcctaaata aataactttc cataaagctc aaacaaggat tacttttagg   2880
aggcactgtt aaggaactga taagtaatga ggttacttat ataatgatag tcccacaaga   2940
ctatctgagg aaaaatcagt acaactcgaa aacagaacaa ccagctaggc aggaataaca   3000
gggctcccaa gtcaggaggt ctatccaaca ccctttctg ttgagggccc cagacctaca   3060
tattgtatac aaacagggag gtgggtgatt ttaactctcc tgaggtac                3108
```

<210> SEQ ID NO 24

<211> LENGTH: 3102
<212> TYPE: DNA
<213> ORGANISM: Artificial Sequence
<220> FEATURE:
<223> OTHER INFORMATION: Sequence of Rosa26 3-prime homology arm

<400> SEQUENCE: 24

| | | | | | |
|---|---|---|---|---|---|
| cttggtaaat | ctttgtcctg | agtaagcagt | acagtgtaca | gtttacattt | tcatttaaag | 60 |
| atacattagc | tccctctacc | ccctaagact | gacaggcact | tgggggtgg | ggagggcttt | 120 |
| ggaaaataac | gcttccatac | actaaaagag | aaatttcttt | aattaggctt | gttggttcca | 180 |
| tacatctact | ggtgtttcta | ctacttagta | atattataat | agtcacacaa | gcatctttgc | 240 |
| tctgtttagg | ttgtatattt | attttaaggc | agatgataaa | actgtagatc | ttaagggatg | 300 |
| cttctgcttc | tgagatgata | caaagaattt | agaccataaa | acagtaggtt | gcacaagcaa | 360 |
| tagaatatgg | cctaaagtgt | tctgacactt | agaagccaag | cagtgtaggc | ttcttaagaa | 420 |
| ataccattac | aatcaccttg | ctagaaatca | agcattctgg | agtggtcaag | cagtgtaacc | 480 |
| tgtactgtaa | gttactttc | tgctattttt | ctcccaaagc | aagttcttta | tgctgatatt | 540 |
| tccagtgtta | ggaactacaa | atattaataa | gttgtcttca | ctcttttctt | taccaaggag | 600 |
| ggtctcttcc | ttcatcttga | tctgaaggat | gaacaaaggc | ttgagcagtg | cgctttagaa | 660 |
| gataaactgc | agcatgaagg | cccccgatgt | tcacccagac | tacatggacc | tttcgccaca | 720 |
| catgtcccat | tccagataag | gcctggcaca | cacaaaaaac | ataagtcatt | aggctaccag | 780 |
| tctgattcta | aaacaaccta | aaatcttccc | acttaaatgc | tatgggtggt | gggttggaaa | 840 |
| gttgactcag | aaaatcactt | gctgttttta | gagaggatct | gggttcagtt | tctgatacat | 900 |
| tgtggcttac | aactataact | ccagttctag | ggggtccatc | caacatcctc | ttctgttgag | 960 |
| ggcaccaaat | aaatgtattg | tgtacaaaca | gggaggtgag | tgatttaact | ctcgtgtata | 1020 |
| gtaccttggt | aaaacatttc | ttgtcctgag | taagcagtac | agctctgcct | gtccctggtc | 1080 |
| tacagacacg | gctcatttcc | cgaaggcaag | ctggatagaa | attccaattt | ctcttcttgg | 1140 |
| atcccatcct | ataaaagaag | gtcaagttta | atctattgca | aaaggtaaat | aggtagtttc | 1200 |
| ttacatgaga | caagaacaaa | tcttaggtgt | gaagcagtca | tcttttacag | gccagagcct | 1260 |
| ctattctatg | ccaatgaagg | aaactgttag | tccagtgtta | tagagttagt | ccagtgtata | 1320 |
| gttttctatc | agaacacttt | ttttttaaac | aactgcaact | tagcttattg | aagcaaaacc | 1380 |
| acgagtagaa | atctgtccaa | gaagcaagtg | cttctcagcc | tacaatgtgg | aataggacca | 1440 |
| tgtaatggta | cagtgagtga | aatgaattat | ggcatgtttt | tctgactgag | aagacagtac | 1500 |
| aataaaaggt | aaactcatgg | tatttattta | aaaagaatcc | aatttctacc | tttttccaaa | 1560 |
| tggcatatct | gttacaataa | tatccacaga | agcagttctc | agtgggaggt | tgcagatatc | 1620 |
| ccactgaaca | gcatcaatgg | gcaaacccca | ggttgttttt | ctgtggagac | aaaggtaaga | 1680 |
| tatttcaata | tattttccca | agctaatgag | atggctcagc | aaataatggt | actggccatt | 1740 |
| aagtctcatg | acctgagctt | gatcctcagg | gaccatgtgg | tacaaggaga | gacctaaatc | 1800 |
| cttcagttgg | acttcaatct | tctaccctca | tgtccacaca | caaataaata | caataaaaaa | 1860 |
| cattctgcag | tctgaatttc | taaggttgt | ttttctaaaa | agaaatgtta | aagtaacata | 1920 |
| ggaagaaata | tgtccataac | tgaaatacaa | gttttttaaa | tggttaagac | tggttttcaa | 1980 |
| aggatgtatg | gttaagaaaa | taccagggaa | aatgagctta | catgtaaaaa | agtgtctaaa | 2040 |
| aggccagaga | aatgacccag | ctggcaaagg | tgtctgccct | aagccagaca | aaaggaattt | 2100 |
| gattcacagg | aagaagagac | ccaactctca | ctagttatcc | tctgacttcc | acaccatgac | 2160 |

```
acagctccat ggcactctca ggcccccaca catatacaga tataaacaga aacctaatcc    2220
accagccttc agaagcaaag caattggagg atttaaacag gccatggcta ctaatagaga    2280
taactggtag tttaaaagtt atggtaatga cttt catgct tctttcaact catattgttc   2340
taaataatta atttggtttt tcaaggcagg gtttctctgt gtagttctgg ctgtcctgga    2400
actcactctg tagaccaggc tggccttgaa ctcagatcca tctgcctctg gaataagggc    2460
acgtgcgtgc cttttctaca taacaaaacc tatactataa caaaacctat accatactgt    2520
accgttttgg gaaaagacaa aaaataatga acaaaaaagg agaaataaca ttccaataaa    2580
gtatggaaat ggtagttaaa ttaattacaa atgttttttca gtaaattaga tgtgacttct    2640
catactgttc atttggctat aatgatacca caaagcactg ggggtgaata ataattccaa    2700
gtcagtaggg agagagactt gaaaagatgc aatgcaatca ttgaagttaa acttaccccat   2760 cttt aatctg gctcttagtc aatagagatg agatgttatt tgctgctctg ttcactgcca   2820
gtgggttatt gtccccagca atatggtaac agtgagacca ctcagtagcc ccctatgaga    2880
caggagtgtt ggttaaacat gccacaagag aaaagggaaa agtcactatg gccaactctc    2940
agtaacatgg caatccgtgc cattcatttc cttgccagaa atgtcttccc tgttcttctg     3000
cctactgaac tttcacccac tagaaatgtg gctccaatgt catccactat gacatcaatg    3060
tcagcgctag aagcactttg cacacctctg ttgctgactt ag                       3102

<210> SEQ ID NO 25
<211> LENGTH: 30
<212> TYPE: DNA
<213> ORGANISM: Artificial Sequence
<220> FEATURE:
<223> OTHER INFORMATION: CRISPR consensus sequence of Genome Mth and PaM
      NGG

<400> SEQUENCE: 25
atttcaatcc cattttggtc tgattttaac                                       30

<210> SEQ ID NO 26
<211> LENGTH: 29
<212> TYPE: DNA
<213> ORGANISM: Artificial Sequence
<220> FEATURE:
<223> OTHER INFORMATION: CRISPR consensus sequence of Genome Lmo and PaM
      WGG

<400> SEQUENCE: 26
atttacattt cahaataagt arytaaaac                                       29

<210> SEQ ID NO 27
<211> LENGTH: 29
<212> TYPE: DNA
<213> ORGANISM: Artificial Sequence
<220> FEATURE:
<223> OTHER INFORMATION: CRISPR consensus sequence of Genome Eco and PaM
      CWT

<400> SEQUENCE: 27
cggtttatcc ccgctggcgc ggggaacwc                                       29

<210> SEQ ID NO 28
<211> LENGTH: 29
<212> TYPE: DNA
<213> ORGANISM: Artificial Sequence
<220> FEATURE:
<223> OTHER INFORMATION: CRISPR consensus sequence of Genome Pae and PaM
```

CTT

<210> SEQ ID NO 28
<211> LENGTH: 29
<212> TYPE: DNA
<213> ORGANISM: Artificial Sequence
<220> FEATURE:
<223> OTHER INFORMATION: CRISPR consensus sequence of Genome Spy and PaM
    GAA

<400> SEQUENCE: 28
cggttcatcc ccacrcmygt ggggaacac                                        29

<210> SEQ ID NO 29
<211> LENGTH: 32
<212> TYPE: DNA
<213> ORGANISM: Artificial Sequence
<220> FEATURE:
<223> OTHER INFORMATION: CRISPR consensus sequence of Genome Spy and PaM
    GAA

<400> SEQUENCE: 29
atttcaatcc actcacccat gaagggtgag ac                                    32

<210> SEQ ID NO 30
<211> LENGTH: 31
<212> TYPE: DNA
<213> ORGANISM: Artificial Sequence
<220> FEATURE:
<223> OTHER INFORMATION: CRISPR consensus sequence of Genome Xan and PaM
    WGG

<400> SEQUENCE: 30
gtttcaatcc acgcgcccgt gaggrcgcga c                                     31

<210> SEQ ID NO 31
<211> LENGTH: 28
<212> TYPE: DNA
<213> ORGANISM: Artificial Sequence
<220> FEATURE:
<223> OTHER INFORMATION: CRISPR consensus sequence of Genome She and PaM
    GG

<400> SEQUENCE: 31
tttctaagcc gcctgtgcgg cggtgaac                                         28

<210> SEQ ID NO 32
<211> LENGTH: 28
<212> TYPE: DNA
<213> ORGANISM: Artificial Sequence
<220> FEATURE:
<223> OTHER INFORMATION: CRISPR consensus sequence of Genome Pae and PaM
    GG

<400> SEQUENCE: 32
tttcttagct gcctatacgg cagtgaac                                         28

<210> SEQ ID NO 33
<211> LENGTH: 28
<212> TYPE: DNA
<213> ORGANISM: Artificial Sequence
<220> FEATURE:
<223> OTHER INFORMATION: CRISPR consensus sequence of Genome Ype and PaM
    GG

<400> SEQUENCE: 33
tttctaagct gcctgtgcgg cagtgaac                                         28

<210> SEQ ID NO 34
<211> LENGTH: 24
<212> TYPE: DNA
<213> ORGANISM: Artificial Sequence
<220> FEATURE:
<223> OTHER INFORMATION: CRISPR consensus sequence of Genome Sso and PaM
    NGG

```
<400> SEQUENCE: 34
ctttcaattc tataagagat tatc                                              24

<210> SEQ ID NO 35
<211> LENGTH: 24
<212> TYPE: DNA
<213> ORGANISM: Artificial Sequence
<220> FEATURE:
<223> OTHER INFORMATION: CRISPR consensus sequence of Genome Mse and PaM
      NGG

<400> SEQUENCE: 35
ctttcaactc tataggagat taac                                              24

<210> SEQ ID NO 36
<211> LENGTH: 36
<212> TYPE: DNA
<213> ORGANISM: Artificial Sequence
<220> FEATURE:
<223> OTHER INFORMATION: CRISPR consensus sequence of Genome Str and PaM
      NGG

<400> SEQUENCE: 36
gttttagagc tatgctgttt tgaatggtcc caaaac                                 36

<210> SEQ ID NO 37
<211> LENGTH: 36
<212> TYPE: DNA
<213> ORGANISM: Artificial Sequence
<220> FEATURE:
<223> OTHER INFORMATION: CRISPR consensus sequence of Genome Lis and PaM
      NGG

<400> SEQUENCE: 37
gttttagagc tatgttattt tgaatgctam caaaac                                 36

<210> SEQ ID NO 38
<211> LENGTH: 10
<212> TYPE: DNA
<213> ORGANISM: Artificial Sequence
<220> FEATURE:
<223> OTHER INFORMATION: Leader

<400> SEQUENCE: 38
agggcggatt                                                              10

<210> SEQ ID NO 39
<211> LENGTH: 10
<212> TYPE: DNA
<213> ORGANISM: Artificial Sequence
<220> FEATURE:
<223> OTHER INFORMATION: Leader

<400> SEQUENCE: 39
atggccaatt                                                              10

<210> SEQ ID NO 40
<211> LENGTH: 10
<212> TYPE: DNA
<213> ORGANISM: Artificial Sequence
<220> FEATURE:
<223> OTHER INFORMATION: Leader

<400> SEQUENCE: 40
ccactaactt                                                              10
```

```
<210> SEQ ID NO 41
<211> LENGTH: 10
<212> TYPE: DNA
<213> ORGANISM: Artificial Sequence
<220> FEATURE:
<223> OTHER INFORMATION: Leader

<400> SEQUENCE: 41
ccgctctatt                                                                10

<210> SEQ ID NO 42
<211> LENGTH: 10
<212> TYPE: DNA
<213> ORGANISM: Artificial Sequence
<220> FEATURE:
<223> OTHER INFORMATION: Leader

<400> SEQUENCE: 42
tctaaacata                                                                10

<210> SEQ ID NO 43
<211> LENGTH: 10
<212> TYPE: DNA
<213> ORGANISM: Artificial Sequence
<220> FEATURE:
<223> OTHER INFORMATION: Leader

<400> SEQUENCE: 43
tctaaaagta                                                                10

<210> SEQ ID NO 44
<211> LENGTH: 10
<212> TYPE: DNA
<213> ORGANISM: Artificial Sequence
<220> FEATURE:
<223> OTHER INFORMATION: Leader

<400> SEQUENCE: 44
acttaccgta                                                                10

<210> SEQ ID NO 45
<211> LENGTH: 10
<212> TYPE: DNA
<213> ORGANISM: Artificial Sequence
<220> FEATURE:
<223> OTHER INFORMATION: Leader

<400> SEQUENCE: 45
ccttaccgta                                                                10

<210> SEQ ID NO 46
<211> LENGTH: 10
<212> TYPE: DNA
<213> ORGANISM: Artificial Sequence
<220> FEATURE:
<223> OTHER INFORMATION: Leader

<400> SEQUENCE: 46
tgcgccaaat                                                                10

<210> SEQ ID NO 47
<211> LENGTH: 10
<212> TYPE: DNA
<213> ORGANISM: Artificial Sequence
<220> FEATURE:
```

<223> OTHER INFORMATION: Leader

<400> SEQUENCE: 47 cccccccttag                                                          10

<210> SEQ ID NO 48
<211> LENGTH: 10
<212> TYPE: DNA
<213> ORGANISM: Artificial Sequence
<220> FEATURE:
<223> OTHER INFORMATION: Leader

<400> SEQUENCE: 48
gccgccagca                                                           10

<210> SEQ ID NO 49
<211> LENGTH: 10
<212> TYPE: DNA
<213> ORGANISM: Artificial Sequence
<220> FEATURE:
<223> OTHER INFORMATION: Leader

<400> SEQUENCE: 49
aatagcttat                                                           10

<210> SEQ ID NO 50
<211> LENGTH: 10
<212> TYPE: DNA
<213> ORGANISM: Artificial Sequence
<220> FEATURE:
<223> OTHER INFORMATION: Leader

<400> SEQUENCE: 50
tgtagaataa                                                           10

<210> SEQ ID NO 51
<211> LENGTH: 10
<212> TYPE: DNA
<213> ORGANISM: Artificial Sequence
<220> FEATURE:
<223> OTHER INFORMATION: Leader

<400> SEQUENCE: 51
tagctccgaa                                                           10

<210> SEQ ID NO 52
<211> LENGTH: 10
<212> TYPE: DNA
<213> ORGANISM: Artificial Sequence
<220> FEATURE:
<223> OTHER INFORMATION: Leader

<400> SEQUENCE: 52
tagaccaaaa                                                           10

<210> SEQ ID NO 53
<211> LENGTH: 10
<212> TYPE: DNA
<213> ORGANISM: Artificial Sequence
<220> FEATURE:
<223> OTHER INFORMATION: Leader

<400> SEQUENCE: 53
gtaagataat                                                           10

```
<210> SEQ ID NO 54
<211> LENGTH: 10
<212> TYPE: DNA
<213> ORGANISM: Artificial Sequence
<220> FEATURE:
<223> OTHER INFORMATION: Leader

<400> SEQUENCE: 54
tgagggttta                                                              10

<210> SEQ ID NO 55
<211> LENGTH: 10
<212> TYPE: DNA
<213> ORGANISM: Artificial Sequence
<220> FEATURE:
<223> OTHER INFORMATION: Leader

<400> SEQUENCE: 55
tgataccttt                                                              10

<210> SEQ ID NO 56
<211> LENGTH: 10
<212> TYPE: DNA
<213> ORGANISM: Artificial Sequence
<220> FEATURE:
<223> OTHER INFORMATION: Leader

<400> SEQUENCE: 56
tgaaactttt                                                              10

<210> SEQ ID NO 57
<211> LENGTH: 10
<212> TYPE: DNA
<213> ORGANISM: Artificial Sequence
<220> FEATURE:
<223> OTHER INFORMATION: Leader

<400> SEQUENCE: 57
tgacactctt                                                              10

<210> SEQ ID NO 58
<211> LENGTH: 10
<212> TYPE: DNA
<213> ORGANISM: Artificial Sequence
<220> FEATURE:
<223> OTHER INFORMATION: Leader

<400> SEQUENCE: 58
ctcgtagact                                                              10

<210> SEQ ID NO 59
<211> LENGTH: 10
<212> TYPE: DNA
<213> ORGANISM: Artificial Sequence
<220> FEATURE:
<223> OTHER INFORMATION: Leader

<400> SEQUENCE: 59
ctcgtagaaa                                                              10

<210> SEQ ID NO 60
<211> LENGTH: 10
<212> TYPE: DNA
<213> ORGANISM: Artificial Sequence
<220> FEATURE:
<223> OTHER INFORMATION: Leader
```

```
<400> SEQUENCE: 60
ctcgcagaat                                                                10

<210> SEQ ID NO 61
<211> LENGTH: 10
<212> TYPE: DNA
<213> ORGANISM: Artificial Sequence
<220> FEATURE:
<223> OTHER INFORMATION: Leader

<400> SEQUENCE: 61
ctcgtagaat                                                                10
```

METHODS, CELLS AND ORGANISMS

CROSS-REFERENCE TO RELATED APPLICATIONS

This application is a continuation application under 35 U.S.C. § 120 of co-pending U.S. application Ser. No. 15/094,624, filed Apr. 8, 2016, which is a continuation of U.S. application Ser. No. 14/490,549, filed Sep. 18, 2014, which claims the benefit of Great Britain application number 1321210.5, filed Dec. 2, 2013, and Great Britain application number 1316560.0, filed Sep. 18, 2013, the disclosures of which are herein incorporated by reference in their entireties.

SEQUENCE LISTING

The content of the following submission on ASCII text file is incorporated herein by reference in its entirety: a computer readable form (CRF) of the Sequence Listing (file name: Sequence_Listing_14490549.txt, created on Apr. 8, 2016, size: 27,892 bytes).

FIELD OF THE INVENTION

The inventors have devised an approach for introducing one or more desired insertions and/or deletions of known sizes into one or more predefined locations in a nucleic acid (eg, in a cell or organism genome). They developed techniques to do this either in a sequential fashion or by inserting a discrete DNA fragment of defined size into the genome precisely in a predefined location or carrying out a discrete deletion of a defined size at a precise location. The technique is based on the observation that DNA single-stranded breaks are preferentially repaired through the HDR pathway, and this reduces the chances of indels (eg, produced by NHEJ) in the present invention and thus is more efficient than prior art techniques.

The inventors have also devised new techniques termed sequential endonuclease-mediated homology directed recombination (sEHDR) and sequential Cas-mediated homology directed recombination (sCHDR).

BACKGROUND

Certain bacterial and archaea strains have been shown to contain highly evolved adaptive immune defence systems, CRISPR/Cas systems, which continually undergo reprogramming to direct degradation of complementary sequences present within invading viral or plasmid DNA. Short segments of foreign DNA, called spacers, are incorporated into the genome between CRISPR repeats, and serve as a 'memory' of past exposures. CRISPR spacers are then used to recognize and silence exogenous genetic elements in a manner analogous to RNAi in eukaryotic organisms. The clustered regularly interspaced short palindromic repeats (CRISPR) system including the CRISPR associated (Cas) protein has been reconstituted in vitro by a number of research groups allowing for the DNA cleavage of almost any DNA template without the caveat of searching for the right restriction enzyme cutter. The CRISPR/Cas system also offers a blunt end cleavage creating a dsDNA or, using mutated Cas versions, a selective single strand-specific cleavage (see Cong et al, Wang et al & Mali et al cited below).

Through in vitro studies using *Streptococcus pyogenes* type II CRISPR/Cas system it has been shown that the only components required for efficient CRISPR/Cas-mediated target DNA or genome modification are a Cas nuclease (eg, a Cas9 nuclease), CRISPR RNA (crRNA) and trans-activating crRNA (tracrRNA). The wild-type mechanism of CRISPR/Cas-mediated DNA cleavage occurs via several steps. Transcription of the CRISPR array, containing small fragments (20-30 base-pairs) of the encountered (or target) DNA, into pre-crRNA, which undergoes maturation through the hybridisation with tracrRNA via direct repeats of pre-crRNA. The hybridisation of the pre-crRNA and tracrRNA, known as guide RNA (gRNA or sgRNA), associates with the Cas nuclease forming a ribonucleoprotein complex, which mediates conversion of pre-crRNA into mature crRNA. Mature crRNA:tracrRNA duplex directs Cas9 to the DNA target consisting of the protospacer and the requisite protospacer adjacent motif (CRISPR/cas protospacer-adjacent motif; PAM) via heteroduplex formation between the spacer region of the crRNA and the protospacer DNA on the host genome. The Cas9 nuclease mediates cleavage of the target DNA upstream of PAM to create a double-stranded break within the protospacer or a strand-specific nick using mutated Cas9 nuclease whereby one DNA strand-specific cleavage motif is mutated (For example, Cas9 nickase contains a D10A substitution) (Cong et al).

It is worth noting that different strains of *Streptococcus* have been isolated which use PAM sequences that are different from that used by *Streptococcus pyogenes* Cas9. The latter requires a NGG PAM sequence. CRISPR/Cas systems (for example the Csy4 endoribonulcease in *Pseudomonas aeroginosa* (see Shah et al)) have been described in other prokaryotic species, which recognise a different PAM sequence (eg, CCN, TCN, TTC, AWG, CC, NNAGNN, NGG, NGGNG). It is noteworthy that the Csy4 (also known as Cas6f) has no sequence homology to Cas9 but the DNA cleavage occurs through a similar mechanism involving the assembly of a Cas-protein-crRNA complex that facilitates target DNA recognition leading to specific DNA cleavage (Haurwitz et al).

In vitro-reconstituted type II CRISPR/Cas system has been adapted and applied in a number of different settings. These include creating selective gene disruption in single or multiple genes in ES cells and also single or multiple gene disruption using a one-step approach using zygotes to generate biallelic mutations in mice. The speed, accuracy and the efficiency at which this system could be applied to genome editing in addition to its multiplexing capability makes this system vastly superior to its predecessor genome editing technologies namely zinc finger nucleases (ZFNs), transcription activator-like effector nucleases (TALENs) and engineered homing meganucleases (Gaj et al & Perez-Pinera et al). These have been successfully used in various eukaryotic hosts but they all suffer from important limitations notably off-target mutagenesis leading to nuclease-related toxicity and also the time and cost of developing such engineered proteins. The CRISPR/Cas system on the other hand is a superior genome editing system by which mutations can be introduced with relative ease simply by designing a single guided RNA complementary to the protospacer sequence on the target DNA.

The dsDNA break induced by an endonuclease, such as Cas9, is subsequently repaired through non-homologous end joining mechanism (NHEJ) whereby the subsequent DNA repair at the breakpoint junction is stitched together with different and unpredictable inserted or deletions (indels) of varying size. This is highly undesirable when precise nucleic acid or genome editing is required. However a predefined precise mutation can be generated using homology directed repair (HDR), eg, with the inclusion of a donor oligo or donor DNA fragment. This approach with Cas9 nuclease has been shown to generate precise predefined mutations but the efficiency at which this occurs in both alleles is low and mutation is seen in one of the strands of the dsDNA target (Wang et al).

The CRISPR/Cas system does therefore have some limitations in its current form. While it may be possible to modify a desired sequence in one strand of dsDNA, the sequence in the other strand is often mutated through undesirable NHEJ.

SUMMARY OF THE INVENTION

A First Configuration of the Present Invention Provides:

A method of nucleic acid recombination, the method comprising providing dsDNA comprising first and second strands and
- (a) using nucleic acid cleavage to create 5' and 3' cut ends in the first strand;
- (b) using homologous recombination to insert a nucleotide sequence between the ends, thereby producing a modified first strand; thereby producing DNA wherein the first strand has been modified by said recombination but the second strand has not been modified; and
- (c) optionally replicating the modified first strand to produce a progeny dsDNA wherein each strand thereof comprises a copy of the inserted nucleotide sequence; and isolating the progeny dsDNA.

A Second Configuration of the Present Invention Provides:

A method of nucleic acid recombination, the method comprising
- (a) using nucleic acid cleavage to create 5' and 3' cut ends in a single nucleic acid strand;
- (b) using homologous recombination to insert a nucleotide sequence between the ends, wherein the insert sequence comprises a regulatory element or encodes all or part of a protein; and
- (c) optionally obtaining the nucleic acid strand modified in step (b) or a progeny nucleic strand comprising the inserted nucleotide sequence.

A Third Configuration of the Present Invention Provides:

A method of nucleic acid recombination, the method comprising
- (a) using nucleic acid cleavage to create first and second breaks in a nucleic acid strand, thereby creating 5' and 3' cut ends and a nucleotide sequence between the ends;
- (b) using homologous recombination to delete the nucleotide sequence; and
- (c) optionally obtaining the nucleic acid strand modified in step (b) or a progeny nucleic strand comprising the deletion.

In aspects of the configurations of the invention there is provided a method of sequential endonuclease-mediated homology directed recombination (sEHDR) comprising carrying out the method of any preceding configuration a first time and carrying out the method of any preceding configuration a second time. In this way, the invention enables serial nucleic acid modifications, e.g., genome modifications, to be carried out, which may comprise precise sequence deletions, insertions or combinations of these two or more times. For example, it is possible to use this aspect of the invention to "walk along" nucleic acids (e.g., chromosomes in cells) to make relatively large and precise nucleotide sequence deletions or insertions. In an embodiment, one or more Cas endonucleases (e.g., a Cas9 and/or Cys4) are used in a method of sequential Cas-mediated homology directed recombination (sCHDR).

In another aspect, the invention can be described according to the numbered sentences below:

1. A method of nucleic acid recombination, the method comprising providing dsDNA comprising first and second strands and
   - (a) using nucleic acid cleavage to create 5' and 3' cut ends in the first strand;
   - (b) using homologous recombination to insert a nucleotide sequence between the ends, thereby producing a modified first strand; thereby producing DNA wherein the first strand has been modified by said recombination but the second strand has not been modified; and
   - (c) optionally replicating the modified first strand to produce a progeny dsDNA wherein each strand thereof comprises a copy of the inserted nucleotide sequence; and isolating the progeny dsDNA.
2. A method of nucleic acid recombination, the method comprising
   - (a) using nucleic acid cleavage to create 5' and 3' cut ends in a single nucleic acid strand;
   - (b) using homologous recombination to insert a nucleotide sequence between the ends, wherein the insert sequence comprises a regulatory element or encodes all or part of a protein; and
   - (c) optionally obtaining the nucleic acid strand modified in step (b) or a progeny nucleic strand comprising the inserted nucleotide sequence.
3. The method of any preceding sentence, wherein the insert sequence replaces an orthologous or homologous sequence of the strand.
4. The method of any preceding sentence, wherein the insert nucleotide sequence is at least 10 nucleotides long.
5. The method of any preceding sentence, wherein the insert sequence comprises a site specific recombination site.
6. A method of nucleic acid recombination, the method comprising
   - (a) using nucleic acid cleavage to create first and second breaks in a nucleic acid strand, thereby creating 5' and 3' cut ends and a nucleotide sequence between the ends;
   - (b) using homologous recombination to delete the nucleotide sequence; and
   - (c) optionally obtaining the nucleic acid strand modified in step (b) or a progeny nucleic strand comprising the deletion.
7. The method of sentence 6, wherein the deleted sequence comprises a regulatory element or encodes all or part of a protein.
8. The method of any preceding sentence, wherein step (c) is performed by isolating a cell comprising the modified first strand, or by obtaining a non-human vertebrate in which the method has been performed or a progeny thereof.
9. The method of any preceding sentence, wherein the nucleic acid strand or the first strand is a DNA strand.
10. The method of any preceding sentence wherein the product of the method comprises a nucleic acid strand comprising a PAM motif 3' of the insertion or deletion.
11. The method of any preceding sentence, wherein step (b) is performed by carrying out homologous recombination between an incoming nucleic acid comprising first and second homology arms, wherein the homology arms are substantially homologous respectively to a sequence extending 5' from the 5' end and a sequence extending 3' from the 3' end.

12. The method of sentence 11, wherein step (b) is performed by carrying out homologous recombination between an incoming nucleic acid comprising an insert nucleotide sequence flanked by the first and second homology arms, wherein the insert nucleotide sequence is inserted between the 5' and 3' ends.

13. The method of sentence 12, wherein the insert is as recited in any one of sentences 3 to 5 and there is no further sequence between the homology arms.

14. The method of any one of sentences 11 to 13, wherein each homology arm is at least 20 contiguous nucleotides long.

15. The method of any one of sentences 11 to 14, wherein the first and/or second homology arm comprises a PAM motif.

16. The method of any preceding sentence, wherein Cas endonuclease-mediated cleavage is used in step (a); optionally by recognition of a GG or NGG PAM motif.

17. The method of sentence 16, wherein a nickase is used to cut in step (a).

18. The method of any preceding sentence, wherein the method is carried out in a cell, e.g., a eukaryotic cell.

19. The method of sentence 19, wherein the method is carried out in a mammalian cell. 20. The method of sentence 19, wherein the cell is a rodent (e.g., mouse) ES cell or zygote. 21. The method of any preceding sentence, wherein the method is carried out in a non-human mammal, e.g., a mouse or rat or rabbit.

22. The method of any preceding sentence, wherein each cleavage site is flanked by PAM motif (e.g., a NGG or NGGNG sequence, wherein N is any base and G is a guanine).

23. The method of any preceding sentence, wherein the 3' end is flanked 3' by a PAM motif.

24. The method of any preceding sentence, wherein step (a) is carried out by cleavage in one single strand of dsDNA.

25. The method of any preceding sentence, wherein step (a) is carried out by combining in a cell the nucleic acid strand, a Cas endonuclease, a crRNA and a tracrRNA (e.g., provided by one or more gRNAs) for targeting the endonuclease to carry out the cleavage, and optionally an insert sequence for homologous recombination with the nucleic acid strand.

26. The method of any preceding sentence, wherein step (b) is performed by carrying out homologous recombination with an incoming nucleic acid comprising first and second homology arms, wherein the homology arms are substantially homologous respectively to a sequence extending 5' from the 5' end and a sequence extending 3' from the 3' end, wherein the second homology arm comprises a PAM sequence such that homologous recombination between the second homology arm and the sequence extending 3' from the 3' end produces a sequence comprising a PAM motif in the product of the method.

27. A method of sequential endonuclease-mediated homology directed recombination (sEHDR) comprising carrying out the method of any preceding sentence (e.g., when according to sentence 1 using a nickase to cut a single strand of dsDNA; or when dependent from sentence 2 or 5 using a nuclease to cut both strands of dsDNA) a first time and a second time, wherein endonuclease-mediated cleavage is used in each step (a); wherein the product of the first time is used for endonuclease-mediated cleavage the second time, whereby either (i) first and second nucleotide sequences are deleted the first time and the second times respectively; (ii) a first nucleotide sequence is deleted the first time and a second nucleotide sequence is inserted the second time; (iii) a first nucleotide sequence is inserted the first time and a second nucleotide sequence is deleted the second time; or (iv) first and second nucleotide sequences are inserted the first and second times respectively; optionally wherein the nucleic acid strand modification the second time is within 20 or less nucleotides of the nucleic acid strand modification the first time.

28. The method of sentence 27, wherein the first time is carried out according to sentence 6, wherein the incoming nucleic acid comprises no sequence between the first and second homology arms, wherein sequence between the 5' and 3' ends is deleted by homologous recombination; and/or the second time is carried out according to sentence 6, wherein step (b) is performed by carrying out homologous recombination between an incoming nucleic acid comprising first and second homology arms, wherein the homology arms are substantially homologous respectively to a sequence extending 5' from the 5' end and a sequence extending 3' from the 3' end, wherein the incoming nucleic acid comprises no sequence between the first and second homology arms such that sequence between the 5' and 3' ends is deleted by homologous recombination; optionally wherein the second arm comprises a PAM motif such that the product of the second time comprises a PAM motif for use in a subsequent Cas endonuclease-mediated method according to any one of sentences 1 to 26.

29. The method of sentence 27, wherein the first time is carried out according to sentence 1 or 2, wherein the incoming nucleic acid comprises the insert sequence between the first and second homology arms, wherein the insert sequence is inserted between the 5' and 3' ends by homologous recombination; and/or the second time is carried out according to sentence 1 or 2, wherein step (b) is performed by carrying out homologous recombination between an incoming nucleic acid comprising first and second homology arms, wherein the homology arms are substantially homologous respectively to a sequence extending 5' from the 5' end and a sequence extending 3' from the 3' end, wherein the insert sequence is inserted between the 5' and 3' ends by homologous recombination; optionally wherein the second arm comprises a PAM motif such that the product of the second time comprises a PAM motif for use in a subsequent Cas endonuclease-mediated method according to any one of sentences 1 to 26.

30. The method of sentence 27, wherein one of said first and second times is carried out as specified in sentence 28 and the other time is carried out as specified in sentence 29, wherein at least one sequence deletion and at least one sequence insertion is performed.

31. The method of any preceding sentence, wherein step (a) is carried out using Cas endonuclease-mediated cleavage and a gRNA comprising a crRNA and a tracrRNA.

32. The method of sentence 25 or 31, wherein the crRNA has the structure 5'-X-Y-3', wherein X is an RNA nucleotide sequence (optionally at least 5 nucleotides long) and Y is a crRNA sequence comprising a nucleotide motif that hybridises with a motif comprised by the tracrRNA, wherein X is capable of hybridising with a nucleotide sequence extending 5' from the desired site of the 5' cut end.

33. The method of sentence 25, 31 or 32, wherein Y is 5'-N1UUUUAN2N3GCUA-3' (SEQ ID NO: 3), wherein each of N1-3 is a A, U, C or G and/or the tracrRNA comprises the sequence (in 5' to 3' orientation) UAGCM1UUAAAAM2 (SEQ ID NO: 4), wherein M1 is spacer nucleotide sequence and M2 is a nucleotide.

34. A method of producing a cell or a transgenic non-human organism, the method comprising (a) carrying out the method of any preceding sentence to
  (i) knock out a target nucleotide sequence in the
  genome of a first cell and/or (ii) knock in an insert
  nucleotide sequence into the genome of a first cell,
  optionally wherein the insert sequence replaces a target
  sequence in whole or in part at the endogenous location
  of the target sequence in the genome; wherein the cell
  or a progeny thereof can develop into a non-human
  organism or cell; and
(b) developing the cell or progeny into a non-human
  organism or a non-human cell.

35. The method of sentence 34, wherein the organism or cell is homozygous for the modification (i) and/or (ii).

36. The method of sentence 34 or 35, wherein the cell is an ES cell, iPS cell, totipotent cell or pluripotent cell.

37. The method of any one of sentences 34 to 36, wherein the cell is a rodent (e.g., a mouse or rat) cell.

38. The method of any one of sentences 34 to 37, wherein the target sequence is an endogenous sequence comprising all or part of a regulatory element or encoding all or part of a protein.

39. The method of any one of sentences 34 to 38, wherein the insert sequence is a synthetic sequence; or comprises a sequence encoding all or part of a protein from a species other than the species from which the first cell is derived; or comprises a regulatory element from said first species.

40. The method of sentence 39, wherein the insert sequence encodes all or part of a human protein or a human protein subunit or domain.

41. A cell or a non-human organism whose genome comprises a modification comprising a non-endogenous nucleotide sequence flanked by endogenous nucleotide sequences, wherein the cell or organism is obtainable by the method of any one of sentences 24 to 40 and wherein the non-endogenous sequence is flanked 3' by a Cas PAM motif; wherein the cell is not comprised by a human; and one, more or all of (a) to (d) applies
  (a) the genome is homozygous for the modification; or comprises the modification at one allele and is unmodified by Cas-mediated homologous recombination at the other allele;
  (b) the non-endogenous sequence comprises all or part of a regulatory element or encodes all or part of a protein;
  (c) the non-endogenous sequence is at least 20 nucleotides long;
  (d) the non-endogenous sequence replaces an orthologous or homologous sequence in the genome.

42. The cell or organism of sentence 41, wherein the non-endogenous sequence is a human sequence.

43. The cell or organism of sentence 41 or 42, wherein the PAM motif comprises a sequence selected from CCN, TCN, TTC, AWG, CC, NNAGNN, NGGNG GG, NGG, WGG, CWT, CTT and GAA.

44. The cell or organism of any one of sentences 41 to 43, wherein there is a PAM motif no more than 10 nucleotides (e.g., 3 nucleotides) 3' of the non-endogenous sequence.

45. The cell or organism of any one of sentences 41 to 44, wherein the PAM motif is recognised by a *Streptococcus* Cas9.

46. The cell or organism of any one of claims 41 to 45, which is a non-human vertebrate cell or a non-human vertebrate that expresses one or more human antibody heavy chain variable domains (and optionally no heavy chain variable domains of a non-human vertebrate species).

47. The cell or organism of any one of sentences 41 to 46, which is a non-human vertebrate cell or a non-human vertebrate that expresses one or more human antibody kappa light chain variable domains (and optionally no kappa light chain variable domains of a non-human vertebrate species).

48. The cell or organism of any one of sentences 41 to 47, which is a non-human vertebrate cell or a non-human vertebrate that expresses one or more human antibody lambda light chain variable domains (and optionally no kappa light chain variable domains of a non-human vertebrate species).

49. The cell or organism of any one of sentences 46 to 48, wherein the non-endogenous sequence encodes a human Fc receptor protein or subunit or domain thereof (e.g., a human FcRn or Ed receptor protein, subunit or domain).

50. The cell or organism of any one of sentences 41 to 48, wherein the non-endogenous sequence comprises one or more human antibody gene segments, an antibody variable region or an antibody constant region.

51. The cell or organism of any one of sentences 41 to 50, wherein the insert sequence is a human sequence that replaces or supplements an orthologous non-human sequence.

52. A monoclonal or polyclonal antibody prepared by immunisation of a vertebrate (e.g., mouse or rat) according to any one of sentences 41 to 51 with an antigen.

53. A method of isolating an antibody that binds a predetermined antigen, the method comprising
  (a) providing a vertebrate (optionally a mouse or rat) according to any one of sentences 41 to 51;
  (b) immunising said vertebrate with said antigen;
  (c) removing B lymphocytes from the vertebrate and selecting one or more B lymphocytes expressing antibodies that bind to the antigen;
  (d) optionally immortalizing said selected B lymphocytes or progeny thereof, optionally by producing hybridomas therefrom; and
  (e) isolating an antibody (e.g., and IgG-type antibody) expressed by the B lymphocytes.

54. The method of sentence 53, comprising the step of isolating from said B lymphocytes nucleic acid encoding said antibody that binds said antigen; optionally exchanging the heavy chain constant region nucleotide sequence of the antibody with a nucleotide sequence encoding a human or humanised heavy chain constant region and optionally affinity maturing the variable region of said antibody; and optionally inserting said nucleic acid into an expression vector and optionally a host.

55. The method of sentence 53 or 54, further comprising making a mutant or derivative of the antibody produced by the method of sentence 53 or 54.

56. The use of an isolated, monoclonal or polyclonal antibody according to sentence 52, or a mutant or derivative antibody thereof that binds said antigen, in the manufacture of a composition for use as a medicament.

57. The use of an isolated, monoclonal or polyclonal antibody according to sentence 52, or a mutant or derivative antibody thereof that binds said antigen for use in medicine.

58. A nucleotide sequence encoding an antibody of sentence 52, optionally wherein the nucleotide sequence is part of a vector.

59. A pharmaceutical composition comprising the antibody or antibodies of sentence 52 and a diluent, excipient or carrier.

60. An ES cell, a eukaryotic cell, a mammalian cell, a non-human animal or a non-human blastocyst comprising an expressible genomically-integrated nucleotide sequence encoding a Cas endonuclease.

61. The cell, animal or blastocyst of sentence 60, wherein the endonuclease sequence is constitutively expressible.

62. The cell, animal or blastocyst of sentence 60, wherein the endonuclease sequence is inducibly expressible.

63. The cell, animal or blastocyst of sentence 60, 61 or 62, wherein the endonuclease sequence is expressible in a tissue-specific or stage-specific manner in the animal or a progeny thereof, or in a non-human animal that is a progeny of the cell or blastocyst. 64. The cell or animal of sentence 63, wherein the cell is a non-human embryo cell or the animal is a non-human embryo, wherein the endonuclease sequence is expressible or expressed in the cell or embryo.

65. The cell of animal sentence 64, wherein the endonuclease is operatively linked to a promoter selected from the group consisting of an embryo-specific promoter (e.g., a Nanog promoter, a Pou5fl promoter or a SoxB promoter).

66. The cell, animal or blastocyst of any one of sentences 60 to 65, wherein the Cas endonuclease is at a Rosa 26 locus.

67. The cell, animal or blastocyst of any one of sentences 60 to 65, wherein the Cas endonuclease is operably linked to a Rosa 26 promoter.

68. The cell, animal or blastocyst of any one of sentences 60 to 63, wherein the Cas endonuclease sequence is flanked 5' and 3' by transposon elements (e.g., inverted piggyBac terminal elements) or site-specific recombination sites (e.g., loxP and/or a mutant lox, e.g., lox2272 or lox511; or frt).

69. The cell, animal or blastocyst of sentence 68, comprising one or more restriction endonuclease sites between the Cas endonuclease sequence and a transposon element.

70. The cell, animal or blastocyst of any one of sentences 60 to 69 comprising one or more gRNAs.

71. The cell, animal or blastocyst of sentence 68, 69 or 70, wherein the gRNA(s) are flanked 5' and 3' by transposon elements (e.g., inverted piggyBac terminal elements) or site-specific recombination sites (e.g., loxP and/or a mutant lox, e.g., lox2272 or lox511; or frt).

72. Use of the cell, animal or blastocyst of any one of sentences 60 to 71 in a method according to any one of sentences 1 to 51.

BRIEF DESCRIPTION OF THE FIGURES

FIG. 1 depicts a schematic of precise DNA Insertion in a Predefined Location (KI). gRNA designed against a predefined location can induce DNA nick using Cas9 D10A nickase 5' of the PAM sequence (shown as solid black box). Alternatively, gRNA can be used together with Cas9 wild-type nuclease to induce double-stranded DNA breaks 5' of the PAM sequence. The addition of a donor oligo or a donor DNA fragment (single or double stranded) with homology around the breakpoint region containing any form of DNA alterations including addition of endogenous or exogenous DNA can be precisely inserted at the breakpoint junction where the DNA is repaired through HDR.

FIG. 2 depicts a schematic of precise DNA Deletion (KO). gRNAs targeting flanking region of interest can induce two DNA nicks using Cas9 D10A nickase in pre-define locations containing the desired PAM sequences (shown as solid black box). Alternatively, gRNAs can be used with Cas9 wild-type nuclease to induce two DSB flanking the region of interest. Addition of a donor oligo or a donor DNA fragment (single or double stranded) with homology to region 5' of PAM 1 and 3' of PAM 2 sequence will guide DNA repair in a precise manner via HDR. DNA repair via HDR will reduce the risk of indel formation at the breakpoint junctions and avoid DNA repair through NHEJ and in doing so, it will delete out the region flanked by the PAM sequence and carry out DNA repair in a pre-determined and pre-defined manner.

FIG. 3 depicts precise DNA Deletion and Insertion (KO→KI). gRNAs targeting flanking region of interest can induce two DNA nicks using Cas9 D10A nickase in pre-define locations containing the desired PAM sequences (shown as solid black box). Alternatively, gRNAs can be used with Cas9 wild-type nuclease to induce two DSB flanking the region of interest. Addition of a donor oligo or a donor DNA fragment (single or double stranded) with homology to region 5' of PAM 1 and 3' to PAM 2 with inclusion of additional endogenous or exogenous DNA, will guide DNA repair in a precise manner via HDR with the concomitant deletion of the region flanked by DSB or nick and the insertion of DNA of interest.

FIG. 4 depicts a schematic of recycling PAM For Sequential Genome Editing (Deletions). gRNAs targeting flanking region of interest can induce two DNA nicks using Cas9 D10A nickase in predefine locations containing the desired PAM sequences (shown as solid black box). Alternatively, gRNAs can be used with Cas9 wild-type nuclease to induce two DSB flanking the region of interest. Addition of a donor oligo or a donor DNA fragment (single or double stranded) with homology to region 5' of PAM 2 and 3' of PAM 3 will guide DNA repair in a precise manner via HDR and in doing so, it will delete out the region between PAM 2 and PAM 3. This deletion will retain PAM 3 and thus acts as a site for carrying out another round of CRISPR/Cas mediated genome editing. Another PAM site (e.g., PAM 1) can be used in conjunction with PAM 3 sequence to carry out another round of deletion as described above. Using this PAM recycling approach, many rounds of deletions can be performed in a stepwise deletion fashion, where PAM 3 is recycled after each round. This approach can be used also for the stepwise addition of endogenous or exogenous DNA.

FIG. 5 depicts CRISPR/Cas mediated Lox Insertion to facilitate RMCE. gRNAs targeting flanking region of interest can induce two DNA nicks using Cas9 D10A nickase in predefine locations containing the desired PAM sequences (shown as solid black box). Alternatively, gRNAs can be used with Cas9 wild-type nuclease to induce two DSB flanking the region of interest. Addition of two donor oligos or donor DNA fragments (single or double stranded) with homology to regions 5' and 3' of each PAM sequence where the donor DNA contains recombinase recognition sequence (RRS) such as loxP and lox5171 will guide DNA repair in a precise manner via HDR with the inclusion of these RRS. The introduced RRS can be used as a landing pad for inserting any DNA of interest with high efficiency and precisely using recombinase mediated cassette exchange (RMCE). The retained PAM 2 site can be recycled for another round of CRISPR/Cas mediated genome editing for deleting or inserting DNA of interest. Note, the inserted DNA of interest could contain selection marker such as PGK-Puro flanked by PiggyBac LTR to allow for the initial selection and upon successful integration into DNA of interest, the selection marker can be removed conveniently by expressing hyperPbase transposase.

DETAILED DESCRIPTION OF THE INVENTION

Figure 6:
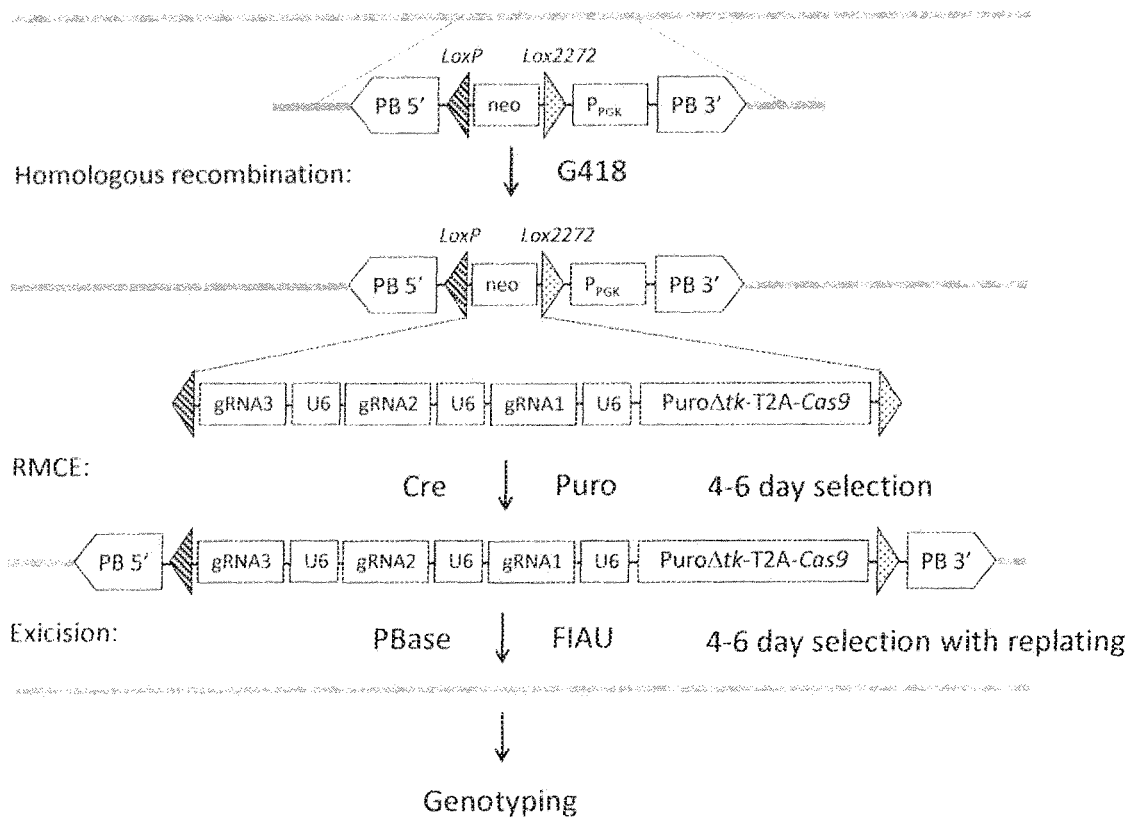
FIG. 6 depicts a schematic of genome modification to produce transposon-excisable Cas9 and gRNA.

The inventors addressed the need for improved nucleic acid modification techniques. An example of a technique for nucleic acid modification is the application of the CRISPR/

Cas system. This system has been shown thus far to be the most advanced genome editing system available due, inter alia, to its broad application, the relative speed at which genomes can be edited to create mutations and its ease of use. The inventors, however, believed that this technology can be advanced for even broader applications than are apparent from the state of the art.

The inventors realised that an important aspect to achieve this would be to find a way of improving the fidelity of nucleic acid modifications beyond that contemplated by the CRISPR/Cas methods known in the art.

Additionally, the inventors realised that only modest nucleic acid modifications had been reported to date. It would be desirable to effect relatively large predefined and precise DNA deletions or insertions using the CRISPR/Cas system.

The inventors have devised an approach for introducing one or more desired insertions and/or deletions of known sizes into one or more predefined locations in a nucleic acid (eg, in a cell or organism genome). They developed techniques to do this either in a sequential fashion or by inserting a discrete DNA fragment of defined size into the genome precisely in a predefined location or carrying out a discrete deletion of a defined size at a precise location. The technique is based on the observation that DNA single-stranded breaks are preferentially repaired through the HDR pathway, and this reduces the chances of indels (eg, produced by NHEJ) in the present invention and thus is more efficient than prior art techniques.

To this end, the invention provides:

A method of nucleic acid recombination, the method comprising providing double stranded DNA (dsDNA) comprising first and second strands and
  (a) using nucleic acid cleavage to create 5' and 3' cut ends in the first strand; and
  (b) using homologous recombination to insert a nucleotide sequence between the ends, thereby producing a modified first strand; thereby producing DNA wherein the first strand has been modified by said recombination but the second strand has not been modified.

Optionally the method further comprises replicating the modified first strand to produce a progeny dsDNA wherein each strand thereof comprises a copy of the insert nucleotide sequence. Optionally the method comprises (c) isolating the progeny dsDNA, eg, by obtaining a cell containing said progeny dsDNA. Replication can be effected, for example in a cell. For example, steps (a) and (b) are carried out in a cell and the cell is replicated, wherein the machinery of the cell replicates the modified first strand, eg, to produce a dsDNA progeny in which each strand comprises the modification.

Optionally, in any configuration, aspect, example or embodiment of the invention, the modified DNA strand resulting from step (b) is isolated.

Optionally, in any configuration, aspect, example or embodiment of the invention, the method is carried out in vitro. For example, the method is carried out in a cell or cell population in vitro.

Alternatively, optionally, in any configuration, aspect, example or embodiment of the invention, the method is carried out to modify the genome of a virus.

Alternatively, optionally, in any configuration, aspect, example or embodiment of the invention, the method is carried out in vivo in an organism. In an example, the organism is a non-human organism. In an example it is a plant or an animal or an insect or a bacterium or a yeast. For example, the method is practised on a vertebrate (eg, a human patient or a non-human vertebrate (e.g., a bird, e.g., a chicken) or non-human mammal such as a mouse, a rat or a rabbit). Optionally, in any configuration, aspect, example or embodiment of the invention, the method is a method of cosmetic treatment of a human or a non-therapeutic, non-surgical, non-diagnostic method, e.g., practised on a human or a non-human vertebrate or mammal (e.g., a mouse or a rat).

The Invention Also Provides:

A method of nucleic acid recombination, the method comprising
  (a) using nucleic acid cleavage to create 5' and 3' cut ends in a single nucleic acid strand;
  (b) using homologous recombination to insert a nucleotide sequence between the ends, wherein the insert sequence comprises a regulatory element or encodes all or part of a protein; and
  (c) Optionally obtaining the nucleic acid strand modified in step (b) or a progeny nucleic strand comprising the inserted nucleotide sequence, eg, by obtaining a cell containing said progeny nucleic acid strand.

In an example the progeny strand is a product of the replication of the strand produced by step (b). The progeny strand is, for example, produced by nucleic acid replication in a cell. For example, steps (a) and (b) are carried out in a cell and the cell is replicated, wherein the machinery of the cell replicates the modified strand produced in step (b), e.g., to produce a dsDNA progeny in which each strand comprises the modification.

In an example, the single nucleic acid strand is a DNA or RNA strand.

In an example, the regulatory element is a promoter or enhancer.

Optionally, in any configuration, aspect, example or embodiment of the invention, the inserted nucleotide sequence is a plant, animal, vertebrate or mammalian sequence, e.g., a human sequence. For example, the sequence encodes a complete protein, polypeptide, peptide, domain or a plurality of any one of these. In an example, the inserted sequence confers a resistance property to a cell comprising the modified nucleic acid produced by the method of the invention (e.g., herbicide, viral or bacterial resistance). In an example, the inserted sequence encodes an interleukin, receptor (e.g., a cell surface receptor), growth factor, hormone, antibody (or variable domain or binding site thereof), antagonist, agonist; eg, a human version of any of these. In an example, the inserted sequence is an exon.

Optionally, in any configuration, aspect, example or embodiment of the invention, the inserted nucleotide sequence replaces an orthologous or homologous sequence of the strand (e.g, the insert is a human sequence that replaces a plant, human or mouse sequence). For example, the method is carried out in a mouse or mouse cell and the insert replaces an orthologous or homologous mouse sequence (e.g., a mouse biological target protein implicated in disease). For example, the method is carried out (e.g., in vitro) in a human cell and the insert replaces an orthologous or homologous human sequence (e.g., a human biological target protein implicated in disease, e.g., a mutated form of a sequence is replaced with a different (e.g., wild-type) human sequence, which may be useful for correcting a gene defect in the cell. In this embodiment, the cell may be a human ES or iPS or totipotent or pluripotent stem cell and may be subsequently introduced into a human patient in a method of gene therapy to treat and/or prevent a medical disease or condition in the patient).

Optionally, in any configuration, aspect, example or embodiment of the invention, the inserted nucleotide sequence is at least 10 nucleotides long, eg, at least 20, 30, 40, 50, 60, 70, 80, 90, 100, 150, 200, 300, 400, 500, 600, 700, 800 or 900 nucleotides, or at least 1, 2, 3, 5, 10, 20, 50 or 100 kb long.

Optionally, in any configuration, aspect, example or embodiment of the invention, the insert sequence comprises a site specific recombination site, eg, a lox, frt or rox site. For example, the site can be a loxP, lox511 or lox2272 site.

The Invention Also Provides:

A method of nucleic acid recombination, the method comprising
(a) using nucleic acid cleavage to create first and second breaks in a nucleic acid strand, thereby creating 5' and 3' cut ends and a nucleotide sequence between the ends;
(b) using homologous recombination to delete the nucleotide sequence; and
(c) optionally obtaining the nucleic acid strand modified in step (b) or a progeny nucleic strand comprising the deletion.

In an example the progeny strand is a product of the replication of the strand produced by step (b). The progeny strand is, for example, produced by nucleic acid replication in a cell. For example, steps (a) and (b) are carried out in a cell and the cell is replicated, wherein the machinery of the cell replicates the modified strand produced in step (b), eg, to produce a dsDNA progeny in which each strand comprises the modification.

In an example, the single nucleic acid strand is a DNA or RNA strand.

In an example, the deleted sequence comprises a regulatory element or encodes all or part of a protein. In an embodiment, the deleted regulatory element is a promoter or enhancer.

Optionally, in any configuration, aspect, example or embodiment of the invention, the deleted nucleotide sequence is a plant, animal, vertebrate or mammalian sequence, e.g., a human sequence. For example, the sequence encodes a complete protein, polypeptide, peptide, domain or a plurality of any one of these. In an example, the deleted sequence encodes an interleukin, receptor (e.g., a cell surface receptor), growth factor, hormone, antibody (or variable domain or binding site thereof), antagonist, agonist; e.g., a non-human version of any of these. In an example, the deleted sequence is an exon.

Optionally, in any configuration, aspect, example or embodiment of the invention, the deleted nucleotide sequence is replaced by an orthologous or homologous sequence of a different species or strain (e.g., a human sequence replaces an orthologous or homologous plant, human or mouse sequence). For example, the method is carried out in a mouse or mouse cell and the insert replaces an orthologous or homologous mouse sequence (e.g., a mouse biological target protein implicated in disease). For example, the method is carried out (e.g., in vitro) in a human cell and the insert replaces an orthologous or homologous human sequence (e.g., a human biological target protein implicated in disease, e.g., a mutated form of a sequence is replaced with a different (e.g., wild-type) human sequence, which may be useful for correcting a gene defect in the cell. In this embodiment, the cell may be a human ES or iPS or totipotent or pluripotent stem cell and may be subsequently introduced into a human patient in a method of gene therapy to treat and/or prevent a medical disease or condition in the patient).

Optionally, in any configuration, aspect, example or embodiment of the invention, the deleted nucleotide sequence is at least 10 nucleotides long, eg, at least 20, 30, 40, 50, 60, 70, 80, 90, 100, 150, 200, 300, 400, 500, 600, 700, 800 or 900 nucleotides, or at least 1, 2, 3, 5, 10, 20, 50 or 100 kb long.

Optionally, in any configuration, aspect, example or embodiment of the invention, step (c) is performed by isolating a cell comprising the modified first strand, or by obtaining a non-human vertebrate in which the method has been performed or a progeny thereof.

Optionally, in any configuration, aspect, example or embodiment of the invention, the product of the method comprises a nucleic acid strand comprising a PAM motif 3' of the insertion or deletion. In an example, the PAM motif is within 10, 9, 8, 7 6, 5, 4 or 3 nucleotides of the insertion or deletion. This is useful to enable serial insertions and/or deletions according to the method as explained further below.

Optionally, in any configuration, aspect, example or embodiment of the invention, the product of the method comprises a nucleic acid strand comprising a PAM motif 5' of the insertion or deletion. In an example, the PAM motif is within 10, 9, 8, 7 6, 5, 4 or 3 nucleotides of the insertion or deletion. This is useful to enable serial insertions and/or deletions according to the method as explained further below.

Optionally, in any configuration, aspect, example or embodiment of the invention, step (b) is performed by carrying out homologous recombination between an incoming nucleic acid comprising first and second homology arms, wherein the homology arms are substantially homologous respectively to a sequence extending 5' from the 5' end and a sequence extending 3' from the 3' end. The skilled person will be familiar with constructing vectors and DNA molecules for use in homologous recombination, including considerations such as homology arm size and sequence and the inclusion of selection markers between the arms. For example, the incoming nucleic acid comprises first and second homology arms, and the insert sequence and an optional selection marker sequence (e.g., neo nucleotide sequence). The arms may be at least 20, 30, 40, 50, 100 or 150 nucleotides in length, for example. Where deletion is required, the insert is omitted (although an optional selection marker sequence may or may not be included between the arms).

Thus, in an embodiment of the invention, step (b) is performed by carrying out homologous recombination between an incoming nucleic acid comprising an insert nucleotide sequence flanked by the first and second homology arms, wherein the insert nucleotide sequence is inserted between the 5' and 3' ends.

In another embodiment of the invention, the insert is between the homology arms and there is no further sequence between the arms.

In an example, each homology arm is at least 20, 30, 40, 50, 100 or 150 nucleotides long.

Optionally, in any configuration, aspect, example or embodiment of the invention, step (a) is carried out using an endonuclease, eg, a nickase. Nickases cut in a single strand of dsDNA only. For example, the endonuclease is an endonuclease of a CRISPR/Cas system, eg, a Cas9 or Cys4 endnonuclease (e.g., a Cas9 or Cys4 nickase). In an example, the endounuclease recognises a PAM listed in Table 1 below, for example, the endonuclease is a Cas endonuclease that recognises a PAM selected from CCN, TCN, TTC, AWG, CC, NNAGNN, NGGNG GG, NGG, WGG, CWT, CTT and GAA. In an example, the Cas endonuclease is a *S pyogenes* endonuclease, e.g., a *S pyo-* genes Cas9 endonuclease. In an example, a *S. pyogenes* PAM sequence or *Streptococcus thermophilus* LMD-9 PAM sequence is used.

In an example, the endonuclease is a Group 1 Cas endonuclease. In an example, the endonuclease is a Group 2 Cas endonuclease. In an example, the endonuclease is a Group 3 Cas endonuclease. In an example, the endonuclease is a Group 4 Cas endonuclease. In an example, the endonuclease is a Group 7 Cas endonuclease. In an example, the endonuclease is a Group 10 Cas endonuclease.

In an example, the endonuclease recognises a CRISPR/Cas Group 1 PAM. In an example, the endonuclease recognises a CRISPR/Cas Group 2 PAM. In an example, the endonuclease recognises a CRISPR/Cas Group 3 PAM. In an example, the endonuclease recognises a CRISPR/Cas Group 4 PAM. In an example, the endonuclease recognises a CRISPR/Cas Group 7 PAM. In an example, the endonuclease recognises a CRISPR/Cas Group 10 PAM.

In an example, Cas endonuclease-mediated cleavage is used in step (a); optionally by recognition of a GG or NGG PAM motif.

In an example, the first and/or second homology arm comprises a PAM motif. This is useful to enable serial insertions and/or deletions according to the method as explained further below.

An example of a suitable nickase is *S pyogenes* Cas9 D10A nickase (see Cong et al and the Examples section below).

Optionally, in any configuration, aspect, example or embodiment of the invention, steps (a) and (b) of the method is carried out in a cell, eg a bacterial, yeast, eukaryotic cell, plant, animal, mammal, vertebrate, non-human animal, rodent, rat, mouse, rabbit, fish, bird or chicken cell. For example, the cell is an *E coli* cell or CHO or HEK293 or *Picchia* or *Saccharomyces* cell. In an example, the cell is a human cell in vitro. In one embodiment, the cell is an embryonic stem cell (ES cell, e.g., a human or non-human ES cell) or an induced pluripotent stem cell (iPS cell; e.g., a human, rodent, rat or mouse iPS cell) or a pluripotent or totipotent cell. Optionally the cell is not an embryonic cell, e.g., wherein the cell is not a human embryonic cell. Optionally the cell is not a pluripotent or totipotent cell. In an example, the method is used to produce a human stem cell for human therapy (e.g., an iPS cell generated from a cell of a patient for reintroduction into the patient after the method of the invention has been performed on the cell), wherein the stem cell comprises a nucleotide sequence or gene sequence inserted by the method of the invention. The features of the examples in this paragraph can be combined.

In an example, the method is carried out in a mammalian cell. For example, the cell is a human cell in vitro or a non-human mammalian cell. For example, a non-human (e.g., rodent, rat or mouse) zygote. For example, a single-cell non-human zygote.

In an example, the method is carried out in a plant or non-human mammal, e.g. a rodent, mouse or rat or rabbit, or a tissue or organ thereof (eg, in vitro).

In an example, the 3' or each cleavage site is flanked 3' by PAM motif (eg, a motif disclosed herein, such as NGG or NGGNG sequence, wherein N is any base and G is a guanine). For example, one or more or all cleavage sites are flanked 3' by the sequence 5'-TGGTG-3'. Unlike dsDNA, the PAM is not absolutely required for ssDNA binding and cleavage: A single-stranded oligodeoxynucleotide containing a protospacer with or without a PAM sequence is bound nearly as well as dsDNA and may be used in the invention wherein a single strand of DNA is modified. Moreover, in the presence of $Mg^{2+}$ ions, Cas9 cuts ssDNA bound to the crRNA using its HNH active site independently of PAM.

Optionally, in any configuration, aspect, example or embodiment of the invention, step (a) is carried out by cleavage in one single strand of dsDNA or in ssDNA.

Optionally, in any configuration, aspect, example or embodiment of the invention, step (a) is carried out by combining in a cell the nucleic acid strand, a Cas endonuclease, a crRNA and a tracrRNA (e.g., provided by one or more gRNAs) for targeting the endonuclease to carry out the cleavage, and optionally an insert sequence for homologous recombination with the nucleic acid strand. Instead of an insert sequence, one can use an incoming sequence containing homology arms but no insert sequence, to effect deletion as described above. In an example, the Cas endonuclease is encoded by a nucleotide sequence that has been introduced into the cell. In an example, the gRNA is encoded by a DNA sequence that has been introduced into the cell.

In an example, the method is carried out in the presence of $Mg^{2+}$.

Optionally, in any configuration, aspect, example or embodiment of the invention, step (b) is performed by carrying out homologous recombination with an incoming nucleic acid comprising first and second homology arms, wherein the homology arms are substantially homologous respectively to a sequence extending 5' from the 5' end and a sequence extending 3' from the 3' end, wherein the second homology arm comprises a PAM sequence such that homologous recombination between the second homology arm and the sequence extending 3' from the 3' end produces a sequence comprising a PAM motif in the product of the method. The PAM can be any PAM sequence disclosed herein, for example. Thus, the method produces a modified nucleic acid strand comprising a PAM that can be used for a subsequent nucleic acid modification according to any configuration, aspect, example or embodiment of the invention, wherein a Cas endonuclease is used to cut the nucleic acid. This is useful, for example, for performing sequential endonuclease-mediated homology directed recombination (sEHDR) according to the invention, more particularly sCHDR described below.

Sequential Endonuclease-Mediated Homology Directed Recombination (sEHDR)

The Invention Further Provides:

A method of sequential endonuclease-mediated homology directed recombination (sEHDR) comprising carrying out the method of any preceding configuration, aspect, example or embodiment of the invention a first time and a second time, wherein endonuclease-mediated cleavage is used in each step (a); wherein the product of the first time is used for endonuclease-mediated cleavage the second time, whereby either (i) first and second nucleotide sequences are deleted the first time and the second times respectively; (ii) a first nucleotide sequence is deleted the first time and a second nucleotide sequence is inserted the second time; (iii) a first nucleotide sequence is inserted the first time and a second nucleotide sequence is deleted the second time; or (iv) first and second nucleotide sequences are inserted the first and second times respectively; optionally wherein the nucleic acid strand modification the second time is within 20, 10, 5, 4, 3, 2 or 1 or less nucleotides of the nucleic acid strand modification the first time or directly adjacent to the nucleic acid strand modification the first time.

For example, the first and second nucleotide sequences are inserted so that they are contiguous after the insertion the second time. Alternatively, the first and second deletions are such that a contiguous sequence has been deleted after the first and second deletions have been performed.

In an embodiment of sEHDR, the invention uses a Cas endonuclease. Thus, there is provided:

A method of sequential Cas-mediated homology directed recombination (sCHDR) comprising carrying out the method of any preceding claim a first time and a second time, wherein Cas endonuclease-mediated cleavage is used in each step (a); wherein step (b) of the first time is carried out performing homologous recombination with an incoming nucleic acid comprising first and second homology arms, wherein the homology arms are substantially homologous respectively to a sequence extending 5' from the 5' end and a sequence extending 3' from the 3' end, wherein the second homology arm comprises a PAM sequence such that homologous recombination between the second homology arm and the sequence extending 3' from the 3' end produces a sequence comprising a PAM motif in the product of the method; wherein the PAM motif of the product of the first time is used for Cas endonuclease-mediated cleavage the second time, whereby either (i) first and second nucleotide sequences are deleted the first time and the second times respectively; (ii) a first nucleotide sequence is deleted the first time and a second nucleotide sequence is inserted the second time; (iii) a first nucleotide sequence is inserted the first time and a second nucleotide sequence is deleted the second time; or (iv) first and second nucleotide sequences are inserted the first and second times respectively; optionally wherein the nucleic acid strand modification the second time is within 20, 10, 5, 4, 3, 2 or 1 or less nucleotides of the nucleic acid strand modification the first time or directly adjacent to the nucleic acid strand modification the first time.

For example, the first and second nucleotide sequences are inserted so that they are contiguous after the insertion the second time. Alternatively, the first and second deletions are such that a contiguous sequence has been deleted after the first and second deletions have been performed. In an embodiment (First Embodiment), the first time is carried out according to the third configuration of the invention, wherein the incoming nucleic acid comprises no sequence between the first and second homology arms, wherein sequence between the 5' and 3' ends is deleted by homologous recombination; and/or the second time is carried out according to the third configuration of the invention, wherein step (b) is performed by carrying out homologous recombination between an incoming nucleic acid comprising first and second homology arms, wherein the homology arms are substantially homologous respectively to a sequence extending 5' from the 5' end and a sequence extending 3' from the 3' end, wherein the incoming nucleic acid comprises no sequence between the first and second homology arms such that sequence between the 5' and 3' ends is deleted by homologous recombination; optionally wherein the second arm comprises a PAM motif such that the product of the second time comprises a PAM motif for use in a subsequent Cas endonuclease-mediated method according to any configuration, aspect, example or embodiment of the invention.

In an embodiment (Second Embodiment), the first time is carried out according to the first or second configuration of the invention, wherein the incoming nucleic acid comprises the insert sequence between the first and second homology arms, wherein the insert sequence is inserted between the 5' and 3' ends by homologous recombination; and/or the second time is carried out according to the first or second configuration of the invention, wherein step (b) is performed by carrying out homologous recombination between an incoming nucleic acid comprising first and second homology arms, wherein the homology arms are substantially homologous respectively to a sequence extending 5' from the 5' end and a sequence extending 3' from the 3' end, wherein the insert sequence is inserted between the 5' and 3' ends by homologous recombination; optionally wherein the second arm comprises a PAM motif such that the product of the second time comprises a PAM motif for use in a subsequent Cas endonuclease-mediated method according to any configuration, aspect, example or embodiment of the invention.

In an example, one of said first and second times is carried out as specified in the First Embodiment and the other time is carried out as specified in the Second Embodiment, wherein at least one sequence deletion and at least one sequence insertion is performed.

Optionally, in any configuration, aspect, example or embodiment of the invention, step (a) is carried out by Cas endonuclease-mediated cleavage using a Cas endonuclease, one or more crRNAs and a tracrRNA. For example, the method is carried out in a cell and the crRNA and tracrRNA is introduced into the cell as RNA molecules. For example, the method is carried out in a zygote (e.g., a non-human zygote, e.g., a rodent, rat or mouse zygote) and the crRNA and tracrRNA is injected into zygote. In another embodiment, the crRNA and tracrRNA are encoded by DNA within a cell or organism and are transcribed inside the cell (e.g., an ES cell, e.g., a non-human ES cell, e.g., a rodent, rat or mouse ES cell) or organism to produce the crRNA and tracrRNA. The organism is, for example, a non-human animal or plant or bacterium or yeast or insect. In an embodiment, the tracrRNA is in this way encoded by DNA but one or more crRNAs are introduced as RNA nucleic acid into the cell or organism to effect the method of the invention.

Additionally or alternatively to these examples, the endonuclease may be introduced as a protein or a vector encoding the endonuclease may be introduced into the cell or organism to effect the method of the invention. In another example, the endonuclease is encoded by DNA that is genomically integrated into the cell or organism and is transcribed and translated inside the cell or organism.

In an example, the method of the invention is carried out in an ES cell (e.g., a non-human ES cell, e.g., a rodent, rat or mouse ES cell) that has been pre-engineered to comprise an expressible genomically-integrated Cas endonuclease sequence (or a vector carrying this has been include in the cell). It would be possible to introduce (or encode) a tracrRNA. By introducing a crRNA with a guiding oligo sequence to target the desired area of the cell genome, one can then carry out modifications in the cell genome as per the invention. In an example, a gRNA as described herein is introduced into the ES cell. The genomically-integrated expressible Cas endonuclease sequence can, for example, be constitutively expressed or inducibly expressible. Alternatively or additionally, the sequence may be expressible in a tissue-specific manner in a progeny organism (e.g., a rodent) developed using the ES cell.

The initial ES cell comprising a genomically-integrated expressible Cas endonuclease sequence can be used, via standard techniques, to produce a progeny non-human animal that contains the expressible Cas endonuclease sequence. Thus, the invention provides:

A non-human animal (e.g., a vertebrate, mammal, fish or bird), animal cell, insect, insect cell, plant or plant cell comprising a genomically-integrated expressible Cas endonuclease nucleotide sequence and optionally a tracrRNA and/or a nucleotide sequence encoding a tracrRNA. The Cas endonuclease is, for example, Cas9 or Cys4. In an example, the animal, insect or plant genome comprises a chromosomal DNA sequence flanked by site-specific recombination sites and/or transposon elements (e.g., piggyBac transposon repeat elements), wherein the sequence encodes the endonuclease and optionally one or more gRNAs. As described in the Examples below, recombinase-mediated cassette exchange (RMCE) can be used to insert such a sequence. The transposon elements can be used to excise the sequence from the genome once the endonuclease has been used to perform recombination. The RMCE and/or transposon-mediated excision can be performed in a cell (e.g., an ES cell) that later is used to derive a progeny animal or plant comprising the desired genomic modification.

The invention also provides an ES cell derived or derivable from such an animal, wherein the ES cell comprises a genomically-integrated expressible Cas endonuclease nucleotide sequence. In an example, the ES cell is a rodent, e.g., a mouse or rat ES cell, or is a rabbit, dog, pig, cat, cow, non-human primate, fish, amphibian or bird ES cell.

The invention also provides a method of isolating an ES cell, the method comprising deriving an ES cell from an animal (e.g., a non-human animal, e.g., a rodent, e.g., a rat or a mouse), wherein the animal comprises a genomically-integrated expressible Cas endonuclease nucleotide sequence, as described herein.

In any of these aspects, instead of an ES cell, the cell may be an iPS cell or a totipotent or pluripotent cell. Thus, an iPS or stem cell can be derived from (e.g., a somatic cell of) a human, engineered in vitro to comprise a genomically-integrated expressible Cas endonuclease nucleotide sequence and optionally one or more DNA sequences encoding a tracrRNA or gRNA. The invention, thus, also relates to such a method and to a human iPS or stem cell comprising a genomically-integrated expressible Cas endonuclease nucleotide sequence and optionally one or more DNA sequences encoding a tracrRNA or gRNA. This cell can be used in a method of the invention to carry out genome modification (e.g., to correct a genetic defect, e.g., by replacement of defective sequence with a desired sequence, optionally with subsequent transposon-mediated excision of the endonuclease-encoding sequence). After optional excision of the Cas endonuclease sequence, the iPS cell or stem cell can be introduced into the donor human (or a different human, e.g., a genetic relative thereof) to carry out genetic therapy or prophylaxis. In the alternative, a totipotent or pluripotent human cell is used and then subsequently developed into human tissue or an organ or part thereof. This is useful for providing material for human therapy or prophylaxis or for producing assay materials (eg, for implantation into model non-human animals) or for use in in vitro testing (e.g., of drugs).

In an example the method uses a single guided RNA (gRNA) comprising a crRNA and a tracrRNA. The crRNA comprises an oligonucleotide sequence ("X" in the structure 5'-X-Y-3' mentioned below) that is chosen to target a desired part of the nucleic acid or genome to be modified. The skilled person will be able readily to select appropriate oligo sequence. In an example, the sequence is from 3 to 100 nucleotides long, eg, from 3 to 50, 40, 30, 25, 20, 15 or 10 nucleotides long, eg, from or 5, 10, 15 or 20 to 100 nuclueotides long, eg, from 5, 10, 15 or 20 to 50 nucleotides long.

For example, the gRNA is a single nucleic acid comprising both the crRNA and the tracrRNA. An example of a gRNA comprises the sequence 5'-[oligo]-[UUUUA-GAGCUA] (SEQ ID NO: 1)-[LINKER]-[UAGCAAGUUAAAA] (SEQ ID NO: 2)-3', wherein the LINKER comprises a plurality (e.g., 4 or more, e.g., 4, 5 or 6) nucleotides (e.g., 5'-GAAA-3').

For example, the crRNA has the structure 5'-X-Y-3', wherein X is an RNA nucleotide sequence (optionally at least 5 nucleotides long) and Y is a crRNA sequence comprising a nucleotide motif that hybridises with a motif comprised by the tracrRNA, wherein X is capable of hybridising with a nucleotide sequence 5' of the desired site of the 5' cut end, e.g., extending 5' from the desired site of the 5' cut.

In an example, Y is 5'-N1UUUUAN2N3GCUA-3' (SEQ ID NO: 3), wherein each of N1-3 is a A, U, C or G and/or the tracrRNA comprises the sequence (in 5' to 3' orientation) UAGCM1UUAAAAM2 (SEQ ID NO: 4, when M1 is, e.g., 5 nucleotides), wherein M1 is spacer nucleotide sequence and M2 is a nucleotide; e.g., N1-G, N2=G and N3=A. The spacer sequence is, e.g., 5, 4, 3, 2 or 1 RNA nucleotides in length (e.g., AAG in 5' to 3' orientation). M2 is, for example, a A,U, C or G (e.g., M2 is a G). In an embodiment, a chimaeric gRNA is used which comprises a sequence 5'-X-Y-Z-3', wherein X and Y are as defined above and Z is a tracrRNA comprising the sequence (in 5' to 3' orientation) UAGCM1UUAAAAM2 (SEQ ID NO: 4), wherein M1 is spacer nucleotide sequence and M2 is a nucleotide. In an example, Z comprises the sequence 5'-UAGCAAGUUAAAA-3' (SEQ ID NO: 2), e.g., Z is 5'-UAGCAAGUUAAAAUAAGGCUAGUCCG-3' (SEQ ID NO: 5). In an example, the gRNA has the sequence:

(SEQ ID NO: 5)
5'-GUUUUAGAGCUAGAAAUAGCAAGUUAAAAUAAGGCUAGUCCGUUAUC
AACUUGAAAAAGUGGCACCGAGUCGGUGC-3'.

When it is desired to use the present invention to insert an exogenous sequence into the nucleic acid to be modified, the exogenous sequence can be provided on linear or circular nucleic acid (e.g., DNA). Typically, the exogenous sequence is flanked by homology arms that can undergo homologous recombination with sequences 5' and 3' respectively of the site where the exogenous sequence is to be inserted. The skilled person is familiar with choosing homology arms for homologous recombination.

The invention can be used in a method of producing a transgenic organism, e.g., any organism recited herein. For example, the organism can be a non-human organism used as an assay model to test a pharmaceutical drug or to express an exogenous protein or a part thereof (e.g., a human protein target knocked-in into a non-human animal assay organism). In another example, the invention has been used to knock-out an endogenous sequence (e.g., a target protein) in an organism, such as a non-human organism. This can be useful to assess the effect (phenotype) of the knock-out and thus to assess potential drug targets or proteins implicated in disease. In one example, the organism is a non-human animal (e.g., a vertebrate, mammal, bird, fish, rodent, mouse, rat or rabbit) in which a human target protein has been knocked-in using the invention. Optionally, the invention has been used to knock out an orthologous or homologous endogenous target of the organism (eg, an endogenous target sequence has been replaced at the endogenous position by an orthologous or homologous human target sequence). In this way, an assay model can be produced for testing pharmaceutical drugs that act via the human target.

In an embodiment, the organism is a non-human vertebrate that expresses human antibody variable regions whose genome comprises a replacement of an endogenous target with an orthologous or homologous human sequence. In an example, the method of the invention is used to produce an Antibody-Generating Vertebrate or Assay Vertebrate as disclosed in WO2013061078, the disclosure of which, and specifically including the disclosure of such Vertebrates, their composition, manufacture and use, is included specifically herein by reference as though herein reproduced in its entirety and for providing basis for claims herein.

In an example, an exogenous regulatory element is knocked-in using the method. For example, it is knocked-in to replace an endogenous regulatory element.

In one aspect, the invention provides a method of producing a cell or a transgenic non-human organism (e.g., any non-human organism recited herein), the method comprising
(a) carrying out the method of any in any configuration, aspect, example or embodiment of the invention to (i) knock out a target nucleotide sequence in the genome of a first cell and/or (ii) knock in an insert nucleotide sequence into the genome of a first cell, optionally wherein the insert sequence replaces a target sequence in whole or in part at the endogenous location of the target sequence in the genome; wherein the cell or a progeny thereof can develop into a non-human organism or cell; and
(b) developing the cell or progeny into a non-human organism or a non-human cell.

In an example, the organism or cell is homozygous for the modification (i) and/or (ii).

In an example, the cell is an ES cell, iPS cell, totipotent cell or pluripotent cell. In an example, the cell is a non-human vertebrate cell or a human cell in vitro. In an example, the cell is a plant, yeast, insect or bacterial cell.

In an example, the cell or organism is a rodent (e.g., a mouse or rat) cell or a rabbit, bird, fish, chicken, non-human primate, monkey, pig, dog, Camelid, shark, sheep, cow or cat cell.

In an example, the target sequence is an endogenous sequence comprising all or part of a regulatory element or encoding all or part of a protein. In an example, the insert sequence is a synthetic sequence; or comprises a sequence encoding all or part of a protein from a species other than the species from which the first cell is derived; or comprises a regulatory element from said first species. This is useful to combine genes with new regulatory elements.

In an example, the insert sequence encodes all or part of a human protein or a human protein subunit or domain. For example, the insert sequence encodes a cell membrane protein, secreted protein, intracellular protein, cytokine, receptor protein (e.g., Fc receptor protein, such as FcRn or a Ed receptor protein), protein of the human immune system or domain thereof (e.g., an Ig protein or domain, such as an antibody or TCR protein or domain, or a MHC protein), a hormone or growth factor.

The Invention Also Provides:

A cell (e.g., an isolated or purified cell, eg, a cell in vitro, or any cell disclosed herein) or a non-human organism (e.g., any organism disclosed herein) whose genome comprises a modification comprising a non-endogenous nucleotide sequence flanked by endogenous nucleotide sequences, wherein the cell or organism is obtainable by the method of any configuration, aspect, example or embodiment of the invention, and wherein the non-endogenous sequence is flanked 3' and/or 5' by (e.g., within 20, 10, 5, 4, 3, 2 or 1 or less nucleotides of, or directly adjacent to) a Cas PAM motif; wherein the cell is not comprised by a human; and one, more or all of (a) to (d) applies (a) the genome is homozygous for the modification; or comprises the modification at one allele and is unmodified by Cas-mediated homologous recombination at the other allele;
(b) the non-endogenous sequence comprises all or part of a regulatory element or encodes all or part of a protein;
(c) the non-endogenous sequence is at least 20, 30, 40, 50, 60, 70, 80, 90, 100, 150, 200, 300, 400, 500, 600, 700, 800 or 900 nucleotides, or at least 1, 2, 3, 5, 10, 20, 50 or 100kb long;
(d) the non-endogenous sequence replaces an orthologous or homologous sequence in the genome.

The cell can be a human cell, or included in human tissue but not part of a human being. For example, the cell is a human cell in vitro.

In an example, the non-endogenous sequence is a human sequence.

In an example, the PAM motif is any PAM disclosed herein or comprises a sequence selected from CCN, TCN, TTC, AWG, CC, NNAGNN, NGGNG GG, NGG, WGG, CWT, CTT and GAA. For example, the motif is a Cas9 PAM motif. For example, the PAM is NGG. In another example, the PAM is GG.

In an example, there is a PAM motif no more than 10 nucleotides (e.g., 3 nucleotides) 3' and/or 5' of the non-endogenous sequence.

In an example, the PAM motif is recognised by a *Streptococcus* Cas9.

In an example, the cell or organism is a non-human vertebrate cell or a non-human vertebrate that expresses one or more human antibody heavy chain variable domains (and optionally no heavy chain variable domains of a non-human vertebrate species). For example, the organism is an Antibody-Generating Vertebrate or Assay Vertebrate disclosed in WO2013061078.

In an example, the cell or organism is a non-human vertebrate cell or a non-human vertebrate that expresses one or more human antibody kappa light chain variable domains (and optionally no kappa light chain variable domains of a non-human vertebrate species).

In an example, the cell or organism is a non-human vertebrate cell or a non-human vertebrate that expresses one or more human antibody lambda light chain variable domains (and optionally no kappa light chain variable domains of a non-human vertebrate species).

In an example, the non-endogenous sequence encodes a human Fc receptor protein or subunit or domain thereof (e.g., a human FcRn or FcY receptor protein, subunit or domain).

In an example, the non-endogenous sequence comprises one or more human antibody gene segments, an antibody variable region or an antibody constant region.

In an example, the insert sequence is a human sequence that replaces or supplements an orthologous non-human sequence.

The Invention Also Provides:

A monoclonal or polyclonal antibody prepared by immunisation of a vertebrate (e.g., mouse or rat) of the invention (or produced by a method of the invention) with an antigen.

The Invention Also Provides:

A method of isolating an antibody that binds a predetermined antigen, the method comprising
(a) providing a vertebrate (optionally a mouse or rat) of the invention (or produced by a method of the invention);
(b) immunising said vertebrate with said antigen;

(c) removing B lymphocytes from the vertebrate and selecting one or more B lymphocytes expressing antibodies that bind to the antigen;
(d) optionally immortalizing said selected B lymphocytes or progeny thereof, optionally by producing hybridomas therefrom; and
(e) isolating an antibody (eg, and IgG-type antibody) expressed by the B lymphocytes.

In an example, the method comprises the step of isolating from said B lymphocytes nucleic acid encoding said antibody that binds said antigen; optionally exchanging the heavy chain constant region nucleotide sequence of the antibody with a nucleotide sequence encoding a human or humanised heavy chain constant region and optionally affinity maturing the variable region of said antibody; and optionally inserting said nucleic acid into an expression vector and optionally a host.

In an example, the method comprises making a mutant or derivative of the antibody produced by the method.

The invention provides the use of an isolated, monoclonal or polyclonal antibody described herein, or a mutant or derivative antibody thereof that binds said antigen, in the manufacture of a composition for use as a medicament.

The invention provides the use of an isolated, monoclonal or polyclonal antibody described herein, or a mutant or derivative antibody thereof that binds said antigen for use in medicine.

The invention provides a nucleotide sequence encoding an antibody described herein, optionally wherein the nucleotide sequence is part of a vector.

The invention provides a pharmaceutical composition comprising the antibody or antibodies described herein and a diluent, excipient or carrier.

The invention provides an ES cell, a non-human animal or a non-human blastocyst comprising an expressible genomically-integrated nucleotide sequence encoding a Cas endonuclease (e.g., a Cas9 or Cys4) and optionally an expressible genomically-integrated nucleotide sequence encoding a tracrRNA or a gRNA. For example, the ES cell is any ES cell type described herein.

In an example of the cell, animal or blastocyst, the endonuclease sequence is constitutively expressible.

In an example of the cell, animal or blastocyst, the endonuclease sequence is inducibly expressible.

In an example of the cell, animal or blastocyst, the endonuclease sequence is expressible in a tissue-specific manner in the animal or a progeny thereof, or in a non-human animal that is a progeny of the cell or blastocyst.

In an example, the cell, animal or blastocyst comprises one or more gRNAs or an expressible nucleotide sequence encoding a gRNA or a plurality of expressible nucleotide sequences each encoding a different gRNA.

The invention provides the use of the cell, animal or blastocyst in a method according to any configuration, aspect, embodiment or example of the invention.

An aspect provides an antibody produced by the method of the invention, optionally for use in medicine, eg, for treating and/or preventing a medical condition or disease in a patient, e.g., a human.

An aspect provides a nucleotide sequence encoding the antibody of the invention, optionally wherein the nucleotide sequence is part of a vector. Suitable vectors will be readily apparent to the skilled person, eg, a conventional antibody expression vector comprising the nucleotide sequence together in operable linkage with one or more expression control elements.

An aspect provides a pharmaceutical composition comprising the antibody of the invention and a diluent, excipient or carrier, optionally wherein the composition is contained in an IV container (e.g., and IV bag) or a container connected to an IV syringe.

An aspect provides the use of the antibody of the invention in the manufacture of a medicament for the treatment and/or prophylaxis of a disease or condition in a patient, e.g., a human.

In a further aspect the invention relates to humanised antibodies and antibody chains produced according to the present invention, both in chimaeric and fully humanised form, and use of said antibodies in medicine. The invention also relates to a pharmaceutical composition comprising such an antibody and a pharmaceutically acceptable carrier or other excipient.

Antibody chains containing human sequences, such as chimaeric human-non human antibody chains, are considered humanised herein by virtue of the presence of the human protein coding regions region. Fully human antibodies may be produced starting from DNA encoding a chimaeric antibody chain of the invention using standard techniques.

Methods for the generation of both monoclonal and polyclonal antibodies are well known in the art, and the present invention relates to both polyclonal and monoclonal antibodies of chimaeric or fully humanised antibodies produced in response to antigen challenge in non human-vertebrates of the present invention.

In a yet further aspect, chimaeric antibodies or antibody chains generated in the present invention may be manipulated, suitably at the DNA level, to generate molecules with antibody-like properties or structure, such as a human variable region from a heavy or light chain absent a constant region, for example a domain antibody; or a human variable region with any constant region from either heavy or light chain from the same or different species; or a human variable region with a non-naturally occurring constant region; or human variable region together with any other fusion partner. The invention relates to all such chimaeric antibody derivatives derived from chimaeric antibodies identified according to the present invention.

In a further aspect, the invention relates to use of animals of the present invention in the analysis of the likely effects of drugs and vaccines in the context of a quasi-human antibody repertoire.

The invention also relates to a method for identification or validation of a drug or vaccine, the method comprising delivering the vaccine or drug to a mammal of the invention and monitoring one or more of: the immune response, the safety profile; the effect on disease.

The invention also relates to a kit comprising an antibody or antibody derivative as disclosed herein and either instructions for use of such antibody or a suitable laboratory reagent, such as a buffer, antibody detection reagent.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

Any part of this disclosure may be read in combination with any other part of the disclosure, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Cong L, Ran F A, Cox D, Lin S, Barretto R, Habib N, Hsu P D, Wu X, Jiang W, Marraffini L A et al: Multiplex genome engineering using CRISPR/Cas systems. *Science* 2013, 339(6121):819-823.
2. Wang H, Yang H, Shivalila C S, Dawlaty M M, Cheng A W, Zhang F, Jaenisch R: One-step generation of mice carrying mutations in multiple genes by CRISPR/Cas-mediated genome engineering. *Cell* 2013, 153(4):910-918.
3. Mali P, Yang L, Esvelt K M, Aach J, Guell M, DiCarlo J E, Norville J E, Church G M: RNA-guided human genome engineering via Cas9. *Science* 2013, 339(6121): 823-826.
4. Gaj T, Gersbach C A, Barbas C F, 3rd: ZFN, TALEN, and CRISPR/Cas-based methods for genome engineering. *Trends Biotechnol* 2013, 31(7):397-405.
5. Perez-Pinera P, Ousterout D G, Gersbach C A: Advances in targeted genome editing. *Curr Opin Chem Biol* 2012, 16(3-4):268-277.
6. Shah S A, Erdmann S, Mojica F J, Garrett R A: Protospacer recognition motifs: Mixed identities and functional diversity. *RNA Biol* 2013, 10(5).
7. Haurwitz R E, Sternberg S H, Doudna J A: Csy4 relies on an unusual catalytic dyad to position and cleave CRISPR RNA. *EMBO J* 2012, 31(12):2824-2832.
8. Yusa K, Zhou L, Li M A, Bradley A, Craig N L: A hyperactive piggyBac transposase for mammalian applications. *Proc Natl Acad Sci USA* 2011, 108(4):1531-1536.
9. Qiao J, Oumard A, Wegloehner W, Bode J: Novel tag-and-exchange (RMCE) strategies generate master cell clones with predictable and stable transgene expression properties. *J Mol Biol* 2009, 390(4):579-594.
10. Oumard A, Qiao J, Jostock T, Li J, Bode J: Recommended Method for Chromosome Exploitation: RMCE-based Cassette-exchange Systems in Animal Cell Biotechnology. *Cytotechnology* 2006, 50(1-3):93-108.

The present invention is described in more detail in the following non limiting exemplification.

EXAMPLES

Example 1: Precise DNA Modifications (a) Use of Nickase for HDR

It has been reported that the Cas9 nuclease can be converted into a nickase through the substitution of an aspartate to alanine (D10A) in the RuvCl domain of SpCas9 (Cong et al). It is noteworthy that DNA single-stranded breaks are preferentially repaired through the HDR pathway. The Cas9 D10A nickase, when in a complex with mature crRNA:tracrRNA, can specifically induce DNA nicking at a precise location. With this in mind, we propose extending the application of the CRISPR/Cas system by creating a nick in a given location in a genome using Cas9 D10A nickase and then exploiting the HDR pathway for inserting a single-stranded DNA fragment (endogenous or exogenous) which will contain DNA homology flanking the nick. Typically for recombineering 50 bp is enough for efficient recombination) flanking the nicked DNA junction to bring in and insert a given DNA in a precision location; similar size homology will be used with the present example (FIG. 1). Guide RNA (gRNA) will be design individually per target protospacer sequence or incorporated into a single CRISPR array encoding for 2 or more spacer sequences allowing multiplex genome editing from a single CRSPR array.

In a separate setting, two gRNA or a single CRISPR array encoding multiple spacer sequence can be designed flanking a gene or a region of interest and with the association of Cas9 D10A nickase, two separate single-stranded breaks can be induced. This in association with a single-stranded DNA fragment containing DNA homology to the 5' breakpoint junction of the first DNA nick and DNA homology to the 3' breakpoint junction of the second nick the region in between the two single stranded DNA nick can be precisely deleted (FIG. 2). In an another setting, two separate gRNA or a multiplex single CRISPR array can be designed flanking a gene or a region of interest and with the association of Cas9 D10A nickase two separate single-stranded breaks can be induced. In this case the intruding single stranded DNA fragment can contain DNA sequence from either endogenous or exogenous source containing sequence for a known gene, regulatory element promoter etc. This single-stranded DNA fragment (or double stranded DNA) can be brought together to replace the DNA region of interest flanked by DNA nick by arming it with DNA homology from the 5' region of the first nick and 3' region from the second nick (FIG. 3). Due to the high efficiency of the CRISPR/Cas system to cleave DNA, the above proposed strategy will not require introduction of any selection marker thus creating exact seamless genome editing in a precise and defined manner. As an option, a selection marker can be included flanked by PiggyBac LTRs to allow for the direct selection of correctly modified clones. Once the correct clones have been identified, the selection marker can be removed conveniently through the expression of hyperactive piggyBac transposase (Yusa K, Zhou L, Li M A, Bradley A, Craig N L: A hyperactive piggyBac transposase for mammalian applications. *Proc Natl Acad Sci USA* 2011, 108(4):1531-1536). Furthermore, the above approaches can be applied to ES cells, mammalian cells, yeast cells, bacterial cells, plant cells as well as directly performing in zygotes to expedite the process of homozygeous genome engineering in record time. It would be also possible to multiplex this system to generate multiple simultaneous DNA insertions (KI), deletions (KO) and the sequential deletion and insertion (KO→KI).

Example 2: Recycling PAM for Sequential Insertions or Deletions

In certain settings it may be useful to edit a genome by chromosome walking. Using any of the three examples outlined above, it could be possible to carry out sequential genome editing in a stepwise fashion whereby the PAM sequence used in a previous round of CRISPR/Cas mediated genome editing, can be re-used to carry out multiple rounds of genome editing such as deletions, insertions or the simultaneous deletion and insertion. An example of sequential deletion whereby the PAM sequence from the previous genome editing step is recycled is shown in FIG. 4. Using the PAM recycling approach, it is possible to carry out sequential insertions as well as sequential simultaneous deletion and insertion.

Example 3: Rapid Insertion of Lox Sites Using CRISPR/Cas System

Targeting efficiency using conventional homologous recombination methods in ES cells is low. In a different setting, the CRISPR/Cas system can be used to rapidly and efficiently introduce lox sites or other recombinase recognition sequence such as Frt in a defined location to act as a landing pad for genome editing using recombinase mediated cassette exchange (RMCE) (Qiao J, Oumard A, Wegloehner W, Bode J: Novel tag-and-exchange (RMCE) strategies generate master cell clones with predictable and stable transgene expression properties. *J Mol Biol* 2009, 390(4): 579-594; and Oumard A, Qiao J, Jostock T, Li J, Bode J: Recommended Method for Chromosome Exploitation: RMCE-based Cassette-exchange Systems in Animal Cell Biotechnology. *Cytotechnology* 2006, 50(1-3):93-108). Once the lox sites are introduced into the genome, inversion, deletion or cassette exchange to delete and introduce DNA fragment varying in size at this site can be efficiently conducted via expression of Cre recombinase. An example of CRISPR/Cas mediated lox insertion followed by RMCE is shown in FIG. 5. The RMCE step can be used to invert the region flanked by lox site or to delete this region as well as to simultaneously delete and insert DNA of interest in this region. Furthermore, the RMCE step can be adapted for carrying out multiple sequential rounds of RMCE (sRMCE).

Example 4

Reference is made to FIG. 6. A piggyBac transposon harbouring a PGK promoter-driven loxP/mutant lox-flanked neo$^R$ gene is targeted into an ES cell genome by standard homologous recombination. The targeted clones can be selected by G418. This provides a landing pad for the following recombinase-mediated cassette exchange (RMCE). Such an ES clone can be used a parental cells for any modification further. A cassette containing the loxP/mutant lox-flanked promoterless PuroΔTK-T2A-Cas9 and U6 polymerase III promoter-driven guide RNA (gRNA) genes are inserted into the landing pad through transient cre expression. The gRNA genes can be one or more than one which target to the same gene or different genes. The inserted clones can be selected with puromycin and confirmed by junction PCRs. During the selection, the expression of Cas9 and gRNAs from the inserted cassette results in more efficient gene targeting or modification than transient expression of the Cas9 and gRNA can achieve. Following 4-6 day selection, the whole modified cassette is excised by the transient expression of piggyBac transposase (Pease). The final ES cell clones would not contain any Cas9 or gRNA sequence. The clones with homozygous modified genes would be confirmed by PCR and sequence.

The main feature of this invention is to control the Cas9 and gRNA expression in certain time to be sufficient to generate efficient targeting rates.

Example 5: Methodology

Reconstructing CRISPR/Cas Vector System (Nuclease)

The CRISPR/Cas genome editing system has been reconstructed in vitro and exemplified in mouse embryonic stem cells using vector pX330 containing humanised *S. pyogenes* (hSpCsn1) (Cong et al). The CRISPR/Cas system can be reconstructed as described in Cong et al using synthetic DNA strings and DNA assembly. In the present example, the entire DNA assembly would constitute a 6006 bp fragment containing 45 bp homology to pBlueScript KS+ vector 5' to the EcoRV cutting site, Human U6 promoter, two BbsI restriction sites for cloning in the spacer sequence which fuses to a chimeric guided RNA sequence, chicken beta-actin promoter with 3 FLAG, nuclear localisation signal (NLS) followed by hSpCsn1 sequence and another NLS, bGH polyA, inverted terminal repeat sequence and finally another 45 bp homology to pBlueScript KS+3' to the EcoRV cutting site. This 6006 bp stretch of DNA will be synthetized as 7 individual DNA fragments where each fragment will have a 45 bp overlap to the adjacent DNA fragment to allow DNA assembly. The DNA sequence of these fragments is shown below in the order of assembly.

Fragment 1A (1340 bp)

(SEQ ID NO: 7)
GGTACCGGGCCCCCCCTCGAGGTCGACGGTATCGATAAGCTTGATGAGGG

CCTATTTCCCATGATTCCTTCATATTTGCATATACGATACAAGGCTGTTA

GAGAGATAATTGGAATTAATTTGACTGTAAACACAAAGATATTAGTACAA

AATACGTGACGTAGAAAGTAATAATTTCTTGGGTAGTTTGCAGTTTTAAA

ATTATGTTTTAAAATGGACTATCATATGCTTACCGTAACTTGAAAGTATT

TCGATTTCTTGGCTTTATATATCTTGTGGAAAGGACGAAACACCGGGTCT

TCGAGAAGACCTGTTTTAGAGCTAGAAATAGCAAGTTAAAATAAGGCTAG

TCCGTTATCAACTTGAAAAAGTGGCACCGAGTCGGTGCTTTTTTGTTTTA

GAGCTAGAAATAGCAAGTTAAAATAAGGCTAGTCCGTTTTTAGCGCGTGC

GCCAATTCTGCAGACAAATGGCTCTAGAGGTACCCGTTACATAACTTACG

GTAAATGGCCCGCCTGGCTGACCGCCCAACGACCCCCGCCCATTGACGTC

AATAGTAACGCCAATAGGGACTTTCCATTGACGTCAATGGGTGGAGTATT

TACGGTAAACTGCCCACTTGGCAGTACATCAAGTGTATCATATGCCAAGT

ACGCCCCCTATTGACGTCAATGACGGTAAATGGCCCGCCTGGCATTGTGC

CCAGTACATGACCTTATGGGACTTTCCTACTTGGCAGTACATCTACGTAT

TAGTCATCGCTATTACCATGGTCGAGGTGAGCCCCACGTTCTGCTTCACT

CTCCCCATCTCCCCCCCCTCCCCACCCCCAATTTTGTATTTATTTATTTT

TTAATTATTTTGTGCAGCGATGGGGGCGGGGGGGGGGGGGGCGCGCGC

CAGGCGGGGCGGGGCGGGGCGAGGGGCGGGGCGGGGCGAGGCGGAGAGGT

GCGGCGGCAGCCAATCAGAGCGGCGCGCTCCGAAAGTTTCCTTTTATGGC

GAGGCGGCGGCGGCGGCGGCCCTATAAAAAGCGAAGCGCGCGGCGGGCGG

GAGTCGCTGCGACGCTGCCTTCGCCCCGTGCCCCGCTCCGCCGCCGCCTC

GCGCCGCCCGCCCCGGCTCTGACTGACCGCGTTACTCCCACAGGTGAGCG

GGCGGGACGGCCCTTCTCCTCCGGGCTGTAATTAGCTGAGCAAGAGGTAA

GGGTTTAAGGGATGGTTGGTTGGTGGGGTATTAATGTTTAATTACCTGGA

GCACCTGCCTGAAATCACTTTTTTTCAGGTTGGACCGGTGCCACCATGGA

CTATAAGGACCACGACGGAGACTACAAGGATCATGATATT.

Fragment 2 (852 bp)

(SEQ ID NO: 8)
ATGGACTATAAGGACCACGACGGAGACTACAAGGATCATGATATTGATTA

CAAAGACGATGACGATAAGATGGCCCCAAAGAAGAAGCGGAAGGTCGGTA

TCCACGGAGTCCCAGCAGCCGACAAGAAGTACAGCATCGGCCTGGACATC

GGCACCAACTCTGTGGGCTGGGCCGTGATCACCGACGAGTACAAGGTGCC

CAGCAAGAAATTCAAGGTGCTGGGCAACACCGACCGGCACAGCATCAAGA

AGAACCTGATCGGAGCCCTGCTGTTCGACAGCGGCGAAACAGCCGAGGCC

ACCCGGCTGAAGAGAACCGCCAGAAGAAGATACACCAGACGGAAGAACCG

GATCTGCTATCTGCAAGAGATCTTCAGCAACGAGATGGCCAAGGTGGACG

ACAGCTTCTTCCACAGACTGGAAGAGTCCTTCCTGGTGGAAGAGGATAAG

AAGCACGAGCGGCACCCCATCTTCGGCAACATCGTGGACGAGGTGGCCTA

CCACGAGAAGTACCCCACCATCTACCACCTGAGAAAGAAACTGGTGGACA

GCACCGACAAGGCCGACCTGCGGCTGATCTATCTGGCCCTGGCCCACATG

ATCAAGTTCCGGGGCCACTTCCTGATCGAGGGCGACCTGAACCCCGACAA

CAGCGACGTGGACAAGCTGTTCATCCAGCTGGTGCAGACCTACAACCAGC

TGTTCGAGGAAAACCCCATCAACGCCAGCGGCGTGGACGCCAAGGCCATC

CTGTCTGCCAGACTGAGCAAGAGCAGACGGCTGGAAAATCTGATCGCCCA

GCTGCCCGGCGAGAAGAAGAATGGCCTGTTCGGAAACCTGATTGCCCTGA

GC.

Fragment 3 (920 bp)

(SEQ ID NO: 9)
GGCGAGAAGAAGAATGGCCTGTTCGGAAACCTGATTGCCCTGAGCCTGGG

CCTGACCCCCAACTTCAAGAGCAACTTCGACCTGGCCGAGGATGCCAAAC

TGCAGCTGAGCAAGGACACCTACGACGACGACCTGGACAACCTGCTGGCC

CAGATCGGCGACCAGTACGCCGACCTGTTTCTGGCCGCCAAGAACCTGTC

CGACGCCATCCTGCTGAGCGACATCCTGAGAGTGAACACCGAGATCACCA

AGGCCCCCCTGAGCGCCTCTATGATCAAGAGATACGACGAGCACCACCAG

GACCTGACCCTGCTGAAAGCTCTCGTGCGGCAGCAGCTGCCTGAGAAGTA

CAAAGAGATTTTCTTCGACCAGAGCAAGAACGGCTACGCCGGCTACATTG

ACGGCGGAGCCAGCCAGGAAGAGTTCTACAAGTTCATCAAGCCCATCCTG

GAAAAGATGGACGGCACCGAGGAACTGCTCGTGAAGCTGAACAGAGAGGA

CCTGCTGCGGAAGCAGCGGACCTTCGACAACGGCAGCATCCCCCACCAGA

TCCACCTGGGAGAGCTGCACGCCATTCTGCGGCGGCAGGAAGATTTTTAC

CCATTCCTGAAGGACAACCGGGAAAAGATCGAGAAGATCCTGACCTTCCG

CATCCCCTACTACGTGGGCCCTCTGGCCAGGGGAAACAGCAGATTCGCCT

GGATGACCAGAAAGAGCGAGGAAACCATCACCCCCTGGAACTTCGAGGAA

GTGGTGGACAAGGGCGCTTCCGCCCAGAGCTTCATCGAGCGGATGACCAA

CTTCGATAAGAACCTGCCCAACGAGAAGGTGCTGCCCAAGCACAGCCTGC

TGTACGAGTACTTCACCGTGTATAACGAGCTGACCAAAGTGAAATACGTG

ACCGAGGGAATGAGAAAGCC.

Fragment 4 (920 bp)

(SEQ ID NO: 10)
CGAGCTGACCAAAGTGAAATACGTGACCGAGGGAATGAGAAAGCCCGCCT

TCCTGAGCGGCGAGCAGAAAAAGGCCATCGTGGACCTGCTGTTCAAGACC

AACCGGAAAGTGACCGTGAAGCAGCTGAAAGAGGACTACTTCAAGAAAAT

CGAGTGCTTCGACTCCGTGGAAATCTCCGGCGTGGAAGATCGGTTCAACG

CCTCCCTGGGCACATACCACGATCTGCTGAAAATTATCAAGGACAAGGAC

TTCCTGGACAATGAGGAAAACGAGGACATTCTGGAAGATATCGTGCTGAC

CCTGACACTGTTTGAGGACAGAGAGATGATCGAGGAACGGCTGAAAACCT

ATGCCCACCTGTTCGACGACAAAGTGATGAAGCAGCTGAAGCGGCGGAGA

TACACCGGCTGGGGCAGGCTGAGCCGGAAGCTGATCAACGGCATCCGGGA

CAAGCAGTCCGGCAAGACAATCCTGGATTTCCTGAAGTCCGACGGCTTCG

CCAACAGAAACTTCATGCAGCTGATCCACGACGACAGCCTGACCTTTAAA

GAGGACATCCAGAAAGCCCAGGTGTCCGGCCAGGGCGATAGCCTGCACGA

GCACATTGCCAATCTGGCCGGCAGCCCCGCCATTAAGAAGGGCATCCTGC

AGACAGTGAAGGTGGTGGACGAGCTCGTGAAAGTGATGGGCCGGCACAAG

CCCGAGAACATCGTGATCGAAATGGCCAGAGAGAACCAGACCACCCAGAA

GGGACAGAAGAACAGCCGCGAGAGAATGAAGCGGATCGAAGAGGGCATCA

Fragment 5 (920 bp)

(SEQ ID NO: 11)
ACTACCTGCAGAATGGGCGGGATATGTACGTGGACCAGGAACTGGACATC
AACCGGCTGTCCGACTACGATGTGGACCATATCGTGCCTCAGAGCTTTCT
GAAGGACGACTCCATCGACAACAAGGTGCTGACCAGAAGCGACAAGAACC
GGGGCAAGAGCGACAACGTGCCCTCCGAAGAGGTCGTGAAGAAGATGAAG
AACTACTGGCGGCAGCTGCTGAACGCCAAGCTGATTACCCAGAGAAAGTT
CGACAATCTGACCAAGGCCGAGAGAGGCGGCCTGAGCGAACTGGATAAGG
CCGGCTTCATCAAGAGACAGCTGGTGGAAACCCGGCAGATCACAAAGCAC
GTGGCACAGATCCTGGACTCCCGGATGAACACTAAGTACGACGAGAATGA
CAAGCTGATCCGGGAAGTGAAAGTGATCACCCTGAAGTCCAAGCTGGTGT
CCGATTTCCGGAAGGATTTCCAGTTTTACAAAGTGCGCGAGATCAACAAC
TACCACCACGCCCACGACGCCTACCTGAACGCCGTCGTGGGAACCGCCCT
GATCAAAAAGTACCCTAAGCTGGAAAGCGAGTTCGTGTACGGCGACTACA
AGGTGTACGACGTGCGGAAGATGATCGCCAAGAGCGAGCAGGAAATCGGC
AAGGCTACCGCCAAGTACTTCTTCTACAGCAACATCATGAACTTTTTCAA
GACCGAGATTACCCTGGCCAACGGCGAGATCCGGAAGCGGCCTCTGATCG
AGACAAACGGCGAAACCGGGGAGATCGTGTGGGATAAGGGCCGGGATTTT
GCCACCGTGCGGAAAGTGCTGAGCATGCCCCAAGTGAATATCGTGAAAAA
GACCGAGGTGCAGACAGGCGGCTTCAGCAAAGAGTCTATCCTGCCCAAGA
GGAACAGCGATAAGCTGATC.

Fragment 6 (789 bp)

(SEQ ID NO: 12)
AGCAAAGAGTCTATCCTGCCCAAGAGGAACAGCGATAAGCTGATCGCCAG
AAAGAAGGACTGGGACCCTAAGAAGTACGGCGGCTTCGACAGCCCCACCG
TGGCCTATTCTGTGCTGGTGGTGGCCAAAGTGGAAAAGGGCAAGTCCAAG
AAACTGAAGAGTGTGAAAGAGCTGCTGGGGATCACCATCATGGAAAGAAG
CAGCTTCGAGAAGAATCCCATCGACTTTCTGGAAGCCAAGGGCTACAAAG
AAGTGAAAAAGGACCTGATCATCAAGCTGCCTAAGTACTCCCTGTTCGAG
CTGGAAAACGGCCGGAAGAGAATGCTGGCCTCTGCCGGCGAACTGCAGAA
GGGAAACGAACTGGCCCTGCCCTCCAAATATGTGAACTTCCTGTACCTGG
CCAGCCACTATGAGAAGCTGAAGGGCTCCCCCGAGGATAATGAGCAGAAA
CAGCTGTTTGTGGAACAGCACAAGCACTACCTGGACGAGATCATCGAGCA
GATCAGCGAGTTCTCCAAGAGAGTGATCCTGGCCGACGCTAATCTGGACA
AAGTGCTGTCCGCCTACAACAAGCACCGGGATAAGCCCATCAGAGAGCAG
GCCGAGAATATCATCCACCTGTTTACCCTGACCAATCTGGGAGCCCCTGC
CGCCTTCAAGTACTTTGACACCACCATCGACCGGAAGAGGTACACCAGCA
CCAAAGAGGTGCTGGACGCCACCCTGATCCACCAGAGCATCACCGGCCTG
TACGAGACACGGATCGACCTGTCTCAGCTGGGAGGCGAC.

Fragment 7 (535 bp)

(SEQ ID NO: 13)
GGCCTGTACGAGACACGGATCGACCTGTCTCAGCTGGGAGGCGACAAAAG
GCCGGCGGCCACGAAAAAGGCCGGCCAGGCAAAAAAGAAAAAGTAAGAAT
TCCTAGAGCTCGCTGATCAGCCTCGACTGTGCCTTCTAGTTGCCAGCCAT
CTGTTGTTTGCCCCTCCCCCGTGCCTTCCTTGACCCTGGAAGGTGCCACT
CCCACTGTCCTTTCCTAATAAAATGAGGAAATTGCATCGCATTGTCTGAG
TAGGTGTCATTCTATTCTGGGGGGTGGGGTGGGGCAGGACAGCAAGGGGG
AGGATTGGGAAGAGAATAGCAGGCATGCTGGGGAGCGGCCGCAGGAACCC
CTAGTGATGGAGTTGGCCACTCCCTCTCTGCGCGCTCGCTCGCTCACTGA
GGCCGGGCGACCAAAGGTCGCCCGACGCCCGGGCTTTGCCCGGGCGGCCT
CAGTGAGCGAGCGAGCGCGCAGCTGCCTGCAGGGGCGCCTATCGAATTCC
TGCAGCCCGGGGGATCCACTAGTTCTAGAGCGGCC.

To reconstruct the CRISPR/Cas system described in Cong et al the above DNA fragments in addition to EcoRV linearised pBlueScript KS+ vector will be assembled using Gibson Assembly kit (NEB Cat No. E5510 S). As an alternative approach, the 6006 bp fragment can be assembled by assembly PCR by mixing molar ratio of the individual DNA fragments together and using the DNA mixture as PCR template. The assembled PCR product can then be cloned directly into pBlueScript vector or a standard cloning vector system such as a TOPO TA cloning kit (Invitrogen).

Reconstructing CRISPR/Cas Vector System (D10A Nickase)

The D10A nickase version of the CRISPR/Cas system can be conveniently reconstructed by assembling the above fragments where fragment 2 is replaced with fragment 2A which contains the D10A substitution (See sequence below).

Fragment 2A (852 bp)

(SEQ ID NO: 14)
ATGGACTATAAGGACCACGACGGAGACTACAAGGATCATGATATTGATT
ACAAAGACGATGACGATAAGATGGCCCCAAAGAAGAAGCGGAAGGTCGG
TATCCACGGAGTCCCAGCAGCCGACAAGAAGTACAGCATCGGCCTGgcc
ATCGGCACCAACTCTGTGGGCTGGGCCGTGATCACCGACGAGTACAAGG
TGCCCAGCAAGAAATTCAAGGTGCTGGGCAACACCGACCGGCACAGCAT
CAAGAAGAACCTGATCGGAGCCCTGCTGTTCGACAGCGGCGAAACAGCC
GAGGCCACCCGGCTGAAGAGAACCGCCAGAAGAAGATACACCAGACGGA
AGAACCGGATCTGCTATCTGCAAGAGATCTTCAGCAACGAGATGGCCAA
GGTGGACGACAGCTTCTTCCACAGACTGGAAGAGTCCTTCCTGGTGGAA
GAGGATAAGAAGCACGAGCGGCACCCCATCTTCGGCAACATCGTGGACG
AGGTGGCCTACCACGAGAAGTACCCCACCATCTACCACCTGAGAAAGAA
ACTGGTGGACAGCACCGACAAGGCCGACCTGCGGCTGATCTATCTGGCC
CTGGCCCACATGATCAAGTTCCGGGGCCACTTCCTGATCGAGGGCGACC
TGAACCCCGACAACAGCGACGTGGACAAGCTGTTCATCCAGCTGGTGCA
GACCTACAACCAGCTGTTCGAGGAAAACCCCATCAACGCCAGCGGCGTG
GACGCCAAGGCCATCCTGTCTGCCAGACTGAGCAAGAGCAGACGGCTGG -continued

```
AAAATCTGATCGCCCAGCTGCCCGGCGAGAAGAAGAATGGCCTGTTCGG

AAACCTGATTGCCCTGAGC.
```

The substituted aspartate to alanine is highlighted in bold and underlined.
Target (Spacer) Sequence Cloning The target spacer sequence can be cloned into the above CRISPR/Cas vector system via the BbsI restriction sites located upstream of the chimeric guided RNA sequence. The spacer sequence can be ordered as oligo pairs and annealed together with overhangs as shown below to allow direct cloning into BbsI linearised CRISPR/Cas vector using standard molecular biology protocols.

Sequence of an example oligo pair with spacer sequence:

```
                                       (SEQ ID NO: 15)
5'-CACCGNNNNNNNNNNNNNNNNNNNN-3'.

(SEQ ID NO: 16)
3'-CNNNNNNNNNNNNNNNNNNNNCAAA-5'.
```

The 4 bp overhang sequence underlined is required to be included in the spacer oligos to facilitate cloning into the BbsI restriction site in the CRISPR/Cas vector. Using this approach, any spacer sequence can be conveniently cloned into the CRISPR/Cas vector.
Reconstructing CRISPR/Cas System for One-Step Generation of Transgenic Animals In order to reconstitute a CRISPR/Cas system for one-step generation of transgenic animal as described in Wang et al (Wang H, Yang H, Shivalila C S, Dawlaty M M, Cheng A W, Zhang F, Jaenisch R: One-step generation of mice carrying mutations in multiple genes by CRISPR/Cas-mediated genome engineering. *Cell* 2013, 153(4):910-918) where direct embryo injection is used, the above detailed CRISPR/Cas vector system needs to be modified to incorporate a T7 polymerase promoter to the Cas9 coding sequence. In addition, the gRNA needs to be removed and synthetised separately by annealing oligos or produced synthetically (See below for an example T7-spacer sequence fused to chimeric guided RNA sequence-T7-gRNA). Note, ideally the spacer sequence will be designed in a unique region of a given chromosome to minimise off-target effect and also the respective protospacer genomic sequence needs to have a PAM at the 3'-end.

Example T7-gRNA Sequence

```
                                       (SEQ ID NO: 17)
TTAATACGACTCACTATAGGNNNNNNNNNNNNNNNNNNNNGTTTTAGAGC
TAGAAATAGCAAGTTAAAATAAGGCTAGTCCGTTATCAACTTGAAAAAGT
GGCACCGAGTCGGTGCTTTTTT.
```

The underlined 20 bp of N's depicts the spacer sequence for a given target DNA.

To reconstruct the one-step CRISPR/Cas system, the above detailed DNA fragments (Fragments 2, 3, 4, 5, 6 & 7) can be assembled together where fragment 1A (containing 45 bp homology to pBlueScript KS+ vector 5' to the EcoRV restriction site, human U6 promoter, BbsI restriction sites, chimeric guided RNA sequence and chicken b-actin promoter) is replaced with fragment 1, which only contains 45 bp homology to pBlueScript KS+ vector and the DNA sequence for T7 polymerase promoter with 45 bp homology to fragment 2. This will create the nuclease version of the CRISPR/Cas system for one-step generation of transgenic animals. To create the nickase version, fragment 2 can be replaced with fragment 2A as detailed above and then fragments 1, 2A, 3, 4, 5, 6 and 7 can be assembled together either by Gibson assembly or by assembly PCR.

Fragment 1 (111 bp)

```
                                       (SEQ ID NO: 18)
GGTACCGGGCCCCCCCTCGAGGTCGACGGTATCGATAAGCTTGATAATAC
GACTCACTATAGGGAGAATGGACTATAAGGACCACGACGGAGACTACAAG
GATCATGATATT.
```

Preparation of Oligo/DNA Fragments for HDR-Mediated Repair

DNA oligos ranging from 15 bp and upwards in excess of >125 bp will be synthetised through Sigma Custom Oligo synthesis Service. The oligos can contain any sequence such as a defined mutation, introduced restriction sites or a sequence of interest including recombination recognition sequence such as loxP or derivatives thereof, Frt and derivatives thereof or PiggyBac LTR or any other transposon elements or regulatory elements including enhancers, promoter sequence, reporter gene, selection markets and tags. The oligo design will incorporate DNA homology to the region where Cas9 mediates double-stranded DNA break or DNA nick. The size of the homology will range from a few base pairs (2-5 bp) to upwards and in excess of 80 bp. Larger DNA fragments (>100 bp ranging up to several kilobases) will be prepared either synthetically (GeneArt) or by PCR. The DNA fragment will be synthetised either with or without flanked NLS or only with a single NLS and either with or without a promoter (e.g., T7 polymerase promoter). The DNA can be prepared as a single stranded DNA fragment using either the capture biotinylated target DNA sequence method (Invitrogen: DYNABEADS M-270 Streptavidin) or any other standard and established single stranded DNA preparation methodology. The single stranded DNA can be prepared for microinjection by IVT as described above and the mRNA co-injected with Cas9 mRNA and gRNA. The DNA fragment can also be co-injected as a double stranded DNA fragment. The DNA fragment will be flanked by DNA homology to the site where Cas9 mediates double-stranded DNA break or DNA nick. The DNA homology can range from a few base pairs (2-5 bp) and up to or in excess of several kilobases. The DNA fragment can be used to introduce any endogenous or exogenous DNA.

HDR-mediated repair can also be done in ES cells following CRISPR/Cas-mediated DNA cleavage. The above mentioned donor oligo or DNA fragment can be co-transfected into ES cells along with the CRISPR/Cas expression vector.

Production of Cas9 mRNA and gRNA

Vector containing the T7 polymerase promoter with the coding region of humanised Cas9 will be PCR amplified using oligos Cas9-F and Cas9-R. The T7-Cas9 PCR product can be gel extracted and the DNA purified using Qiagen gel extraction kit. The purified T7-Cas9 DNA will be used for in vitro transcription (IVT) using mMESSAGE mMACHINE T7 Ultra Kit (Life Technologies Cat No. AM1345). The vector containing the T7-gRNA can be PCR amplified using oligos gRNA-F and gRNA-R and once again the PCR products gel purified. IVT of the T7-gRNA will be carried out using MEGAshortscript T7 Kit (Life Technologies Cat No. AM1354) and the gRNA purified using MEGAclear Kit (Life Technologies Cat No. AM19081 and eluted in RNase-free water.

```
Cas9-F:
                                 (SEQ ID NO: 19)
TTAATACGACTCACTATAGG

Cas9-R:
                                 (SEQ ID NO: 20)
GCGAGCTCTAGGAATTCTTAC gRNA-F:
                                 (SEQ ID NO: 21)
TTAATACGACTCACTATAGG gRNA-R:
                                 (SEQ ID NO: 22)
AAAAAAGCACCGACTCGGTGCCAC
```

ES Cell Transfection Procedure

Mouse embryonic stem cells AB2.1 and derivatives of this line will be used for transfecting the mammalian codon optimised Cas9 and sgRNA from a single expression vector or from separate vectors if desired. AB2.1 ES cells will be cultured on a PSNL76/7/4 MEF feeder layer in M-15: Knockout DMEM (Gibco, no pyruvate, high glucose, 15% FBS, 1xGPS, 1xBME) with standard ES cell culturing techniques. Transfection of CRISPR/Cas expression vector along with the optional addition of a donor oligo or DNA fragment will be done by electroporation using the Amaxa 4D-Nucleofector® Protocol (Lonza). A plasmid expressing PGK-Puro will also be optionally co-transfected to promote transfection efficiency. After transfection ES cells will be plated back onto feeder plates and Puromycin (2 µg/ml) will be added 72 hours post transfection for 7 days after which colonies will be picked and genotyped by PCR. Positive colonies will be further cultured and expanded on feeder layer and selection markers where necessary will be excised using a PiggyBac transposon system. This will be done by electroporation of ES cells with a plasmid containing HyPbase using the Amaxa 4D-Nucleofector® Protocol (Lonza). The ES cell will be plated back onto feeder plates. ES cells will be passaged 2-3 days post transfection and after a further 2-3 days the ES cells will be plated out at different cells densities (1:10, 1:20, 1:100 and 1:300) and FIAU (2 µg/ml) selection will be added 24 hours after replating. Colonies will be picked and analysed by PCR genotyping after 7-10 days on selection media. Positive clones will be further cultured and expanded on feeder layer and sent for zygote (blastocyst) microinjection.

Microinjection of Mouse Zygotes

Materials and Reagents
  M2 (Sigma M7167)
  Embryo Max KSOM (Speciality media MR-020P-F)
  Hyaluronidase (Sigma H4272)
  Mineral Oil (Sigma, M-8410)
Possible Donor Strains:
  S3F/S3F;KF3/KF3
  S3F/S3F;K4/K4
  S7F/S7F
  K5F/K5F Preparation of Zygotes and Microinjection:

The protocol is as described in: A. Nagy Et al. Manipulating the Mouse Embryo 3$^{rd}$ Edition. Chapter 7, Protocols 7-1, 7-6, 7-10, 7-11. Cold Spring Harbor Laboratory Press.
In brief:
1. Zygotes are harvested from E0.5 dpc (day post-coitum) superovulated female mice.
2. The zygotes are incubated in hyaluronidase to disperse cumulus cells.
3. Zygotes are collected and transferred to several drops of M2 medium to rinse off the hyaluronidase solution and debris. Zygotes are placed into KSOM Media and incubated at 37° C., 5% $CO_2$ until required.
4. Zygote quality is assessed and zygotes with normal morphology are selected for injection, these are placed in KSOM media and incubated at 37° C., 5% $CO_2$ until required.

Microinjection Set Up:

Injection procedures are performed on a Nikon Eclipse Ti inverted microscope with Eppendorf micromanipulators and an Eppendorf femtojet injection system. A slide is prepared by adding a large drop ~200 microlitres of M2 into the centre.

Microinjection:

Place an appropriate number of zygotes onto the slide. Examine the zygotes and select only those with normal morphology (2 distinct pronuclei are visible). Whilst holding a zygote with a male pronucleus closest to the injection pipette, carefully push the injection pipette through the zona pellucida into the pronucleus, apply injection pressure, the pronucleus should visibly swell, remove the injection pipette quickly. The injected zygote can be placed down while the rest are injected.

At the end of the injection session all viable injected zygotes should be placed into prepared dishes containing drops of KSOM and incubated until ready to surgically implant. They are incubated for 2-3 hours before surgically implanting into pseudo pregnant females. Pups will be born 21 days later.

Example 6

Single Copy Cas9 Expression in ES Cells

Figure 7:
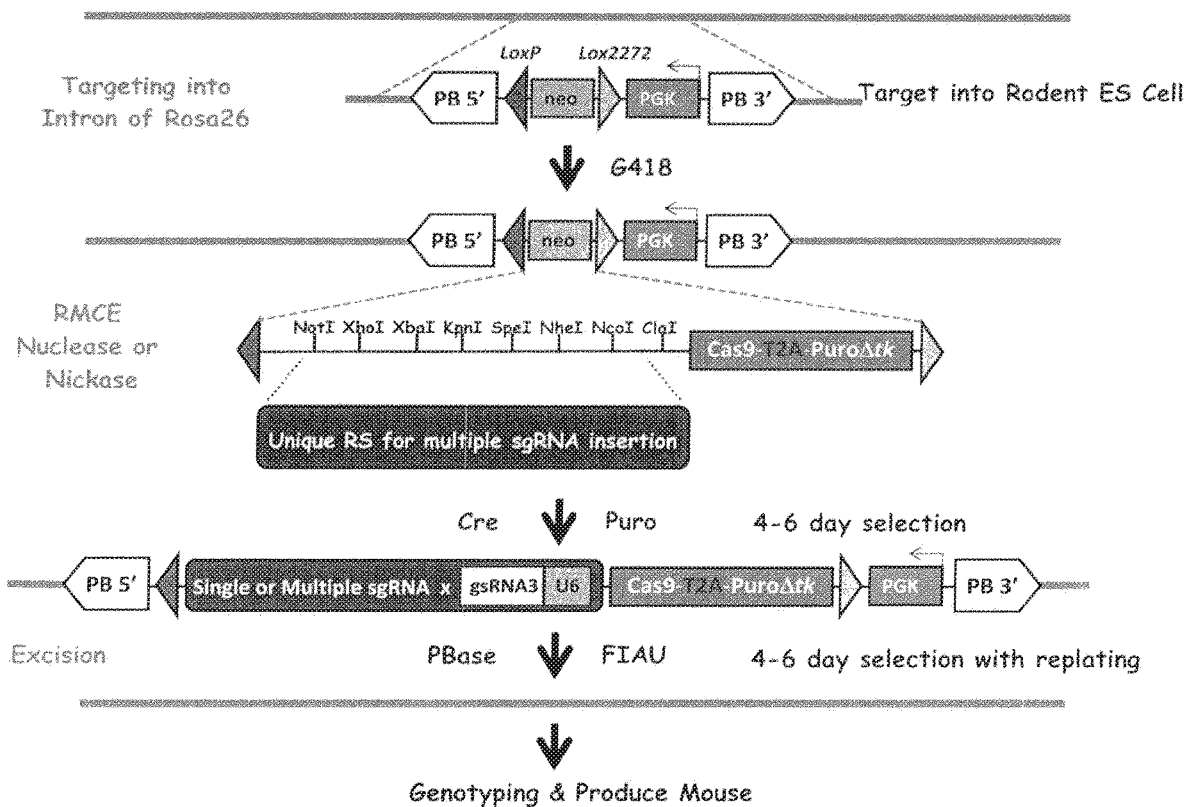
FIG. 7 depicts a schematic of genome modification to produce transposon-excisable Cas9 and gRNA

Reference is made to FIG. 7.

1. A landing pad consisting of a PiggyBac transposon element with the following features will be targeted into mouse ES cells (e.g., 129-derived ES cells, such as AB2.1 ES cells; Baylor College of Medicine, Texas, USA) and selected for on G418. The PiggyBac transposon element will contain neomycin resistance gene flanked by loxP and lox2272. It will also have a geneless PGK promoter. In this example, the landing pad will be targeted into the introgenic region of Rosa26 gene located on chromosome 6, but it could be targeted elsewhere. Targeting this landing pad in the Rosa26 gene will provide a universal ES cell line for precisely inserting any desired DNA fragment including DNA fragments containing Cas9, mutant Cas9 or any other gene of interest via RMCE with high efficiency. Targeting Rosa26 is beneficial since the targeted construct will be inserted as a single copy (unlike random integration elsewhere) and is unlikely to produce an unwanted phenotypic effect.

Note. This landing pad can be inserted into any gene in any chromosome or indeed in any eukaryotic or mammalian cell line, e.g., a human, insect, plant, yeast, mouse, rat, rabbit, rodent, pig, dog, cat, fish, chicken or bird cell line, followed by generation of the respective transgenic organism expressing Cas9.

Rosa 26 Locus

Ubiquitous expression of transgene in mouse embryonic stem cell can be achieved by gene targeting to the ROSA26 locus (also known as: gene trap ROSA 26 or Gt(ROSA)26) by homologous recombination (Ref. (a) and (b) below). The genomic coordinates for mouse C57BL/6J Rosa26 gene based on Ensemble release 73-September 2013 is: Chromosome 6: 113,067,428-113,077,333; reverse strand.

The Rosa26 locus can also be used to as a recipient location to knock-in a transgene. In our example we have use the Rosa26 locus to knock-in the landing pad vector by targeting through homologous recombination into the intronic region located between exons 2 and 3 of mouse strain 129-derived embryonic stem cells using approx. 3.1 kb homology arms. The homology arms were retrieved by recombineering from a BAC Clone generated from mouse strain 129. The sequence of the Rosa26 homology arms used for targeting is given below.

```
Sequence of Rosa26 5' homology arm
                                         (SEQ ID NO: 23)
CACATTTGGTCCTGCTTGAACATTGCCATGGCTCTTAAAGTCTTAATTAA

GAATATTAATTGTGTAATTATTGTTTTTCCTCCTTTAGATCATTCCTTGA

GGACAGGACAGTGCTTGTTTAAGGCTATATTTCTGCTGTCTGAGCAGCAA

CAGGTCTTCGAGATCAACATGATGTTCATAATCCCAAGATGTTGCCATTT

ATGTTCTCAGAAGCAAGCAGAGGCATGATGGTCAGTGACAGTAATGTCAC

TGTGTTAAATGTTGCTATGCAGTTTGGATTTTTCTAATGTAGTGTAGGTA

GAACATATGTGTTCTGTATGAATTAAACTCTTAAGTTACACCTTGTATAA

TCCATGCAATGTGTTATGCAATTACCATTTTAAGTATTGTAGCTTTCTTT

GTATGTGAGGATAAAGGTGTTTGTCATAAAATGTTTTGAACATTTCCCCA

AAGTTCCAAATTATAAAACCACAACGTTAGAACTTATTTATGAACAATGG

TTGTAGTTTCATGCTTTTAAAATGCTTAATTATTCAATTAACACCGTTTG

TGTTATAATATATAAAACTGACATGTAGAAGTGTTTGTCCAGAACATT

TCTTAAATGTATACTGTCTTTAGAGAGTTTAATATAGCATGTCTTTTGCA

ACATACTAACTTTTGTGTTGGTGCGAGCAATATTGTGTAGTCATTTTGAA

AGGAGTCATTTCAATGAGTGTCAGATTGTTTTGAATGTTATTGAACATTT

TAAATGCAGACTTGTTCGTGTTTTAGAAAGCAAAACTGTCAGAAGCTTTG

AACTAGAAATTAAAAAGCTGAAGTATTTCAGAAGGGAAATAAGCTACTTG

CTGTATTAGTTGAAGGAAAGTGTAATAGCTTAGAAAATTTAAAACCATAT

AGTTGTCATTGCTGAATATCTGGCAGATGAAAAGAAATACTCAGTGGTTC

TTTTGAGCAATATAACAGCTTGTTATATTAAAAATTTTCCCCACAGATAT

AAACTCTAATCTATAACTCATAAATGTTACAAATGGATGAAGCTTACAAA

TGTGGCTTGACTTGTCACTGTGCTTGTTTTAGTTATGTGAAAGTTTGGCA

ATAAACCTATGTCCTAAATAGTCAAACTGTGGAATGACTTTTTAATCTAT

TGGTTTGTCTAGAACAGTTATGTTGCCATTTGCCCTAATGGTGAAAGAAA

AAGTGGGGAGTGCCTTGGCACTGTTCATTTGTGGTGTGAACCAAAGAGGG

GGGCATGCACTTACACTTCAAACATCCTTTTGAAAGACTGACAAGTTTGG

GTCTTCACAGTTGGAATTGGGCATCCCTTTTGTCAGGGAGGGAGGGAGGG

AGGGAGGCTGGCTTGTTATGCTGACAAGTGTGATTAAATTCAAACTTTGA

GGTAAGTTGGAGGAACTTGTACATTGTTAGGAGTGTGACAATTTGGACTC

TTAATGATTTGGTCATACAAAATGAACCTAGACCAACTTCTGGAAGATGT

ATATAATAACTCCATGTTACATTGATTTCACCTGACTAATACTTATCCCT

TATCAATTAAATACAGAAGATGCCAGCCATCTGGGCCTTTTAACCCAGAA

ATTTAGTTTCAAACTCCTAGGTTAGTGTTCTCACTGAGCTACATCCTGAT

CTAGTCCTGAAAATAGGACCACCATCACCCCCAAAAAAATCTCAAATAAG

ATTTATGCTAGTGTTTCAAAATTTTAGGAATAGGTAAGATTAGAAAGTTT

TAAATTTTGAGAAATGGCTTCTCTAGAAAGATGTACATAGTGAACACTGA

ATGGCTCCTAAAGAGCCTAGAAAACTGGTACTGAGCACACAGGACTGAGA

GGTCTTTCTTGAAAAGCATGTATTGCTTTACGTGGGTCACAGAAGGCAGG

CAGGAAGAACTTGGGCTGAAACTGGTGTCTTAAGTGGCTAACATCTTCAC

AACTGATGAGCAAGAACTTTATCCTGATGCAAAAACCATCCAAACAAACT

AAGTGAAAGGTGGCAATGGATCCCAGGCTGCTCTAGAGGAGGACTTGACT

TCTCATCCCATCACCCACACCAGATAGCTCATAGACTGCCAATTAACACC

AGCTTCTAGCCTCCACAGGCACCTGCACTGGTACACATAATTTCACACAA

ACACAGTAAGAAGCCTTCCACCTGGCATGGTATTGCTTATCTTTAGTTCC

CAACACTTGGGAGGCAGAGGCCAGCCAGGGCTATGTGACAAAAACCTTGT

CTAGAGGAGAAACTTCATAGCTTATTTCCTATTCACGTAACCAGGTTAGC

AAAATTTACCAGCCAGAGATGAAGCTAACAGTGTCCACTATATTTGTAGT

GTTTTAAGTCAATTTTTTAAATATACTTAATAGAATTAAAGCTATGGTGA

ACCAAGTACAAACCTGGTGTATTAACTTGAGAACTTAGCATAAAAAGTAG

TTCATTTGTTCAGTAAATATTAAATGCTTACTGGCAAAGATTATGTCAGG

AACTTGGTAAATGGTGATGAAACAATCATAGTTGTACATCTTGGTTCTGT

GATCACCTTGGTTTGAGGTAAAAGTGGTTCCTTTGATCAAGGATGGAATT

TTAAGTTTATATTCAATCAATAATGTATTATTTTGTGATTGCAAAATTGC

CTATCTAGGGTATAAAACCTTTAAAAATTTCATAATACCAGTTCATTCTC

CAGTTACTAATTCCAAAAAGCCACTGACTATGGTGCCAATGTGGATTCTG

TTCTCAAAGGAAGGATTGTCTGTGCCCTTTATTCTAATAGAAACATCACA

CTGAAAATCTAAGCTGAAAGAAGCCAGACTTTCCTAAATAAATAACTTTC

CATAAAGCTCAAACAAGGATTACTTTTAGGAGGCACTGTTAAGGAACTGA

TAAGTAATGAGGTTACTTATATAATGATAGTCCCACAAGACTATCTGAGG

AAAAATCAGTACAACTCGAAAACAGAACAACCAGCTAGGCAGGAATAACA

GGGCTCCCAAGTCAGGAGGTCTATCCAACACCCTTTTCTGTTGAGGGCCC

CAGACCTACATATTGTATACAAACAGGGAGGTGGGTGATTTTAACTCTCC

TGAGGTAC

Sequence of Rosa26 3' homology arm
                                         (SEQ ID NO: 24)
CTTGGTAAATCTTTGTCCTGAGTAAGCAGTACAGTGTACAGTTTACATTT

TCATTTAAAGATACATTAGCTCCCTCTACCCCCTAAGACTGACAGGCACT

TTGGGGGTGGGAGGGCTTTGGAAAATAACGCTTCCATACACTAAAAGAG

AAATTTCTTTAATTAGGCTTGTTGGTTCCATACATCTACTGGTGTTTCTA

CTACTTAGTAATATTATAATAGTCACACAAGCATCTTTGCTCTGTTTAGG

TTGTATATTTATTTTAAGGCAGATGATAAAACTGTAGATCTTAAGGGATG

CTTCTGCTTCTGAGATGATACAAAGAATTTAGACCATAAAACAGTAGGTT

GCACAAGCAATAGAATATGGCCTAAAGTGTTCTGACACTTAGAAGCCAAG

CAGTGTAGGCTTCTTAAGAAATACCATTACAATCACCTTGCTAGAAATCA
```

-continued
```
AGCATTCTGGAGTGGTCAAGCAGTGTAACCTGTACTGTAAGTTACTTTTC

TGCTATTTTTCTCCCAAAGCAAGTTCTTTATGCTGATATTTCCAGTGTTA

GGAACTACAAATATTAATAAGTTGTCTTCACTCTTTTCTTTACCAAGGAG

GGTCTCTTCCTTCATCTTGATCTGAAGGATGAACAAAGGCTTGAGCAGTG

CGCTTTAGAAGATAAACTGCAGCATGAAGGCCCCCGATGTTCACCCAGAC

TACATGGACCTTTCGCCACACATGTCCCATTCCAGATAAGGCCTGGCACA

CACAAAAAACATAAGTCATTAGGCTACCAGTCTGATTCTAAAACAACCTA

AAATCTTCCCACTTAAATGCTATGGGTGGTGGGTTGGAAAGTTGACTCAG

AAAATCACTTGCTGTTTTTAGAGAGGATCTGGGTTCAGTTTCTGATACAT

TGTGGCTTACAACTATAACTCCAGTTCTAGGGGGTCCATCCAACATCCTC

TTCTGTTGAGGGCACCAAATAAATGTATTGTGTACAAACAGGGAGGTGAG

TGATTTAACTCTCGTGTATAGTACCTTGGTAAAACATTTCTTGTCCTGAG

TAAGCAGTACAGCTCTGCCTGTCCCTGGTCTACAGACACGGCTCATTTCC

CGAAGGCAAGCTGGATAGAGATTCCAATTTCTCTTCTTGGATCCCATCCT

ATAAAAGAAGGTCAAGTTTAATCTATTGCAAAAGGTAAATAGGTAGTTTC

TTACATGAGACAAGAACAAATCTTAGGTGTGAAGCAGTCATCTTTTACAG

GCCAGAGCCTCTATTCTATGCCAATGAAGGAAACTGTTAGTCCAGTGTTA

TAGAGTTAGTCCAGTGTATAGTTTTCTATCAGAACACTTTTTTTTTAAAC

AACTGCAACTTAGCTTATTGAAGACAAACCACGAGTAGAAATCTGTCCAA

GAAGCAAGTGCTTCTCAGCCTACAATGTGGAATAGGACCATGTAATGGTA

CAGTGAGTGAAATGAATTATGGCATGTTTTTCTGACTGAGAAGACAGTAC

AATAAAAGGTAAACTCATGGTATTTATTTAAAAAGAATCCAATTTCTACC

TTTTTCCAAATGGCATATCTGTTACAATAATATCCACAGAAGCAGTTCTC

AGTGGGAGGTTGCAGATATCCCACTGAACAGCATCAATGGGCAAACCCCA

GGTTGTTTTCTGTGGAGACAAAGGTAAGATATTTCAATATATTTTCCCA

AGCTAATGAGATGGCTCAGCAAATAATGGTACTGGCCATTAAGTCTCATG

ACCTGAGCTTGATCCTCAGGGACCATGTGGTACAAGGAGAGACCTAAATC

CTTCAGTTGGACTTCAATCTTCTACCCTCATGTCCACACACAAATAAATA

CAATAAAAAACATTCTGCAGTCTGAATTTCTAAAGGTTGTTTTTCTAAAA

AGAAATGTTAAAGTAACATAGGAAGAAATATGTCCATAACTGAAATACAA

GTTTTTAAATGGTTAAGACTGGTTTTCAAAGGATGTATGGTTAAGAAAA

TACCAGGGAAAATGAGCTTACATGTAAAAAAGTGTCTAAAAGGCCAGAGA

AATGACCCAGCTGGCAAAGGTGTCTGCCCTAAGCCAGACAAAAGGAATTT

GATTCACAGGAAGAAGAGACCCAACTCTCACTAGTTATCCTCTGACTTCC

ACACCATGACACAGCTCCATGGCACTCTCAGGCCCCCACACATATACAGA

TATAAACAGAAACCTAATCCACCAGCCTTCAGAAGCAAAGCAATTGGAGG

ATTTAAACAGGCCATGGCTACTAATAGAGATAACTGGTAGTTTAAAAGTT

ATGGTAATGACTTTCATGCTTCTTTCAACTCATATTGTTCTAAATAATTA

ATTTGGTTTTTCAAGGCAGGGTTTCTCTGTGTAGTTCTGGCTGTCCTGGA

ACTCACTCTGTAGACCAGGCTGGCCTTGAACTCAGATCCATCTGCCTCTG

GAATAAGGGCACGTGCGTGCCTTTTCTACATAACAAAACCTATACTATAA

CAAAACCTATACCATACTGTACCGTTTTGGGAAAAGACAAAAAATAATGA

ACAAAAAAGGAGAAATAACATTCCAATAAAGTATGGAAATGGTAGTTAAA

TTAATTACAAATGTTTTTCAGTAAATTAGATGTGACTTCTCATACTGTTC

ATTTGGCTATAATGATACCACAAAGCACTGGGGGTGAATAATAATTCCAA

GTCAGTAGGGAGAGAGACTTGAAAAGATGCAATGCAATCATTGAAGTTAA

ACTTACCCATCTTTAATCTGGCTCTTAGTCAATAGAGATGAGATGTTATT

TGCTGCTCTGTTCACTGCCAGTGGGTTATTGTCCCCAGCAATATGGTAAC

AGTGAGACCACTCAGTAGCCCCCTATGAGACAGGAGTGTTGGTTAAACAT

GCCACAAGAGAAAAGGGAAAAGTCACTATGGCCAACTCTCAGTAACATGG

CAATCCGTGCCATTCATTTCCTTGCCAGAAATGTCTTCCCTGTTCTTCTG

CCTACTGAACTTTCACCCACTAGAAATGTGGCTCCAATGTCATCCACTAT

GACATCAATGTCAGCGCTAGAAGCACTTTGCACACCTCTGTTGCTGACTT

AG
```

REFERENCE a) Pablo Perez-Pinera, David G. Ousterout, Matthew T. Brown and Charles A. Gersbach (2012) Gene targeting to the ROSA26 locus directed by engineered zinc finger nucleases. Nucleic Acids Research, 2012, Vol. 40, No. 8 3741-3752
b) Peter Hohenstein, Joan Slight, Derya Deniz Ozdemir, Sally F Burn, Rachel Berry and Nicholas D Hastie (2008) High-efficiency Rosa26 knock-in vector construction for Cre-regulated overexpression and RNAi. *PathoGenetics* 2008, 1:3

2. A recombinase mediated cassette exchange (RMCE)-enabled vector containing a promoterless puromycin-delta-tk with in-frame fusion of T2A at the C-terminus following by either Cas9 or mutant Cas9 nucleotide sequence and a series of unique restriction sites flanked by loxP and lox2272 will allow for the direct targeting of this vector into the landing pad by Cre-mediated RMCE. As is known, T2A allows ribosomal skipping during translation. The insertion of the coding sequence of T2A between two genes results in two products (one gene, one transcript but two proteins expressed, in this case the Cas9 and selection marker). ES clones containing the correctly inserted DNA fragment can be directly selected on puromycin. This approach also advantageously ensures single copy expression of Cas9 as suppose to a random integration or transient expression approach. Insertion of the RMCE enabled vector into the desired locus containing the landing pad can be selected directly as the PGK promoter in the landing pad will drive the transcription of the promoterless Puro-Delta-Tk and Cas9. Since the Puro-delta-Tk is in the same transcriptional unit as Cas9, ES clones selected on puromycin will ensure expression of Cas9.
3. The above strategy allows for three separate approaches to express the sgRNA designed for disrupting (mutation through indel formation, deletion or deletion followed by insertion) gene of interest.
   a. The above ES cell line containing Cas9 can be used for generating transgenic mice with either constitutively expressed Cas9 or modified for inducible Cas9 expression or indeed tissue specific Cas9 expression for example expression of Cas9 at an embryo stage using Nanog-, Pou5f1- or SoxB promoter-specifc Cas9 expression. Such derived mouse line expressing Cas9 can be used for genome editing in a streamline fashion whereby in vitro transcribed sgRNA can be easily injected into embryos obtained from such transgenic mice. This will enhance the efficiency of generating mouse lines with the desired homozygous genotype and thus will dramatically reduce the number of animals required.

b. sgRNA can be transfected directly into the ES cells expressing Cas9 and thus avoids the requirement for cloning into the RMCE enabled vector single or multiple sgRNA. This approach will allow multiple sgRNA to be inserted into the ES cells simultaneously very rapidly.

c. Multiple sgRNA can be cloned directly into the multiple cloning site of the RMCE enabled vector (i.e., using a plurality of different restriction endonuclease sites) to allow single copy expression of the guide-RNA. This approach may be useful for limiting off-target effects particularly relevant for those genes with high sequence homology within the genome.

4. ES cells expressing Cas9 and sgRNA can be selected for directly on medium containing puromycin. Selection on puromycin for 4-6 days will allow for the desired location to be mutated or disrupted and the advantage of manipulating ES cells is that individual clones can be analysed by PCR followed by sequencing for the desired mutation. Only correctly mutated ES cell clones can be processed further whereby inserted DNA element introduced through insertion of the landing pad and the subsequent insertion of the RMCE vector can be completely removed leaving the ES cell devoid of any alteration other than the intended mutation induced by the action of Cas9 and the sgRNA. This can be done through transiently expressing PBase transposon followed by selection on FIAU. Removal of the constitutively expressed Cas9 with only the minimal length of time required to induce mutation in the presence of sgRNA will reduce or eliminate the possibility of Cas9 inducing unwanted mutations.

5. ES Clones containing the desired mutation can be injected into blastocyst to generate transgenic mice.

In Table 1, sequence identification numbers for sequences from top to bottom in the column under the header "CRISPR Consensus sequences" are SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37. The sequence identification numbers for sequences from top to bottom in the column under the header "Leaders" are SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60 and SEQ ID NO: 61.

TABLE 1

PAM conservation in repeats and leaders for various CRISPR types (reproduced from Short motif sequences determine the targets of the prokaryotic CRISPR defence system F. J. M. Mojica, C. Díez-Villaseñor, J. García-Martínez, C. Almendros Microbiology (2009), 155, 733-740)

| Genomes* | PAM | CRISPR Consensus† | Leaders‡ |
|---|---|---|---|
| Group 1 | | | |
| Mth | NGG | ATTTCAATCCCATTTTGGTCTGATTTTAAC | AGGGCGGATT |
| | | | ATGGCCAATT |
| Lmo | WGG | ATTTACATTTCAHAATAAGTARYTAAAAC | CCACTAACTT |
| | | | CCGCTCTATT |
| Group 2 | | | |
| Eco | CWT | CGGTTTATCCCCGCTGGCGCGGGAACWU | TCTAAACATA |
| | | | TCTAAAAGTA |
| Pae | CTT | CGGTTCATCCCCACRCMYGTGGGGAACAC | ACTTACCGTA |
| | | | CCTTACCGTA |
| Group 3 | | | |
| Spy | GAA | ATTTCAATCCACTCACCCATGAAGGGTGAGAC | TGCGCCAAAT |
| Xan | GAA | GTTTCAATCCACGCGCCCGTGAGGRCGCGAC | CCCCCCTTAG |
| | | | GCCGCCAGCA |
| Group 4 | | | |
| She | GG | TTTCTAAGCCGCCTGTGCGGCGGTGAAC | AATAGCTTAT |
| | | | TGTAGAATAA |
| Pae | GG | TTTCTTAGCTGCCTATACGGCAGTGAAC | TAGCTCCGAA |
| | | | TAGACCAAAA |
| Ype | GG | TTTCTAAGCTGCCTGTGCGGCGTGAAC | GTAAGATAAT |

TABLE 1-continued

PAM conservation in repeats and leaders for various CRISPR types (reproduced from Short motif sequences determine the targets of the prokaryotic CRISPR defence system F. J. M. Mojica, C. Díez-Villaseñor, J. García-Martínez, C. Almendros Microbiology (2009), 155, 733-740)

| Genomes* | PAM | CRISPR Consensus† | Leaders‡ |
|---|---|---|---|
| | | Group 7 | |
| Sso | NGG | CTTCAATTCTATAAGAGATTATC | TGAGGGTTTA |
| Mse | NGG | CTTTCAACTCTATAGGAGATTAAC | TGATACCTTT |
| | | | TGAAACTTTT |
| | | | TGACACTCTT |
| | | Group 10 | |
| Str | NGG | GTTTTAGAGCTATGCTGTTTTGAATGGTCCCAAAC | CTCGTAGACT |
| | | | CTCGTAGAAA |
| Lis | NGG | GTTTTAGAGCTATGTTATTTTGAATGCTAMCAAAAC | CTCGCAGAAT |
| | | | CTCGTAGAAT |

*Genomes are abbreviated according to the denominations of the species or genera carrying the corresponding CRISPR arrays: Mth, *M. thermautotrophicus*; Lmo, *L. monocytogenes*; Eco, *E. coli*; Pae, *P. aeruginosa*; Spy, *S. pyogenes*; Xan, *Xanthomonas* spp. She, *Shewanella* spp.; Ype, *Y. pestis*; Sso, *S. solfataricus*; Mse, *M. sedular*; Str, *Streptococcus* spp.; Lis, *Listeria* spp.

†Sequences matching the PAM are underlined.

‡Representative CRISPR array proximal leader sequences. Nucleotides matching the PAM are underlined.

TABLE 2

CRISPR-Associated Endonucleases
[Gene ID numbers refer to genes in the NCBI Gene Database as at September 2013; all sequence information relating to the gene IDs below is incorporated herein by reference for possible use in the present invention]

1. Plav_0099

CRISPR-associated endonuclease Csn1 family protein [*Parvibaculum lavamentivorans* DS-1]
Other Aliases: Plav_0099
Genomic context: Chromosome
Annotation: NC_009719.1 (105795 . . . 108908, complement)
ID: 5454634

2. FTN_0757 membrane protein [*Francisella novicida* U112]
Other Aliases: FTN_0757
Genomic context: Chromosome
Annotation: NC_008601.1 (810052 . . . 814941)
ID: 4548251

3. Cj1523c

CRISPR-associated protein [*Campylobacter jejuni* subsp. *jejuni* NCTC 11168 = ATCC 700819]
Other Aliases: Cj1523c
Genomic context: Chromosome
Annotation: NC_002163.1 (1456880 . . . 1459834, complement)
ID: 905809

4. mcrA restriction endonuclease [*Bifidobacterium longum* DJO10A]
Other Aliases: BLD_1902
Genomic context: Chromosome
Annotation: NC_010816.1 (2257993 . . . 2261556)
ID: 6362834

5. MGA_0519

Csn1 family CRISPR-associated protein [*Mycoplasma gallisepticum* str. R(low)]
Other Aliases: MGA_0519
Genomic context: Chromosome
Annotation: NC_004829.2 (919248 . . . 923060)
ID: 1089911

TABLE 2-continued

CRISPR-Associated Endonucleases
[Gene ID numbers refer to genes in the NCBI Gene Database as at September 2013; all sequence information relating to the gene IDs below is incorporated herein by reference for possible use in the present invention]

6. Emin_0243

CRISPR-associated endonuclease Csn1 family protein [*Elusimicrobium minutum* Pei191]
Other Aliases: Emin_0243
Genomic context: Chromosome
Annotation: NC_010644.1 (261119 . . . 264706)
ID: 6263045

7. FTW_1427

CRISPR-associated large protein [*Francisella tularensis* subsp. *tularensis* WY96-3418]
Other Aliases: FTW_1427
Genomic context: Chromosome
Annotation: NC_009257.1 (1332426 . . . 1335803, complement)
ID: 4958852

8. SMA_1444

CRISPR-associated protein, Csn1 family [*Streptococcus macedonicus* ACA-DC 198]
Other Aliases: SMA_1444
Annotation: NC_016749.1 (1418337 . . . 1421729, complement)
ID: 11601419

9. SSUST3_1318

CRISPR-associated protein, Csn1 family [*Streptococcus suis* ST3]
Other Aliases: SSUST3_1318
Genomic context: Chromosome
Annotation: NC_015433.1 (1323872 . . . 1327240, complement)
ID: 10491484

10. cas5

CRISPR-associated protein, Csn1 family [*Streptococcus gallolyticus* UCN34]
Other Aliases: GALLO_1439
Genomic context: Chromosome
Annotation: NC_013798.1 (1511433 . . . 1514825, complement)
ID: 8776949

11. GALLO_1446

CRISPR-associated protein [*Streptococcus gallolyticus* UCN34]
Other Aliases: GALLO_1446
Genomic context: Chromosome
Annotation: NC_013798.1 (1518984 . . . 1523110, complement)
ID: 8776185

12. csn1

CRISPR-associated endonuclease Csn1 [*Bifidobacterium dentium* Bd1]
Other Aliases: BDP_1254
Genomic context: Chromosome
Annotation: NC_013714.1 (1400576 . . . 1403992, complement)
ID: 8692053

13. NMO_0348 putative CRISPR-associated protein [*Neisseria meningitidis* alpha14]
Other Aliases: NMO_0348
Genomic context: Chromosome
Annotation: NC_013016.1 (369547 . . . 372795, complement)
ID: 8221228

14. csn1

CRISPR-Associated Protein Csn1 [*Streptococcus equi* subsp. *zooepidemicus* MGCS10565]
Other Aliases: Sez_1330
Genomic context: Chromosome
Annotation: NC_011134.1 (1369339 . . . 1373385, complement)
ID: 6762114

15. csn1

CRISPR-associated endonuclease Csn1 family protein [*Streptococcus gordonii* str. *Challis* substr. CH1]
Other Aliases: SGO_1381
Genomic context: Chromosome
Annotation: NC_009785.1 (1426750 . . . 1430160, complement)
ID: 5599802

TABLE 2-continued

CRISPR-Associated Endonucleases
[Gene ID numbers refer to genes in the NCBI Gene Database as at September 2013; all sequence information relating to the gene IDs below is incorporated herein by reference for possible use in the present invention]

---

16. M28_Spy0748 cytoplasmic protein [*Streptococcus pyogenes* MGAS6180]
Other Aliases: M28_Spy0748
Genomic context: Chromosome
Annotation: NC_007296.1 (771231 . . . 775337)
ID: 3573516

17. SGGBAA2069_c14690

CRISPR-associated protein [*Streptococcus gallolyticus* subsp. *gallolyticus* ATCC BAA-2069]
Other Aliases: SGGBAA2069_c14690
Genomic context: Chromosome
Annotation: NC_015215.1 (1520905 . . . 1525017, complement)
ID: 10295470

18. SAR116_2544

CRISPR-associated protein, Csn1 family [*Candidatus Puniceispirillum marinum* IMCC1322]
Other Aliases: SAR116_2544
Genomic context: Chromosome
Annotation: NC_014010.1 (2748992 . . . 2752099)
ID: 8962895

19. TDE0327

CRISPR-associated Cas5e [*Treponema denticola* ATCC 35405]
Other Aliases: TDE0327
Genomic context: Chromosome
Annotation: NC_002967.9 (361021 . . . 365208)
ID: 2741543

20. csn1

CRISPR-associated protein [*Streptococcus pasteurianus* ATCC 43144]
Other Aliases: SGPB_1342
Genomic context: Chromosome
Annotation: NC_015600.1 (1400035 . . . 1403427, complement)
ID: 10753339

21. cas9

CRISPR-associated protein [*Corynebacterium ulcerans* BR-AD22]
Other Aliases: CULC22_00031
Genomic context: Chromosome
Annotation: NC_015683.1 (30419 . . . 33112, complement)
ID: 10842578

22. MGAS2096_Spy0843 putative cytoplasmic protein [*Streptococcus pyogenes* MGAS2096]
Other Aliases: MGAS2096_Spy0843
Genomic context: Chromosome
Annotation: NC_008023.1 (813084 . . . 817190)
ID: 4066021

23. MGAS9429_Spy0885 cytoplasmic protein [*Streptococcus pyogenes* MGAS9429]
Other Aliases: MGAS9429_Spy0885
Genomic context: Chromosome
Annotation: NC_008021.1 (852508 . . . 856614)
ID: 4061575

24. AZL_009000

CRISPR-associated protein, Csn1 family [*Azospirillum* sp. B510]
Other Aliases: AZL_009000
Genomic context: Chromosome
Annotation: NC_013854.1 (1019522 . . . 1023028, complement)
ID: 8789261

25. EUBREC_1713 contains RuvC-like nuclease and HNH-nuclease domains [*Eubacterium rectale* ATCC 33656]
Other Aliases: EUBREC_1713
Other Designations: CRISPR-system related protein
Genomic context: Chromosome
Annotation: NC_012781.1 (1591112 . . . 1594456)
ID: 7963668

26. Alide2_0194

CRISPR-associated protein, Csn1 family [*Alicycliphilus denitrificans* K601]
Other Aliases: Alide2_0194

TABLE 2-continued

CRISPR-Associated Endonucleases
[Gene ID numbers refer to genes in the NCBI Gene Database as at September 2013;
all sequence information relating to the gene IDs below is incorporated herein by
reference for possible use in the present invention]

Genomic context: Chromosome
Annotation: NC_015422.1 (218107 . . . 221196)
ID: 10481210
27. Alide_0205 crispr-associated protein, csn1 family [*Alicycliphilus denitrificans* BC]
Other Aliases: Alide_0205
Genomic context: Chromosome
Annotation: NC_014910.1 (228371 . . . 231460)
ID: 10102228
28. STER_1477

CRISPR-system-like protein [*Streptococcus thermophilus* LMD-9]
Other Aliases: STER_1477
Genomic context: Chromosome
Annotation: NC_008532.1 (1379975 . . . 1384141, complement)
ID: 4437923
29. STER_0709

CRISPR-system-like protein [*Streptococcus thermophilus* LMD-9]
Other Aliases: STER_0709
Genomic context: Chromosome
Annotation: NC_008532.1 (643235 . . . 646600)
ID: 4437391
30. cas9

CRISPR-associated protein [*Corynebacterium diphtheriae* 241]
Other Aliases: CD241_2102
Genomic context: Chromosome
Annotation: NC_016782.1 (2245769 . . . 2248399)
ID: 11674395
31. cas3

CRISPR-associated endonuclease [*Corynebacterium diphtheriae* 241]
Other Aliases: CD241_0034
Genomic context: Chromosome
Annotation: NC_016782.1 (35063 . . . 38317)
ID: 11672999
32. Corgl_1738

CRISPR-associated protein, Csn1 family [*Coriobacterium glomerans* PW2]
Other Aliases: Corgl_1738
Genomic context: Chromosome
Annotation: NC_015389.1 (2036091 . . . 2040245)
ID: 10439994
33. Fluta_3147

CRISPR-associated protein, Csn1 family [*Fluviicola taffensis* DSM 16823]
Other Aliases: Fluta_3147
Genomic context: Chromosome
Annotation: NC_015321.1 (3610221 . . . 3614597, complement)
ID: 10398516
34. Acav_0267

CRISPR-associated protein, Csn1 family [*Acidovorax avenae* subsp. *avenae* ATCC 19860]
Other Aliases: Acav_0267
Genomic context: Chromosome
Annotation: NC_015138.1 (295839 . . . 298976)
ID: 10305168
35. NAL212_2952

CRISPR-associated protein, Csn1 family [*Nitrosomonas* sp. AL212]
Other Aliases: NAL212_2952
Genomic context: Chromosome
Annotation: NC_015222.1 (2941806 . . . 2944940, complement)
ID: 10299493
36. SpiBuddy_2181

CRISPR-associated protein, Csn1 family [*Sphaerochaeta globosa* str. Buddy]
Other Aliases: SpiBuddy_2181
Genomic context: Chromosome
Annotation: NC_015152.1 (2367952 . . . 2371491, complement)
ID: 10292274

TABLE 2-continued

CRISPR-Associated Endonucleases
[Gene ID numbers refer to genes in the NCBI Gene Database as at September 2013;
all sequence information relating to the gene IDs below is incorporated herein by
reference for possible use in the present invention]

37. Tmz1t_2411

HNH endonuclease [*Thauera* sp. MZ1T]
Other Aliases: Tmz1t_2411
Genomic context: Plasmid pTha01
Annotation: NC_011667.1 (75253 . . . 76200, complement)
ID: 7094333

38. Gdia_0342

Csn1 family CRISPR-associated protein [*Gluconacetobacter diazotrophicus* PAI 5]
Other Aliases: Gdia_0342
Genomic context: Chromosome
Annotation: NC_011365.1 (382737 . . . 385748)
ID: 6973736

39. JJD26997_1875

CRISPR-associated Cas5e family protein [*Campylobacter jejuni* subsp. *doylei* 269.97]
Other Aliases: JJD26997_1875
Genomic context: Chromosome
Annotation: NC_009707.1 (1656109 . . . 1659063, complement)
ID: 5389688

40. Asuc_0376

CRISPR-associated endonuclease Csn1 family protein [*Actinobacillus succinogenes* 130Z]
Other Aliases: Asuc_0376
Genomic context: Chromosome
Annotation: NC_009655.1 (431928 . . . 435116)
ID: 5348478

41. Veis_1230

CRISPR-associated endonuclease Csn1 family protein [*Verminephrobacter eiseniae* EF01-2]
Other Aliases: Veis_1230
Genomic context: Chromosome
Annotation: NC_008786.1 (1365979 . . . 1369185)
ID: 4695198

42. MGAS10270_Spy0886 putative cytoplasmic protein [*Streptococcus pyogenes* MGAS10270]
Other Aliases: MGAS10270_Spy0886
Genomic context: Chromosome
Annotation: NC_008022.1 (844446 . . . 848552)
ID: 4063984

43. gbs0911 hypothetical protein [*Streptococcus agalactiae* NEM316]
Other Aliases: gbs0911
Genomic context: Chromosome
Annotation: NC_004368.1 (945801 . . . 949946)
ID: 1029893

44. NMA0631 hypothetical protein [*Neisseria meningitidis* Z2491]
Other Aliases: NMA0631
Genomic context: Chromosome
Annotation: NC_003116.1 (610868 . . . 614116, complement)
ID: 906626

45. Ccan_14650 hypothetical protein [*Capnocytophaga canimorsus* Cc5]
Other Aliases: Ccan_14650
Genomic context: Chromosome
Annotation: NC_015846.1 (1579873 . . . 1584165, complement)
ID: 10980451

46. lpp0160 hypothetical protein [*Legionella pneumophila* str. Paris]
Other Aliases: lpp0160
Genomic context: Chromosome
Annotation: NC_006368.1 (183831 . . . 187949)
ID: 3118625

TABLE 2-continued

CRISPR-Associated Endonucleases
[Gene ID numbers refer to genes in the NCBI Gene Database as at September 2013; all sequence information relating to the gene IDs below is incorporated herein by reference for possible use in the present invention]

47. Cbei_2080 hypothetical protein [*Clostridium beijerinckii* NCIMB 8052]
Other Aliases: Cbei_2080
Genomic context: Chromosome
Annotation: NC_009617.1 (2422056 . . . 2423096)
ID: 5296367

48. MMOB0330 hypothetical protein [*Mycoplasma mobile* 163K]
Other Aliases: MMOB0330
Genomic context: Chromosome
Annotation: NC_006908.1 (45652 . . . 49362, complement)
ID: 2807677

49. MGF_5203

Csn1 family CRISPR-associated protein [*Mycoplasma gallisepticum* str. F]
Other Aliases: MGF_5203
Genomic context: Chromosome
Annotation: NC_017503.1 (888602 . . . 892411)
ID: 12397088

50. MGAH_0519

Csn1 family CRISPR-associated protein [*Mycoplasma gallisepticum* str. R(high)]
Other Aliases: MGAH_0519
Genomic context: Chromosome
Annotation: NC_017502.1 (918476 . . . 922288)
ID: 12395725

51. Smon_1063

CRISPR-associated protein, Csn1 family [*Streptobacillus moniliformis* DSM 12112]
Other Aliases: Smon_1063
Genomic context: Chromosome
Annotation: NC_013515.1 (1159048 . . . 1162827, complement)
ID: 8600791

52. Spy49_0823 hypothetical protein [*Streptococcus pyogenes* NZ131]
Other Aliases: Spy49_0823
Genomic context: Chromosome
Annotation: NC_011375.1 (821210 . . . 825316)
ID: 6985827

53. C8J_1425 hypothetical protein [*Campylobacter jejuni* subsp. *jejuni* 81116]
Other Aliases: C8J_1425
Genomic context: Chromosome
Annotation: NC_009839.1 (1442672 . . . 1445626, complement)
ID: 5618449

54. FTF0584 hypothetical protein [*Francisella tularensis* subsp. *tularensis* FSC198]
Other Aliases: FTF0584
Genomic context: Chromosome
Annotation: NC_008245.1 (601115 . . . 604486)
ID: 4200457

55. FTT_0584 hypothetical protein [*Francisella tularensis* subsp. *tularensis* SCHU S4]
Other Aliases: FTT_0584
Genomic context: Chromosome
Annotation: NC_006570.2 (601162 . . . 604533)
ID: 3191177

56. csn1

CRISPR-associated protein [*Streptococcus dysgalactiae* subsp. *equisimilis* RE378]
Other Aliases: GGS_1116
Annotation: NC_018712.1 (1169559 . . . 1173674, complement)
ID: 13799322

TABLE 2-continued

CRISPR-Associated Endonucleases
[Gene ID numbers refer to genes in the NCBI Gene Database as at September 2013; all sequence information relating to the gene IDs below is incorporated herein by reference for possible use in the present invention]

57. SMUGS5_06270

CRISPR-associated protein csn1 [*Streptococcus mutans* GS-5]
Other Aliases: SMUGS5_06270
Genomic context: Chromosome
Annotation: NC_018089.1 (1320641 . . . 1324678, complement)
ID: 13299050
58. Y1U_C1412

Csn1 [*Streptococcus thermophilus* MN-ZLW-002]
Other Aliases: Y1U_C1412
Genomic context: Chromosome
Annotation: NC_017927.1 (1376653 . . . 1380819, complement)
ID: 12977193
59. Y1U_C0633

CRISPR-system-like protein [*Streptococcus thermophilus* MN-ZLW-002]
Other Aliases: Y1U_C0633
Genomic context: Chromosome
Annotation: NC_017927.1 (624274 . . . 627639)
ID: 12975630
60. SALIVA_0715

CRISPR-associated endonuclease, Csn1 family [*Streptococcus salivarius* JIM8777]
Other Aliases: SALIVA_0715
Annotation: NC_017595.1 (708034 . . . 711417)
ID: 12910728
61. csn1

CRISPR-associated protein csn1 [*Streptococcus mutans* LJ23]
Other Aliases: SMULJ23_0701
Annotation: NC_017768.1 (751695 . . . 755732)
ID: 12898085
62. RIA_1455

CRISPR-associated protein, SAG0894 [*Riemerella anatipestifer* RA-GD]
Other Aliases: RIA_1455
Genomic context: Chromosome
Annotation: NC_017569.1 (1443996 . . . 1448198)
ID: 12613647
63. STND_0658

CRISPR-associated endonuclease, Csn1 family [*Streptococcus thermophilus* ND03]
Other Aliases: STND_0658
Genomic context: Chromosome
Annotation: NC_017563.1 (633621 . . . 636986)
ID: 12590813
64. RAOC_1034 putative BCR [*Riemerella anatipestifer* ATCC 11845 = DSM 15868]
Other Aliases: RAOC_1034
Genomic context: Chromosome
Annotation: NC_017045.1 (1023494 . . . 1026931, complement)
ID: 11996006
65. Sinf_1255

CRISPR-associated protein, SAG0894 family [*Streptococcus infantarius* subsp. *infantarius* CJ18]
Other Aliases: Sinf_1255
Genomic context: Chromosome
Annotation: NC_016826.1 (1276484 . . . 1280611, complement)
ID: 11877786
66. Nitsa_1472

CRISPR-associated protein, csn1 family [*Nitratifractor salsuginis* DSM 16511]
Other Aliases: Nitsa_1472
Genomic context: Chromosome
Annotation: NC_014935.1 (1477331 . . . 1480729)
ID: 10148263
67. NLA_17660 hypothetical protein [*Neisseria lactamica* 020-06]
Other Aliases: NLA_17660
Genomic context: Chromosome
Annotation: NC_014752.1 (1890078 . . . 1893326)
ID: 10006697

TABLE 2-continued

CRISPR-Associated Endonucleases
[Gene ID numbers refer to genes in the NCBI Gene Database as at September 2013; all sequence information relating to the gene IDs below is incorporated herein by reference for possible use in the present invention]

68. SmuNN2025_0694 hypothetical protein [*Streptococcus mutans* NN2025]
Other Aliases: SmuNN2025_0694
Genomic context: Chromosome
Annotation: NC_013928.1 (737258 . . . 741295)
ID: 8834629
69. SDEG_1231 hypothetical protein [*Streptococcus dysgalactiae* subsp. *equisimilis* GGS_124]
Other Aliases: SDEG_1231
Chromosome: 1
Annotation: Chromosome 1NC_012891.1 (1176755 . . . 1180870, complement)
ID: 8111553
70. NMCC_0397 hypothetical protein [*Neisseria meningitidis* 053442]
Other Aliases: NMCC_0397
Genomic context: Chromosome
Annotation: NC_010120.1 (402733 . . . 405981, complement)
ID: 5796426
71. SAK_1017 hypothetical protein [*Streptococcus agalactiae* A909]
Other Aliases: SAK_1017
Genomic context: Chromosome
Annotation: NC_007432.1 (980303 . . . 984415)
ID: 3686185
72. M5005_Spy_0769 hypothetical protein [*Streptococcus pyogenes* MGAS5005]
Other Aliases: M5005_Spy_0769
Genomic context: Chromosome
Annotation: NC_007297.1 (773340 . . . 777446)
ID: 3572134
73. MS53_0582 hypothetical protein [*Mycoplasma synoviae* 53]
Other Aliases: MS53_0582
Genomic context: Chromosome
Annotation: NC_007294.1 (684155 . . . 688099)
ID: 3564051
74. DIP0036 hypothetical protein [*Corynebacterium diphtheriae* NCTC 13129]
Other Aliases: DIP0036
Genomic context: Chromosome
Annotation: NC_002935.2 (34478 . . . 37732)
ID: 2650188
75. WS1613 hypothetical protein [*Wolinella succinogenes* DSM 1740]
Other Aliases: WS1613
Genomic context: Chromosome
Annotation: NC_005090.1 (1525628 . . . 1529857)
ID: 2553552
76. PM1127 hypothetical protein [*Pasteurella multocida* subsp. *multocida* str. Pm70]
Other Aliases: PM1127
Genomic context: Chromosome
Annotation: NC_002663.1 (1324015 . . . 1327185, complement)
ID: 1244474
77. SPs1176 hypothetical protein [*Streptococcus pyogenes* SSI-1]
Other Aliases: SPs1176
Genomic context: Chromosome
Annotation: NC_004606.1 (1149610 . . . 1153716, complement)
ID: 1065374

TABLE 2-continued

CRISPR-Associated Endonucleases
[Gene ID numbers refer to genes in the NCBI Gene Database as at September 2013; all sequence information relating to the gene IDs below is incorporated herein by reference for possible use in the present invention]

78. SMU_1405c hypothetical protein [*Streptococcus mutans* UA159]
Other Aliases: SMU_1405c, SMU.1405c
Genomic context: Chromosome
Annotation: NC_004350.2 (1330942 . . . 1334979, complement)
ID: 1028661

79. lin2744 hypothetical protein [*Listeria innocua* Clip11262]
Other Aliases: lin2744
Genomic context: Chromosome
Annotation: NC_003212.1 (2770707 . . . 2774711, complement)
ID: 1131597

80. csn1B

CRISPR-associated protein [*Streptococcus gallolyticus* subsp. *gallolyticus* ATCC 43143]
Other Aliases: SGGB_1441
Annotation: NC_017576.1 (1489111 . . . 1493226, complement)
ID: 12630646

81. csn1A

CRISPR-associated protein [*Streptococcus gallolyticus* subsp. *gallolyticus* ATCC 43143]
Other Aliases: SGGB_1431
Annotation: NC_017576.1 (1480439 . . . 1483831, complement)
ID: 12630636

82. cas9

CRISPR-associated protein [*Corynebacterium ulcerans* 809]
Other Aliases: CULC809_00033
Genomic context: Chromosome
Annotation: NC_017317.1 (30370 . . . 33063, complement)
ID: 12286148

83. GDI_2123 hypothetical protein [*Gluconacetobacter diazotrophicus* PAI 5]
Other Aliases: GDI_2123
Genomic context: Chromosome
Annotation: NC_010125.1 (2177083 . . . 2180235)
ID: 5792482

84. Nham_4054 hypothetical protein [*Nitrobacter hamburgensis* X14]
Other Aliases: Nham_4054
Genomic context: Plasmid 1
Annotation: NC_007959.1 (13284 . . . 16784, complement)
ID: 4025380

85. str0657 hypothetical protein [*Streptococcus thermophilus* CNRZ1066]
Other Aliases: str0657
Genomic context: Chromosome
Annotation: NC_006449.1 (619189 . . . 622575)
ID: 3165636

86. stu0657 hypothetical protein [*Streptococcus thermophilus* LMG 18311]
Other Aliases: stu0657
Genomic context: Chromosome
Annotation: NC_006448.1 (624007 . . . 627375)
ID: 3165000

87. SpyM3_0677 hypothetical protein [*Streptococcus pyogenes* MGAS315]
Other Aliases: SpyM3_0677
Genomic context: Chromosome
Annotation: NC_004070.1 (743040 . . . 747146)
ID: 1008991

88. HFMG06CAA_5227

Csn1 family CRISPR-associated protein [*Mycoplasma gallisepticum* CA06_2006.052-5-2P]
Other Aliases: HFMG06CAA_5227
Genomic context: Chromosome
Annotation: NC_018412.1 (895338 . . . 899147)
ID: 13464859

TABLE 2-continued

CRISPR-Associated Endonucleases
[Gene ID numbers refer to genes in the NCBI Gene Database as at September 2013; all sequence information relating to the gene IDs below is incorporated herein by reference for possible use in the present invention]

89. HFMG01WIA_5025

Csn1 family CRISPR-associated protein [*Mycoplasma gallisepticum* WI01_2001.043-13-2P]
Other Aliases: HFMG01WIA_5025
Genomic context: Chromosome
Annotation: NC_018410.1 (857648 . . . 861457)
ID: 13463863
90. HFMG01NYA_5169

Csn1 family CRISPR-associated protein [*Mycoplasma gallisepticum* NY01_2001.047-5-1P]
Other Aliases: HFMG01NYA_5169
Genomic context: Chromosome
Annotation: NC_018409.1 (883511 . . . 887185)
ID: 13462600
91. HFMG96NCA_5295

Csn1 family CRISPR-associated protein [*Mycoplasma gallisepticum* NC96_1596-4-2P]
Other Aliases: HFMG96NCA_5295
Genomic context: Chromosome
Annotation: NC_018408.1 (904664 . . . 908473)
ID: 13462279
92. HFMG95NCA_5107

Csn1 family CRISPR-associated protein [*Mycoplasma gallisepticum* NC95_13295-2-2P]
Other Aliases: HFMG95NCA_5107
Genomic context: Chromosome
Annotation: NC_018407.1 (871783 . . . 875592)
ID: 13461469
93. MGAS10750_Spy0921 hypothetical protein [*Streptococcus pyogenes* MGAS10750]
Other Aliases: MGAS10750_Spy0921
Genomic context: Chromosome
Annotation: NC_008024.1 (875719 . . . 879834)
ID: 4066656
94. XAC3262 hypothetical protein [*Xanthomonas axonopodis* pv. *citri* str. 306]
Other Aliases: XAC3262
Genomic context: Chromosome
Annotation: NC_003919.1 (3842310 . . . 3842765)
ID: 1157333
95. SSUST1_1305

CRISPR-system-like protein [*Streptococcus suis* ST1]
Other Aliases: SSUST1_1305
Genomic context: Chromosome
Annotation: NC_017950.1 (1293105 . . . 1297250, complement)
ID: 13017849
96. SSUD9_1467

CRISPR-associated protein, Csn1 family [*Streptococcus suis* D9]
Other Aliases: SSUD9_1467
Genomic context: Chromosome
Annotation: NC_017620.1 (1456318 . . . 1459686, complement)
ID: 12718289
97. BBta_3952 hypothetical protein [*Bradyrhizobium* sp. BTAi1]
Other Aliases: BBta_3952
Genomic context: Chromosome
Annotation: NC_009485.1 (4149455 . . . 4152649, complement)
ID: 5151538
98. CIY_03670

CRISPR-associated protein, Csn1 family [*Butyrivibrio fibrisolvens* 16/4]
Other Aliases: CIY_03670
Annotation: NC_021031.1 (309663 . . . 311960, complement)
ID: 15213189

TABLE 2-continued

CRISPR-Associated Endonucleases
[Gene ID numbers refer to genes in the NCBI Gene Database as at September 2013;
all sequence information relating to the gene IDs below is incorporated herein by
reference for possible use in the present invention]

99. A11Q_912

CRISPR-associated protein, Csn1 family [*Bdellovibrio exovorus* JSS]
Other Aliases: A11Q_912
Genomic context: Chromosome
Annotation: NC_020813.1 (904781 . . . 907864, complement)
ID: 14861475
100. MCYN0850

Csn1 family CRISPR-associated protein [*Mycoplasma cynos* C142]
Other Aliases: MCYN_0850
Annotation: NC_019949.1 (951497 . . . 955216, complement)
ID: 14356531
101. SaSA20_0769

CRISPR-associated protein [*Streptococcus agalactiae* SA20-06]
Other Aliases: SaSA20_0769
Genomic context: Chromosome
Annotation: NC_019048.1 (803597 . . . 807709)
ID: 13908026
102. csn1

CRISPR-associated protein, Csn1 family [*Streptococcus pyogenes* A20]
Other Aliases: A20_0810
Genomic context: Chromosome
Annotation: NC_018936.1 (772038 . . . 776144)
ID: 13864445
103. P700755_000291

CRISPR-associated protein Cas9/Csn1, subtype II [*Psychroflexus torquis* ATCC 700755]
Other Aliases: P700755_000291
Genomic context: Chromosome
Annotation: NC_018721.1 (312899 . . . 317428)
ID: 13804571
104. A911_07335

CRISPR-associated protein [*Campylobacter jejuni* subsp. *jejuni* PT14]
Other Aliases: A911_07335
Genomic context: Chromosome
Annotation: NC_018709.2 (1450217 . . . 1453180, complement)
ID: 13791138
105. ASU2_02495

CRISPR-associated endonuclease Csn1 family protein [*Actinobacillus suis* H91-0380]
Other Aliases: ASU2_02495
Genomic context: Chromosome
Annotation: NC_018690.1 (552318 . . . 555482)
ID: 13751600
106. csn1

CRISPR-associated protein [*Listeria monocytogenes* SLCC2540]
Other Aliases: LMOSLCC2540_2635
Annotation: NC_018586.1 (2700744 . . . 2704748, complement)
ID: 13647248
107. csn1

CRISPR-associated protein [*Listeria monocytogenes* SLCC5850]
Other Aliases: LMOSLCC5850_2605
Annotation: NC_018592.1 (2646023 . . . 2650027, complement)
ID: 13626042
108. csn1

CRISPR-associated protein [*Listeria monocytogenes* serotype 7 str. SLCC2482]
Other Aliases: LMOSLCC2482_2606
Annotation: NC_018591.1 (2665393 . . . 2669397, complement)
ID: 13605045
109. csn1

CRISPR-associated protein [*Listeria monocytogenes* SLCC2755]
Other Aliases: LMOSLCC2755_2607
Annotation: NC_018587.1 (2694850 . . . 2698854, complement)
ID: 13599053

TABLE 2-continued

CRISPR-Associated Endonucleases
[Gene ID numbers refer to genes in the NCBI Gene Database as at September 2013;
all sequence information relating to the gene IDs below is incorporated herein by
reference for possible use in the present invention]

110. BN148_1523c

CRISPR-associated protein [*Campylobacter jejuni* subsp. *jejuni* NCTC 11168-BN148]
Other Aliases: BN148_1523c
Annotation: NC_018521.1 (1456880 . . . 1459834, complement)
ID: 13530688
111. Belba_3201

CRISPR-associated protein Cas9/Csn1, subtype II/NMEMI [*Belliella baltica* DSM 15883]
Other Aliases: Belba_3201
Genomic context: Chromosome
Annotation: NC_018010.1 (3445311 . . . 3449369, complement)
ID: 13056967
112. FN3523_1121 membrane protein [*Francisella* cf. *novicida* 3523]
Other Aliases: FN3523_1121
Genomic context: Chromosome
Annotation: NC_017449.1 (1129528 . . . 1134468, complement)
ID: 12924881
113. cas9

CRISPR-associated protein Cas9/Csn1, subtype II/NMEMI [*Prevotella intermedia* 17]
Other Aliases: PIN17_A0201
Chromosome: II
Annotation: Chromosome IINC_017861.1 (240722 . . . 244864)
ID: 12849954
114. csn1

CRISPR-associated protein, Csn1 family [*Streptococcus thermophilus* JIM 8232]
Other Aliases: STH8232_0853
Annotation: NC_017581.1 (706443 . . . 709808)
ID: 12637306
115. LMOG_01918

CRISPR-associated protein [*Listeria monocytogenes* J0161]
Other Aliases: LMOG_01918
Genomic context: Chromosome
Annotation: NC_017545.1 (2735374 . . . 2739378, complement)
ID: 12557915
116. LMRG_02138

CRISPR-associated protein [*Listeria monocytogenes* 10403S]
Other Aliases: LMRG_02138
Genomic context: Chromosome
Annotation: NC_017544.1 (2641981 . . . 2645985, complement)
ID: 12554876
117. CJSA_1443 putative CRISPR-associated protein [*Campylobacter jejuni* subsp. *jejuni* IA3902]
Other Aliases: CJSA_1443
Genomic context: Chromosome
Annotation: NC_017279.1 (1454273 . . . 1457227, complement)
ID: 12250720
118. csn1

CRISPR-associated protein Csn1 [*Streptococcus pyogenes* MGAS1882]
Other Aliases: MGAS1882_0792
Genomic context: Chromosome
Annotation: NC_017053.1 (775696 . . . 779799)
ID: 12014080
119. csn1

CRISPR-associated protein Csn1 [*Streptococcus pyogenes* MGAS15252]
Other Aliases: MGAS15252_0796
Genomic context: Chromosome
Annotation: NC_017040.1 (778271 . . . 782374)
ID: 11991096
120. cas3

CRISPR-associated endonuclease [*Corynebacterium diphtheriae* HC02]
Other Aliases: CDHC02_0036
Genomic context: Chromosome
Annotation: NC_016802.1 (37125 . . . 40379)
ID: 11739116

TABLE 2-continued

CRISPR-Associated Endonucleases
[Gene ID numbers refer to genes in the NCBI Gene Database as at September 2013; all sequence information relating to the gene IDs below is incorporated herein by reference for possible use in the present invention]

121. cas3

CRISPR-associated endonuclease [*Corynebacterium diphtheriae* C7 (beta)]
Other Aliases: CDC7B_0035
Genomic context: Chromosome
Annotation: NC_016801.1 (36309 . . . 39563)
ID: 11737358
122. cas3

CRISPR-associated endonuclease [*Corynebacterium diphtheriae* BH8]
Other Aliases: CDBH8_0038
Genomic context: Chromosome
Annotation: NC_016800.1 (37261 . . . 40515)
ID: 11735325
123. cas3

CRISPR-associated endonuclease [*Corynebacterium diphtheriae* 31A]
Other Aliases: CD31A_0036
Genomic context: Chromosome
Annotation: NC_016799.1 (34597 . . . 37851)
ID: 11731168
124. cas3

CRISPR-associated endonuclease [*Corynebacterium diphtheriae* VA01]
Other Aliases: CDVA01_0033
Genomic context: Chromosome
Annotation: NC_016790.1 (34795 . . . 38049)
ID: 11717708
125. cas3

CRISPR-associated endonuclease [*Corynebacterium diphtheriae* HC01]
Other Aliases: CDHC01_0034
Genomic context: Chromosome
Annotation: NC_016786.1 (35060 . . . 38314)
ID: 11708318
126. cas9

CRISPR-associated protein [*Corynebacterium diphtheriae* HC01]
Other Aliases: CDHC01_2103
Genomic context: Chromosome
Annotation: NC_016786.1 (2246368 . . . 2248998)
ID: 11708126
127. PARA_18570 hypothetical protein [*Haemophilus parainfluenzae* T3T1]
Other Aliases: PARA_18570
Genomic context: Chromosome
Annotation: NC_015964.1 (1913335 . . . 1916493)
ID: 11115627
128. HDN1F_34120 hypothetical protein [*gamma proteobacterium* HdN1]
Other Aliases: HDN1F_34120
Genomic context: Chromosome
Annotation: NC_014366.1 (4143336 . . . 4146413, complement)
ID: 9702142
129. SPy_1046 hypothetical protein [*Streptococcus pyogenes* M1 GAS]
Other Aliases: SPy_1046
Genomic context: Chromosome
Annotation: NC_002737.1 (854757 . . . 858863)
ID: 901176
130. GBS222_0765

Hypothetical protein [*Streptococcus agalactiae*]
Other Aliases: GBS222_0765
Annotation: NC_021195.1 (810875 . . . 814987)
ID: 15484689

TABLE 2-continued

CRISPR-Associated Endonucleases
[Gene ID numbers refer to genes in the NCBI Gene Database as at September 2013; all sequence information relating to the gene IDs below is incorporated herein by reference for possible use in the present invention]

131. NE061598_03330 hypothetical protein [*Francisella tularensis* subsp. *tularensis* NE061598]
Other Aliases: NE061598_03330
Genomic context: Chromosome
Annotation: NC_017453.1 (601219 . . . 604590)
ID: 12437259
132. NMV_1993 hypothetical protein [*Neisseria meningitidis* 8013]
Other Aliases: NMV_1993
Annotation: NC_017501.1 (1917073 . . . 1920321)
ID: 12393700
133. csn1 hypothetical protein [*Campylobacter jejuni* subsp. *jejuni* M1]
Other Aliases: CJM1_1467
Genomic context: Chromosome
Annotation: NC_017280.1 (1433667 . . . 1436252, complement)
ID: 12249021
134. FTU_0629 hypothetical protein [*Francisella tularensis* subsp. *tularensis* TIGB03]
Other Aliases: FTU_0629
Genomic context: Chromosome
Annotation: NC_016933.1 (677092 . . . 680463)
ID: 11890131
135. NMAA_0315 hypothetical protein [*Neisseria meningitidis* WUE 2594]
Other Aliases: NMAA_0315
Annotation: NC_017512.1 (377010 . . . 380258, complement)
ID: 12407849
136. WS1445 hypothetical protein [*Wolinella succinogenes* DSM 1740]
Other Aliases: WS1445
Genomic context: Chromosome
Annotation: NC_005090.1 (1388202 . . . 1391381, complement)
ID: 2554690
137. THITE_2123823 hypothetical protein [*Thielavia terrestris* NRRL 8126]
Other Aliases: THITE_2123823
Chromosome: 6
Annotation: Chromosome 6NC_016462.1 (1725696 . . . 1725928)
ID: 11523019
138. XAC29_16635 hypothetical protein [*Xanthomonas axonopodis* Xac29-1]
Other Aliases: XAC29_16635
Genomic context: Chromosome
Annotation: NC_020800.1 (3849847 . . . 3850302)
ID: 14853997
139. M1GAS476_0830 hypothetical protein [*Streptococcus pyogenes* M1476]
Other Aliases: M1GAS476_0830
Chromosome: 1
Annotation: NC_020540.1 (792119 . . . 796225)
ID: 14819166
140. Piso0_000203

Piso0_000203 [*Millerozyma farinosa* CBS 7064]
Other Aliases: GNLVRS01_PISO0A04202g
Other Designations: hypothetical protein
Chromosome: A
Annotation: NC_020226.1 (343553 . . . 343774, complement)
ID: 14528449

TABLE 2-continued

CRISPR-Associated Endonucleases
[Gene ID numbers refer to genes in the NCBI Gene Database as at September 2013; all sequence information relating to the gene IDs below is incorporated herein by reference for possible use in the present invention]

141. G148_0828 hypothetical protein [*Riemerella anatipestifer* RA-CH-2]
Other Aliases: G148_0828
Genomic context: Chromosome
Annotation: NC_020125.1 (865673 . . . 869875)
ID: 14447195
142. csn1 hypothetical protein [*Streptococcus dysgalactiae* subsp. *equisimilis* AC-2713]
Other Aliases: SDSE_1207
Annotation: NC_019042.1 (1134173 . . . 1138288, complement)
ID: 13901498
143. A964_0899 hypothetical protein [*Streptococcus agalactiae* GD201008-001]
Other Aliases: A964_0899
Genomic context: Chromosome
Annotation: NC_018646.1 (935164 . . . 939276)
ID: 13681619
144. FNFX1_0762 hypothetical protein [*Francisella* cf. *novicida* Fx1]
Other Aliases: FNFX1_0762
Genomic context: Chromosome
Annotation: NC_017450.1 (781484 . . . 786373)
ID: 12435564
145. FTV_0545 hypothetical protein [*Francisella tularensis* subsp. *tularensis* TI0902]
Other Aliases: FTV_0545
Genomic context: Chromosome
Annotation: NC_016937.1 (601185 . . . 604556)
ID: 11880693
146. FTL_1327 hypothetical protein [*Francisella tularensis* subsp. *holarctica* LVS]
Other Aliases: FTL_1327
Genomic context: Chromosome
Annotation: NC_007880.1 (1262508 . . . 1263689, complement)
ID: 3952607
147. FTL_1326 hypothetical protein [*Francisella tularensis* subsp. *holarctica* LVS]
Other Aliases: FTL_1326
Genomic context: Chromosome
Annotation: NC_007880.1 (1261927 . . . 1262403, complement)
ID: 3952606

We claim:

1. A method for modifying a genome at a genomic locus of interest in a non-human mammal zygote, the method comprising assembling in vitro a ribonucleoprotein (RNP) complex, comprising contacting a purified clustered regularly interspaced short palindromic repeats (CRISPR) associated 9 (Cas9) protein and at least two single guide RNAs (sgRNAs) that hybridize to a CRISPR target sequence at the same genomic locus of interest; and injecting the RNP complex into the non-human mammal zygote; and injecting an incoming nucleic acid that comprises:
  (i) a 5' homology arm that is homologous to a 5' target sequence at the genomic locus of interest and is homologous to a region 5' of a first protospacer adjacent motif (PAM) sequence contained within the genomic locus of interest; and
  (ii) a 3' homology arm that is homologous to a 3' target sequence at the genomic locus of interest and is homologous to a region 3' of a second PAM sequence contained within the genomic locus of interest; and
  (iii) optionally an insert nucleic acid sequence; wherein the method uses Cas9 mediated nucleic acid cleavage to create 5' and 3' cut ends in the region between the 5' target sequence and the 3' target sequence; wherein, following the injection step:
  (a) which injection step comprises injecting an incoming nucleic acid, the genome of the zygote is modified to comprise a targeted genetic modification comprising a deletion of a region of the genomic locus of interest, wherein the targeted genetic modification is a deletion of from 1 kb to at least 100 kb; and/or
  (b) which injection step comprises injecting an incoming nucleic acid, the genome of the zygote is modified to comprise a targeted genetic modification comprising insertion of the insert nucleic acid sequence at the genomic locus of interest.

2. The method of claim 1, wherein the zygote is injected at the 1 or 2 cell stage.

3. The method of claim 1, wherein the injection is cytoplasmic zygote injection.

4. The method of claim 1, wherein the non-human mammal is a rat or mouse.

5. The method of claim 1, wherein the zygote is developed into a mouse.

6. The method of claim 1, wherein the Cas9 protein is a nickase.

7. The method of claim 1, wherein two sgRNAs are injected into the zygote.

8. The method of claim 1, wherein the targeted genomic modification comprises a deletion of a regulatory element, a promoter, an enhancer, or a sequence that encodes all or part of a target protein or domain thereof, wherein the target protein or domain thereof comprises an interleukin, a receptor, a cell surface receptor, a growth factor, a hormone, an antibody, an antibody variable domain, an antibody binding site, an antagonist, an agonist, an exon, a cell membrane protein, a secreted protein, an intracellular protein, or a cytokine.

9. The method of claim 1, wherein the targeted genomic modification comprises a deletion of all or part of one or more non-human antibody gene segments or a deletion of a sequence that encodes all or part of a non-human protein, a non-human protein subunit or domain, a non-human antibody variable region, or a non-human antibody constant region.

10. The method of claim 1, wherein the targeted genomic modification comprises a knock-out of a target protein or domain thereof.

11. The method of claim 1, wherein the targeted genetic modification is a deletion of from 1 kb to at least 100 kb; and the incoming nucleic acid is an insertion of the insert nucleic acid of 10 to 40 nucleotides.

12. The method of claim 1, wherein when the incoming nucleic acid is injected into the non-human mammal zygote, each of the 5' and 3' homology arms are at least 50 nucleotides long.

13. The method of claim 1, wherein when the incoming nucleic acid is injected into the non-human mammal zygote, the targeted genomic modification is the insertion of the insert nucleic acid at the genomic locus of interest.

14. The method of claim 13, wherein the insert nucleic acid
  (a) is a regulatory element, a promoter, an enhancer, or a sequence that encodes all or part of an interleukin, a receptor, a cell surface receptor, a growth factor, a hormone, an antibody, an antibody variable domain, an antibody binding site, an antagonist, an agonist, an exon, a cell membrane protein, a secreted protein, an intracellular protein, or a cytokine; and/or
  (b) comprises all or part of one or more human antibody gene segments or encodes all or part of a human protein, a human protein subunit or domain, a human antibody variable region, or a human antibody constant region.

15. The method of claim 1, wherein when the incoming nucleic acid is injected into the non-human mammal zygote, the insert nucleic acid is from 200 nucleotides to at least 100 kb.

16. The method of claim 1, wherein when the incoming nucleic acid is injected into the non-human mammal zygote, the insert nucleic acid (a) replaces a target sequence in whole or in part at the endogenous location of the target gene at the genomic locus of interest, wherein the insert nucleic acid comprises all or part of one or more human antibody gene segments or encodes all or part of a human protein, a human protein subunit or domain, a human antibody variable region, or a human antibody constant region; and/or (b) replaces an orthologous or homologous sequence in the genome, wherein the insert nucleic acid comprises all or part of one or more human antibody gene segments or encodes all or part of a human protein, a human protein subunit or domain, a human antibody variable region, or a human antibody constant region.

17. The method of claim 16, wherein the insert nucleic acid is from 40 nucleotides to at least 100 kb and/or the deletion is from 1 kb to at least 100 kb.

18. The method of claim 1, wherein INDELS are created in a genomic locus of interest to knock-out or reduce expression of the genomic locus of interest, wherein the genomic locus of interest is a regulatory element, a promoter, an enhancer, or a sequence that encodes an interleukin, a receptor, a cell surface receptor, a growth factor, a hormone, an antibody, an antibody variable domain, an antibody binding site, an antagonist, an agonist, an exon, a cell membrane protein, a secreted protein, an intracellular protein, or a cytokine.

19. A mouse developed from a zygote obtained by the method of claim 1.

* * * * *

UNITED STATES PATENT AND TRADEMARK OFFICE
CERTIFICATE OF CORRECTION

| | |
|---|---|
| PATENT NO. | : 11,920,128 B2 |
| APPLICATION NO. | : 16/516996 |
| DATED | : March 5, 2024 |
| INVENTOR(S) | : Bradley et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 830 days.

Signed and Sealed this
Eighth Day of October, 2024

*Katherine Kelly Vidal*

Katherine Kelly Vidal
*Director of the United States Patent and Trademark Office*